US012472247B2

(12) United States Patent
Kim et al.

(10) Patent No.: US 12,472,247 B2
(45) **Date of Patent: *Nov. 18, 2025**

(54) IMMUNE ADJUVANT COMPRISING HEPATITIS B VIRUS-DERIVED POLYPEPTIDE

(71) Applicant: SEOUL NATIONAL UNIVERSITY R&DB FOUNDATION, Seoul (KR)

(72) Inventors: Bum Joon Kim, Seoul (KR); Byoung Jun Kim, Gyeonggi-do (KR); Yu Min Choi, Seoul (KR); Hye In Jeong, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 295 days.

This patent is subject to a terminal disclaimer.

(21) Appl. No.: 18/021,261

(22) PCT Filed: Aug. 12, 2021

(86) PCT No.: PCT/KR2021/010709

§ 371 (c)(1),
(2) Date: Feb. 14, 2023

(87) PCT Pub. No.: WO2022/035246

PCT Pub. Date: Feb. 17, 2022

(65) Prior Publication Data

US 2023/0321222 A1 Oct. 12, 2023

(30) Foreign Application Priority Data

Aug. 14, 2020 (KR) ........................ 10-2020-0102683

(51) Int. Cl.

| | |
|---|---|
| ***A61K 39/295*** | (2006.01) |
| ***A61K 39/00*** | (2006.01) |
| ***A61K 39/39*** | (2006.01) |
| ***A61P 37/04*** | (2006.01) |

(52) U.S. Cl.

CPC ............ *A61K 39/295* (2013.01); *A61K 39/00* (2013.01); *A61K 39/39* (2013.01); *A61P 37/04* (2018.01); *A61K 2039/55516* (2013.01)

(58) Field of Classification Search

None

See application file for complete search history.

(56) References Cited

U.S. PATENT DOCUMENTS

| | | | | |
|---|---|---|---|---|
| 2003/0171538 | A1 | 9/2003 | Chisari | |
| 2021/0093712 | A1* | 4/2021 | Balsitis | A61K 39/12 |

FOREIGN PATENT DOCUMENTS

| | | | |
|---|---|---|---|
| CN | 104873969 | A | 9/2015 |
| JP | 2010-516807 | A | 5/2010 |
| KR | 10-2011-0090926 | A | 8/2011 |
| KR | 10-2019-0128999 | A | 11/2019 |

OTHER PUBLICATIONS

Nkolola et al. Lancet HIV. Feb. 2024 ; 11(2): e117-e124. doi:10.1016/S2352-3018(23)00264-3.*

Vaccines (Basel). Dec. 18, 2023;11(12):1862.*

Lai et al. pj Vaccines 8, 158 (2023). https://doi.org/10.1038/s41541-023-00750-7.*

Chuai et al., "Poly(I:C)/Alum Mixed Adjuvant Priming Enhances HBV Subunit Vaccine-Induced Immunity in Mice when Combined with Recombinant Adenoviral-Based HBV Vaccine Boosting," PLOS One, 8 (1): e54126 (2013).

International Search Report issued in corresponding International Patent Application No. PCT/KR2021/010709 dated Dec. 13, 2021.

* cited by examiner

*Primary Examiner* — Oluwatosin A Ogunbiyi

(74) *Attorney, Agent, or Firm* — Morgan, Lewis & Bockius LLP

(57) ABSTRACT

Provided is an immune adjuvant including a polypeptide consisting of an amino acid sequence of SEQ ID NO: 2. The polypeptide is a hepatitis B virus-derived polypeptide, is effective in enhancing immunity through co-administration with vaccines as a single immune adjuvant, and in particular, when co-administered with another immune adjuvant, may exhibit a more remarkable immunity enhancement effect. Furthermore, the polypeptide is a single molecule having only 6 amino acids, is not cytotoxic, and has excellent in vivo stability.

11 Claims, 100 Drawing Sheets

Specification includes a Sequence Listing.

Anti-HIV effects

Anti-HBV effects

IMMUNE ADJUVANT COMPRISING HEPATITIS B VIRUS-DERIVED POLYPEPTIDE

A computer readable text file, entitled "SequenceListing.txt," created on or about Feb. 27, 2023 with a file size of 15,664 bytes contains the sequence listing for this application and is hereby incorporated by reference in its entirety.

TECHNICAL FIELD

The present disclosure relates to an immune adjuvant including a hepatitis B virus-derived polypeptide.

BACKGROUND ART

Vaccine development largely requires three technologies related to antigens, immune adjuvants, and vaccine delivery, among these, the immune adjuvant technology is for maintaining a high protective immune response to an antigen for a long time when a subject is vaccinated. Vaccine development has been mainly focused on antigen development technology, but the importance of immune adjuvants is being highlighted for developing preventive vaccines for infectious diseases that have not yet been successfully developed or to improve vaccines with unsatisfactory preventive effects.

Recently, studies on immune adjuvants have continued, but there still remains challenges of having to specifically identify mechanisms of action of many immune adjuvants, and having to understand and overcome differences of vaccine efficacies that occur in animal experiments and clinical trials. In addition, researches need to be continued for effective combination of known immune adjuvants with antigens, appropriate vaccine delivery methods, and whether synergistic effects and side effects appear in the vaccine efficacy when various immune adjuvants are used in combination.

Therefore, based on the results that Poly6, a peptide-derived adjuvant, effectively enhances immunity when applied to various vaccine types (DNA and protein) and immunization methods (intramuscular, IM; intraperitoneal, IP; and subcutaneous, SC), the present inventors are applying Poly6 as a new immune adjuvant, and as a complex immune adjuvant by using in combination with existing immune adjuvants.

DETAILED DESCRIPTION OF THE DISCLOSURE

Technical Problem

An aspect is to provide an immune adjuvant including a polypeptide including an amino acid sequence of SEQ ID NO: 2.

Another aspect is to provide a composition for enhancing immunity including the polypeptide including the amino acid sequence of SEQ ID NO: 2.

Another aspect is to provide a vaccine composition including the polypeptide including the amino acid sequence of SEQ ID NO: 2 and DNA or an antigen.

Still another aspect is to provide a method of enhancing immunity including administering the polypeptide including the amino acid sequence of SEQ ID NO: 2 and DNA or an antigen to a subject in need thereof.

Still another aspect is to provide a method of preventing at least one disease selected from the group consisting of liver diseases, acquired immune deficiency syndrome (AIDS), and tuberculosis, including administering the polypeptide including the amino acid sequence of SEQ ID NO: 2 and DNA or an antigen to a subject in need thereof.

Technical Solution to Problem

An aspect provides an immune adjuvant including a polypeptide including an amino acid sequence of SEQ ID NO: 2.

The term "polypeptide" refers to a polymer composed of two or more amino acids linked by amide bonds (or peptide bonds). The polypeptide may consist of any one amino acid sequence selected from the group consisting of SEQ ID NO: 2 and SEQ ID NO: 3, and may specifically consist of the amino acid sequence of SEQ ID NO: 2. The polypeptide may include a polypeptide having sequence homology of about 70% or more, about 75% or more, about 80% or more, about 85% or more, about 90% or more, about 92% or more, about 95% or more, about 97% or more, about 98% or more, or about 99% or more, respectively, with the amino acid sequence of SEQ ID NO: 1, SEQ ID NO: 2, or SEQ ID NO: 3.

In the present specification, amino acids of a peptide or polypeptide may be conservatively or non-conservatively substituted.

The term "conservative substitution", used herein, refers to substitution of an amino acid present in a natural sequence of a peptide with a natural or non-naturally occurring amino acid or a peptidomimetic having similar three-dimensional properties. When a side chain of the naturally occurring amino acid to be substituted is polar or hydrophobic, the conservative substitution may be made with a naturally occurring amino acid, non-naturally occurring amino acid, or peptidomimetic moiety that is likewise polar or hydrophobic (in addition to having the same steric properties as the side chain of the substituted amino acid).

Because naturally occurring amino acids are typically classified according to their properties, conservative substitution by naturally occurring amino acids may be easily determined by considering the fact that charged amino acids are substituted with sterically similar uncharged amino acids, which are considered conservative substituents, according to the present disclosure.

Amino acid analogues known in the art (synthetic amino acids) may also be used to make conservative substitutions with non-naturally occurring amino acids. Peptidomimetics of naturally occurring amino acids are well documented in the literature known to those skilled in the art.

When making conservative substitutions, the substituted amino acids must have the same or similar functional groups on the side chain as the original amino acids.

The term "non-conservative substituent", used herein, refers to what substitutes an amino acid as present in a parent sequence with another natural or non-naturally occurring amino acid having different electrochemical and/or steric properties. Thus, a side chain of the substituting amino acid may be significantly larger than a side chain of a natural amino acid being substituted, and/or may have functional groups with electrical properties that are significantly different from those of the substituted amino acid. Specific examples of non-conservative substituents of this type include substituents of phenylalanine or cyclohexylmethylglycine for alanine, isoleucine for glycine, or —NH—CH[(—$CH_2$)5-COOH]—CO— for aspartic acid.

Although peptides or polypeptides herein are used linearly, it will be appreciated that cyclic forms of the peptides may also be used, provided that cyclization does not significantly interfere with the peptide properties.

Because the peptides or polypeptides herein are used in therapeutics that require them to be present in soluble form, the peptides or polypeptides of some embodiments herein may include serine and threonine, which may increase stability of the peptides or polypeptides due to a hydroxyl-containing side chain, which is one or more non-natural or natural polar amino acids, but are not limited thereto.

N-termini and C-termini of the peptides or polypeptides of the present specification may be protected by functional groups. Suitable functional groups are described in Greene and Wuts' "Protecting Groups in Organic Synthesis", John Wiley & Sons, Inc., Chapters 5 and 7, 1991, the contents of which are incorporated herein by reference. Thus, the peptides or polypeptides may be modified at the N-(amine) termini and/or C-(carboxyl) termini to create end-capped modified peptides.

The phrases "end-capped variant polypeptide" and "protected polypeptide", as used herein, are used interchangeably, and refer to a polypeptide in which the N-(amine) terminus and/or C-(carboxyl) terminus is modified. The end-capping modification refers to an attachment of a chemical moiety to an end of a polypeptide to form a cap. Such a chemical moiety is referred to herein as an end-capping moiety and are commonly referred to herein and in the art interchangeably as a peptide protecting moiety or a functional group. Hydroxyl protecting groups include, but are not limited to, ester, carbonate, and carbamate protecting groups. Amine protecting groups include, but are not limited to, alkoxy, and aryloxy carbonyl groups. Carboxylic acid protecting groups include, but are not limited to, aliphatic esters, benzyl esters, and aryl esters.

The phrase "end-capping moiety", used herein, refers to a moiety that modifies the N-terminus and/or C-terminus of the peptide, when attached to the terminus. End-capping modifications typically result in masking charges at a terminus of a peptide and/or altering its chemical properties such as hydrophobicity, hydrophilicity, reactivity, solubility, and the like. By selecting nature of the end-capping modifications, hydrophobicity/hydrophilicity as well as solubility of the peptide may be fine-tuned. According to certain embodiments, the protecting groups facilitate transport of the peptides attached thereto into cells. These residues may be hydrolyzed or enzymatically degraded in vivo in cells.

According to certain embodiments, the end-capping includes N-terminus end-capping. Representative examples of N-terminus end-capping residues include formyl, acetyl (also referred to herein as "AC"), trifluoroacetyl, benzyl, benzyloxycarbonyl (also referred to herein as "Cbz"), tert-butoxycarbonyl (also referred to herein as "Boc"), trimethylsilyl (also referred to herein as "TMS"), 2-trimethylsilyl-ethanesulfonyl (also referred to herein as "SES"), trityl and substituted trityl groups such as allyloxycarbonyl, 9-fluorenylmethyloxycarbonyl (also referred to herein as "Fmoc"), and nitro-veratryloxycarbonyl ("NVOC").

According to certain embodiments, the end-capping includes C-terminus end-capping. Examples of C-terminus end-capping residues are typical residues that induce acylation of a carboxyl group at the C-terminus, and may include alkylether, tetrahydropyranyl ether, trialkylsilyl ether, allylether, monomethoxytrityl, and dimethoxytrityl, as well as benzyl and trityl ether. Optionally, the —COOH group of the C-terminus-capping may be transformed into an amide group.

End-capping modifications of other peptides include substitution of amines and/or carboxyls with other moieties such as hydroxy, thiol, halide, alkyl, aryl, alkoxy, aryloxy, and the like.

In addition, the polypeptide may additionally include a targeting sequence, a tag, and an amino acid sequence prepared for a specific purpose for a labeled residue.

The term "homology", used herein, is for indicating a degree of similarity with a wild-type amino acid sequence, and comparison of such homology may be performed by using a comparison program widely known in the art, and homology between two or more sequences may be calculated as a percentage (%).

The polypeptide may be of natural origin or may be obtained by a variety of polypeptide synthesis methods well known in the art. As an example, the polypeptide may be prepared by using polynucleotide recombination and a protein expression system, or synthesized in vitro by using chemical synthesis methods such as a peptide synthesis method, and cell-free protein synthesis method. In addition, as an example, the polypeptide may be a peptide, a plant-derived tissue, or cell extract, a product obtained by culturing a microorganism (for example, bacteria, or fungi, and particularly yeast), specifically, may be derived from a hepatitis B virus (HBV) polymerase, and more specifically, may be derived from a preS1 region of the HBV polymerase.

The polypeptide may mature dendritic cells, increase migratory ability of the dendritic cells in the body, and may be used in combination with other vaccines to enhance immunity.

The polypeptide may also have antiviral activity. For example, the virus may be at least one selected from the group consisting of adenovirus, smallpox virus, polio virus, measles virus, severe fever with thrombocytopenia syndrome virus, influenza virus, hepatitis C virus, human immunodeficiency virus-1 (HIV-1), and hepatitis B virus (HBV), specifically, the virus may be at least one selected from the group consisting of human immunodeficiency virus-1 (HIV-1), and hepatitis B virus (HBV).

In an aspect, the immune adjuvant may further include another immune adjuvant.

The another immune adjuvant may be an existing immune adjuvant or may be a new immune adjuvant. When the another immune adjuvant is further included, a synergistic effect with the polypeptide may be exhibited, and immunity may be more effectively enhanced.

The another immune adjuvant may be, for example, at least one selected from the group consisting of aluminum salts (Alum), IL-12, granulocyte-macrophage colony-stimulating factor (GM-CSF), squalene, MF59, ASO3, ASO4, poly(I:C), monophosphoryl lipid A (MPL), GLA, flagellin, Imiquimod, R848, CpG ODN, CpG DNA, saponins (QS-21), C-type lectin ligands (TDB), α-galactosylceramide, muramyl dipeptide, lipopolysaccharide (LPS), Kuyl A, ASO1 (liposome mixed with monophosphoryl lipid A and saponin QS-21), IC31 (oligo nucleotide and cationic peptide), CFA01 (cationic liposome) and GLA-SE (oil-in-water emulsion of MPL and glucopyranosyl lipid), and specifically, may be aluminum salts (Alum).

In an aspect, the immune adjuvant may be co-administered with DNA or an antigen.

The DNA or the antigen may be derived from at least one selected from the group consisting of human immunodeficiency virus (HIV), hepatitis B virus (HBV), and *Mycobacterium tuberculosis*.

Specifically, the DNA may be at least one selected from the group consisting of a polynucleotide encoding a chorismate mutase, a polynucleotide encoding an Ag85B protein, a polynucleotide encoding a p24 protein, and a polynucleotide encoding an HBV S protein, and more specifically, DNA may be a polynucleotide encoding a chorismate mutase derived from *Mycobacterium tuberculosis*, a polynucleotide encoding an Ag85B protein derived from *Mycobacterium tuberculosis*, a polynucleotide encoding a p24 protein derived from human immunodeficiency virus (HIV), and a polynucleotide encoding an S protein derived from hepatitis B virus (HBV).

In addition, the antigen may specifically be at least one selected from the group consisting of a chorismate mutase, an Ag85B protein, a p24 protein, and an HBV S protein, and more specifically, the antigen may be at least one selected from the group consisting of a chorismate mutase derived from *Mycobacterium tuberculosis*, an Ag85B protein derived from *Mycobacterium tuberculosis*, a p24 protein derived from human immunodeficiency virus (HIV), and an s protein derived from hepatitis B virus (HBV).

In an aspect, the immune adjuvant may be at least one immune adjuvant of a vaccine for preventing infection caused by a pathogen selected from the group consisting of human immunodeficiency virus (HIV), hepatitis B virus (HBV), and *Mycobacterium tuberculosis.*

In addition, in an aspect, the immune adjuvant may be at least one immune adjuvant of a vaccine for preventing a disease selected from the group consisting of liver diseases, acquired immune deficiency syndrome (AIDS), and tuberculosis.

The acquired immune deficiency syndrome (AIDS) may be caused by HIV-1 infection, and the liver disease may be caused by HBV infection, and specifically, may be at least one selected from the group consisting of hepatitis, cirrhosis, and liver cancer, and more specifically, the liver disease may be developed from hepatitis B. In addition, the tuberculosis may be eye tuberculosis, skin tuberculosis, adrenal tuberculosis, kidney tuberculosis, epididymal tuberculosis, lymphatic tuberculosis, laryngeal tuberculosis, middle ear tuberculosis, intestinal tuberculosis, multidrug-resistant tuberculosis, pulmonary tuberculosis, gallbladder tuberculosis, bone tuberculosis, throat tuberculosis, lymph gland tuberculosis, breast tuberculosis, or spinal tuberculosis. In addition, the tuberculosis may be caused by K strain, which is a Korean type of highly pathogenic *Mycobacterium tuberculosis*, or Beijing tuberculosis strain.

The term "prevention" may refer to any activity that suppresses or delays an onset of tuberculosis in a subject by administering a vaccine composition according to an aspect.

The term "vaccine" refers to a pharmaceutical composition containing at least one immunologically active component that induces an immunological response in an animal. Immunologically active components of a vaccine may contain suitable elements of live or dead viruses or bacteria (subunit vaccines), and therefore, the elements may be prepared by: destroying whole viruses or bacteria or growing cultures thereof, and then obtaining the desired structure(s) by purification; performing a synthetic process induced by suitable manipulations of suitable systems such as bacteria, insects, mammals or other species followed by isolation and purification, or inducing a synthetic process in an animal in need of a vaccine by direct injection of genetic material by using a suitable pharmaceutical composition. The vaccine may contain one or more of the elements described above.

In an aspect, the immune adjuvant may increase an expression level of at least one cytokine selected from the group consisting of cytokines IL-2, IFN-γ, IL-10, IL-1β, IL-6, IL-12, IL-17 and TNF-α.

In addition, the immune adjuvant may enhance expression of IgG in serum more than when a vaccine is administered alone, and may further enhance immunity by further activating T cells.

Another aspect provides a composition for enhancing immunity including a polypeptide consisting of an amino acid sequence of SEQ ID NO: 2.

The "polypeptide", "immunity enhancement", etc. may be within the aforementioned range.

Another aspect provides a vaccine composition including a polypeptide consisting of the amino acid sequence of SEQ ID NO: 2 and DNA or an antigen.

The vaccine composition may be provided as a vaccine composition including the active ingredients alone or further including one or more immunologically acceptable carriers, excipients, or diluents.

Specifically, the carrier may be, for example, a colloidal suspension, a powder, a saline solution, lipid, liposomes, microspheres, or nano-spherical particles. The carriers may be complexed with or associated with a delivery vehicle and may be transported in vivo by using a known delivery system in the art such as lipids, liposomes, microparticles, gold, nanoparticles, polymers, condensation reagents, polysaccharides, polyamino acids, dendrimers, saponins, adsorption enhancing substances, or fatty acids.

When the vaccine composition is formulated, the vaccine composition may be prepared by using commonly used diluents or excipients such as lubricants, sweeteners, flavoring agents, emulsifiers, suspending agents, preservatives, fillers, extenders, binders, humectants, disintegrants, surfactants, etc. Solid formulations for oral administration may include tablets, pills, powders, granules, capsules, etc., and these solid formulations may be prepared by mixing the composition with at least one excipient such as starch, calcium carbonate, sucrose or lactose, gelatin, etc. In addition, lubricants such as magnesium stearate, or talc may be used in addition to simple excipients. Liquid formulations for oral administration include suspensions, oral liquids, emulsifiers, syrups, etc., and various excipients, for example, a humectant, a sweetener, a fragrance, or a preservative may be included in addition to commonly used simple diluents such as water, or liquid paraffin. Formulations for parenteral administration may include sterile aqueous solutions, non-aqueous solvents, suspensions, emulsions, lyophilized preparations, and suppositories. For the non-aqueous solvents and the suspensions, propylene glycol, polyethylene glycol, a vegetable oil such as olive oil, an injectable ester such as ethyl oleate, etc. may be used. As a base for suppositories, witepsol, macrogol, tween 61, cacao butter, laurin butter, glycero-gelatin, etc. may be used, and when prepared in a form of eye drops, known diluents or excipients may be used.

The vaccine composition may be provided in a mixture with a vaccine composition known in the art or an existing vaccine, and when the vaccine composition includes other vaccines, it is important to mix amounts that may obtain the maximum effect with the minimum amount without a side effect, which may be readily determined by a person skilled in the art.

The other vaccine may be a previously known vaccine composition, an existing vaccine or a newly developed vaccine.

In addition, in an aspect, the vaccine composition may be administered alone or in combination with other known tuberculosis vaccines, and may be administered simultaneously, separately, or sequentially, and may be administered once or multiple times. It is important to determine an administration method, an administration cycle, an administration dose, etc. that may obtain the maximum effect with a minimum amount without a side effect, by considering all of the above factors, which may be easily determined by those skilled in the art.

When the vaccine composition is mixed with other tuberculosis vaccines or co-administered, synergistic effects such as enhancement of immune activity may be more prominent than when the vaccine composition is provided alone or administered alone.

The term "administration" refers to introducing a predetermined substance into a subject by an appropriate method, and "subject" refers to all organisms such as rats, mice, livestock, and the like, including humans. As a specific example, the subject may be mammals including humans.

In an aspect, a route of administration of the vaccine composition may be at least one selected from the group consisting of oral, intravenous, intramuscular, intraarterial, intramedullary, intrathecal, intracardiac, transdermal, subcutaneous, intraperitoneal, intranasal, intestinal, intrathoracic, topical, sublingual, or intrarectal route, or the vaccine composition may be applied by external skin application, and specifically, the route of administration may be at least one selected from the group consisting of subcutaneous injection, and intranasal injection.

The vaccine composition may be administered to a subject in an immunologically effective amount. The "immunologically effective amount" refers to an amount sufficient to exhibit an effect of enhancing immune activity and an amount sufficient to not cause a side effect or serious or excessive immune reactions, and the exact dosage concentration varies depending on the specific immunogen to be administered, and may be easily determined by a person skilled in the art according to factors well known in the medical field, such as an age, weight, health, sex, and sensitivity to a drug of a subject, administration route, and administration method, and the effective amount may be administered once or several times.

For example, about 0.1 ng/kg/day to about 100 mg/kg/day of the vaccine composition according to an aspect may be administered.

In an aspect, the vaccine composition may be administered once a day or several times in aliquots. Specifically, based on 7 days, the vaccine composition may be administered in a cycle of 1 day break after 6 days of administration, 2 days break after 5 days of administration, 3 days break after 4 days of administration, 4 days break after 3 days of administration, 5 days break after 2 days of administration, 6 days after 1 day of administration.

The vaccine composition according to an aspect may include an immunologically acceptable vaccine protectant, an immune enhancer, a diluent, an absorption promoter, and the like, as needed. The vaccine protectant may include, for example, a lactose phosphate glutamate gelatin mixture. The immune enhancer may include, for example, aluminum hydroxide, mineral oil or other oils, or auxiliary molecules added to the vaccine or produced by the body after each induction by such additional components, such as interferons, interleukins, or growth factors. When the vaccine is a solution or injection, the vaccine may contain propylene glycol and sodium chloride in an amount sufficient to prevent hemolysis (for example, about 1%), when needed.

The vaccine composition according to an aspect may further include another immune adjuvant as an immune enhancer.

The immune adjuvant may be at least one selected from the group consisting of aluminum salts (Alum), MF59, ASO3, ASO4, poly(I:C), MPL, GLA, flagellin, Imiquimod, R848, CpG ODN, saponins (QS-21), C-type lectin ligands (TDB), α-galactosylceramide, ASO1 (liposome mixed with monophosphoryl lipid A and saponin QS-21), IC31 (oligo nucleotide and cationic peptide), CFA01 (cationic liposome) and GLA-SE (oil-in-water emulsion of MPL and glucopyranosyl lipid), and specifically, may be aluminum salts (Alum).

When the vaccine composition further includes another immune adjuvant, a synergistic effect that enhances immune activity may be more remarkably exhibited.

In an aspect, the DNA or the antigen may be derived from at least one selected from the group consisting of human immunodeficiency virus (HIV), hepatitis B virus (HBV), and *Mycobacterium tuberculosis.*

In addition, specifically, the DNA may be at least one selected from the group consisting of a polynucleotide encoding a chorismate mutase, a polynucleotide encoding an Ag85B protein, a polynucleotide encoding a p24 protein, and a polynucleotide encoding an HBV S protein, and more specifically, DNA may be a polynucleotide encoding a chorismate mutase derived from *Mycobacterium tuberculosis*, a polynucleotide encoding an Ag85B protein derived from *Mycobacterium tuberculosis*, a polynucleotide encoding a p24 protein derived from human immunodeficiency virus (HIV), and a polynucleotide encoding an s protein derived from hepatitis B virus (HBV).

In addition, the antigen may be, specifically, at least one selected from the group consisting of a chorismate mutase, an Ag85B protein, a p24 protein, and an HBV S protein, and more specifically, the antigen may be at least one selected from the group consisting of a chorismate mutase derived from *Mycobacterium tuberculosis*, an Ag85B protein derived from *Mycobacterium tuberculosis*, a p24 protein derived from human immunodeficiency virus (HIV), and an S protein derived from hepatitis B virus (HBV).

In addition, the vaccine composition may be for preventing infection caused by a pathogen selected from the group consisting of human immunodeficiency virus (HIV), hepatitis B virus (HBV), and *Mycobacterium tuberculosis.*

In addition, in an aspect, the vaccine composition may be for preventing at least one disease selected from the group consisting of liver diseases, acquired immune deficiency syndrome (AIDS), and tuberculosis.

The acquired immune deficiency syndrome (AIDS) may be caused by HIV-1 infection, and the liver disease may be caused by HBV infection, and specifically, may be at least one selected from the group consisting of hepatitis, cirrhosis, and liver cancer, and more specifically, the liver disease may be developed from hepatitis B. In addition, the tuberculosis may be eye tuberculosis, skin tuberculosis, adrenal tuberculosis, kidney tuberculosis, epididymal tuberculosis, lymphatic tuberculosis, laryngeal tuberculosis, middle ear tuberculosis, intestinal tuberculosis, multidrug-resistant tuberculosis, pulmonary tuberculosis, gallbladder tuberculosis, bone tuberculosis, throat tuberculosis, lymph gland tuberculosis, breast tuberculosis, or spinal tuberculosis. In addition, the tuberculosis may be caused by K strain, which is a Korean type of highly pathogenic *Mycobacterium tuberculosis*, or Beijing tuberculosis strain.

Still another aspect provides a method of enhancing immunity including administering a polypeptide including an amino acid sequence of SEQ ID NO: 2 to a subject in need thereof.

Still another aspect provides a method of enhancing immunity including administering the polypeptide consisting of the amino acid sequence of SEQ ID NO: 2 and DNA or an antigen to a subject in need thereof.

The "polypeptide", "DNA", "antigen", "administration", etc. may be within the aforementioned range.

Still another aspect provides a method of preventing at least one disease selected from the group consisting of liver diseases, acquired immune deficiency syndrome (AIDS) and tuberculosis, including administering the polypeptide including the amino acid sequence of SEQ ID NO: 2 to a subject in need thereof.

Still another aspect provides a method of preventing at least one disease selected from the group consisting of liver diseases, acquired immune deficiency syndrome (AIDS) and tuberculosis, including administering the polypeptide consisting of the amino acid sequence of SEQ ID NO: 2 and DNA or an antigen to a subject in need thereof.

The "polypeptide", "DNA", "antigen", "administration", "liver disease", "AIDS", "tuberculosis", etc. may be within the aforementioned range.

Advantageous Effects of Disclosure

A hepatitis B virus-derived polypeptide according to an aspect is effective in enhancing immunity through co-administration with vaccines as a single immune adjuvant, and in particular, when co-administered with another immune adjuvant, may exhibit a more remarkable immunity enhancement effect.

Furthermore, the polypeptide is a single molecule having only 6 amino acids, is not cytotoxic, and has excellent in vivo stability.

Figure 6A:
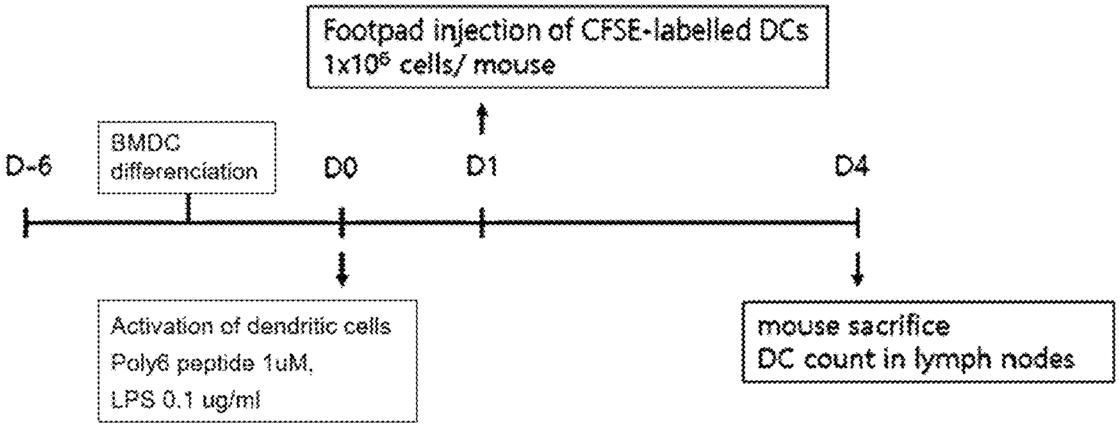
Figure 6B:
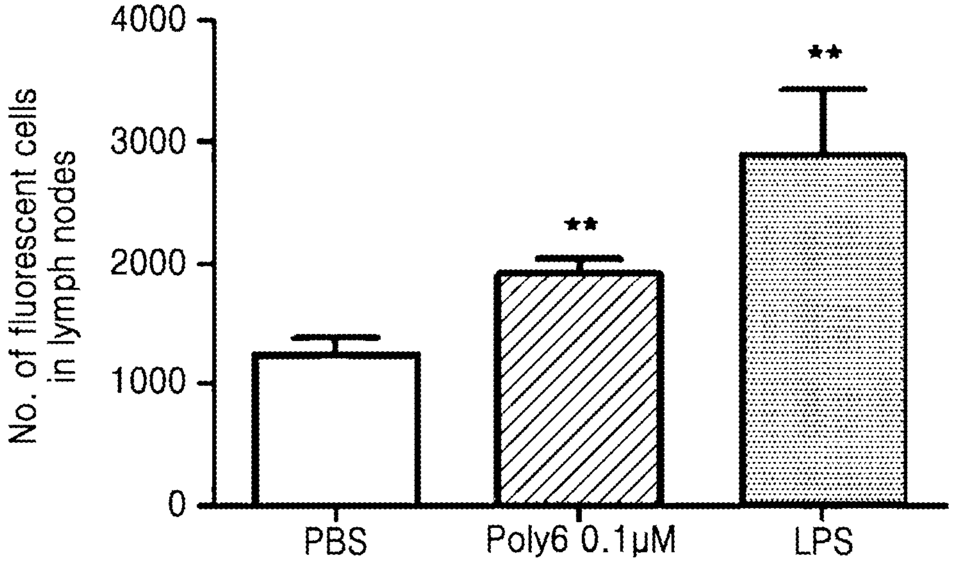

(A) of FIG. 6 is a diagram confirming numbers of dendritic cells in the lymph nodes of mice, 3 days after injecting dendritic cells activated by Poly6 peptides into the mice. (B) is a diagram showing that dendritic cells activated by treatment with 0.1 μM of Poly6 and 0.1 μg/ml of lipopolysaccharide (LPS) have an ability to migrate to the lymph nodes on their own in the body of a mouse, compared to dendritic cells without any treatment (statistical significance is tested by Student-t-test, *, P<0.05; , P<0.01; *, P<0.001).

Figure 7:
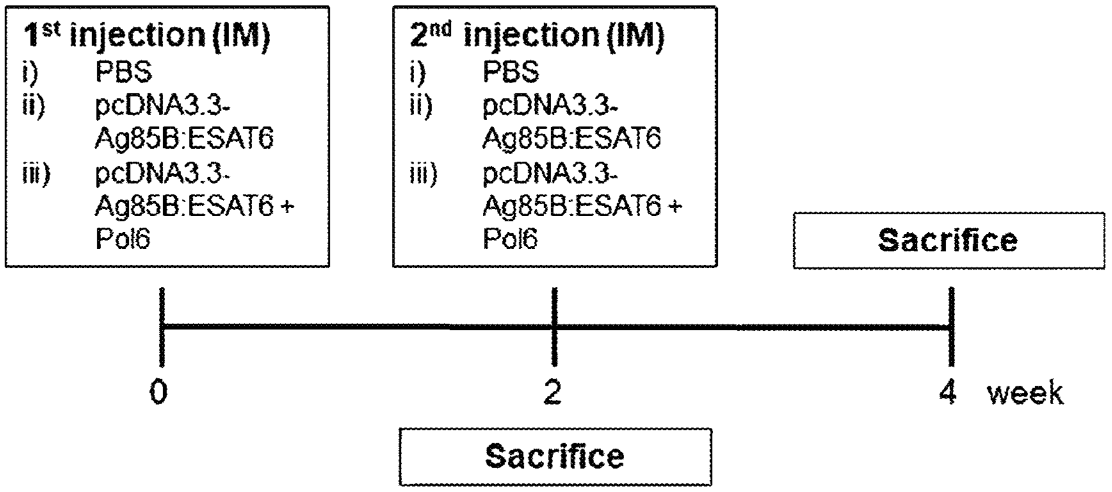

FIG. 7 is a diagram showing a mouse intramuscular (IM) immunization schedule using a combination of pcDNA3.3-Ag85B:ESAT6 DNA and Poly6.

Figure 8A:
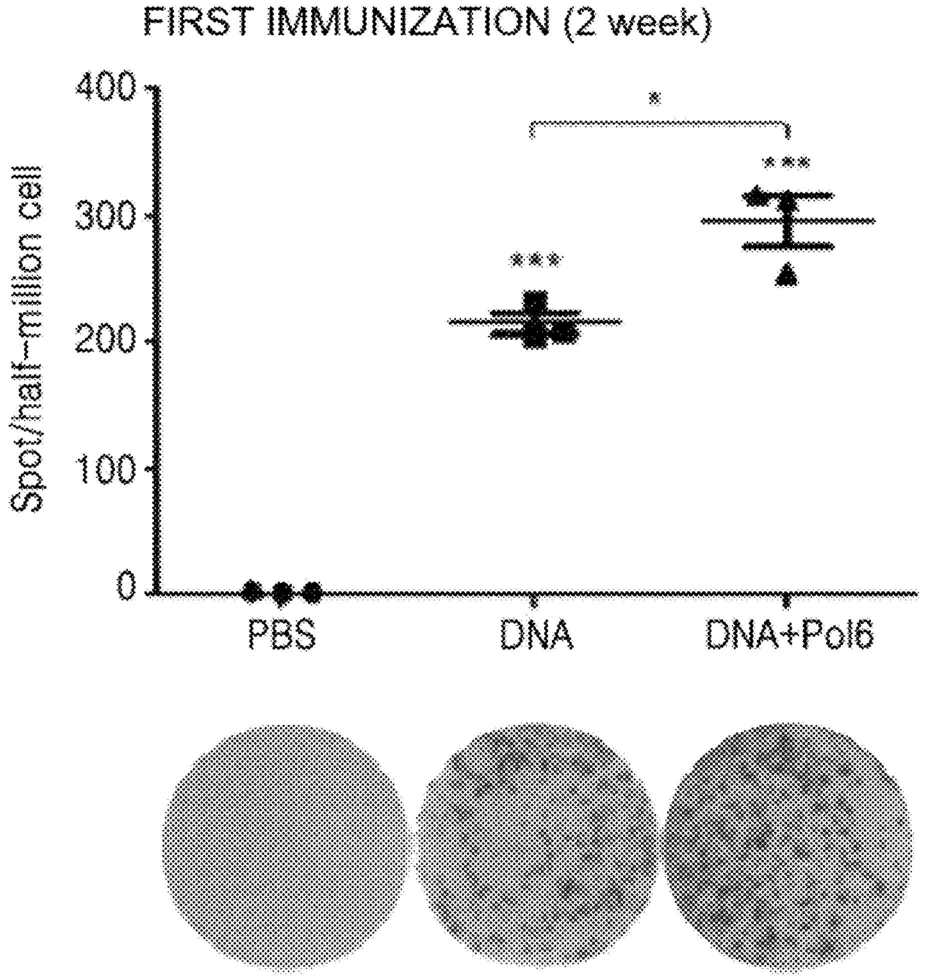
Figure 8B:
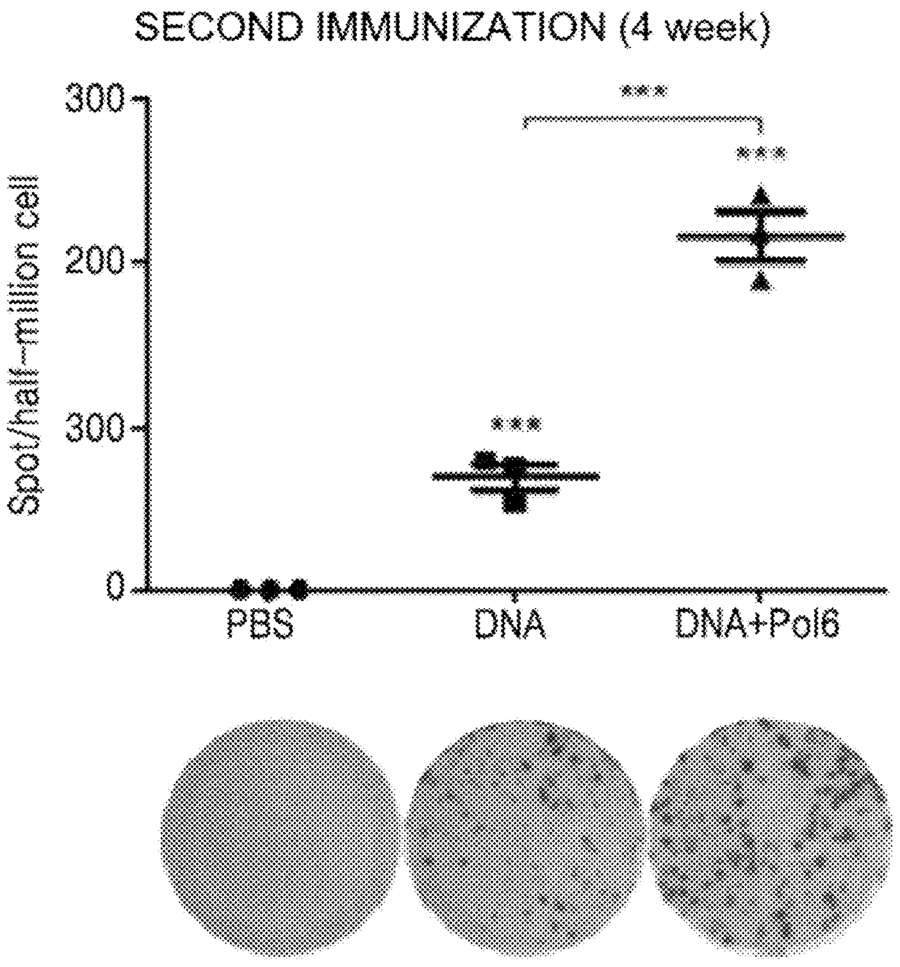

FIG. 8 is a diagram showing data obtained by measuring amounts of IFN-γ expressed in cells by using ELISPOT when splenocytes are stimulated with Ag85B, wherein the splenocytes are obtained by immunizing with a combination of pcDNA3.3-Ag85B:ESAT6 DNA and Poly6 (statistical significance is tested by Student-t-test, *, P<0.05; ***, P<0.001).

Figure 9:
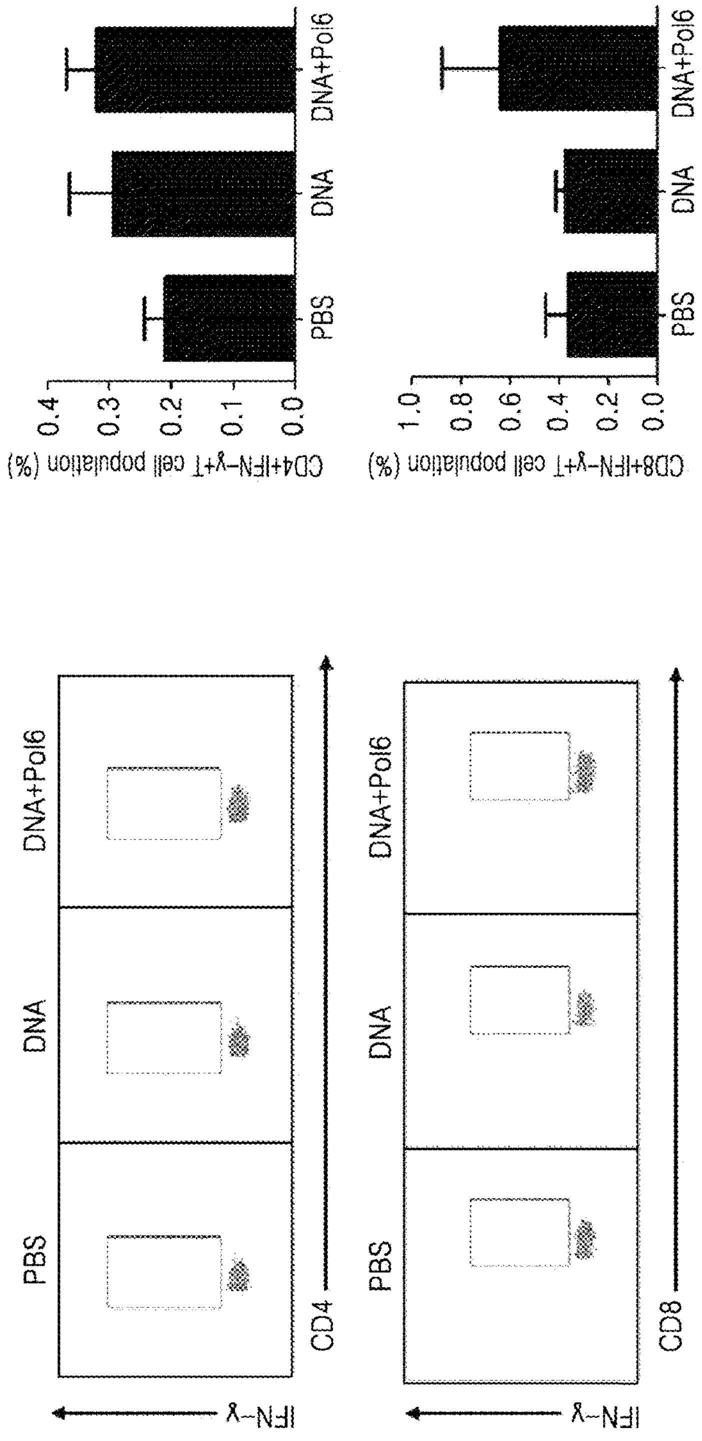

FIG. 9 is a diagram showing data obtained by fluorescence activated cell sorting (FACS) analysis of CD4 and CD8 T cell populations expressing IFN-γ after stimulating splenocytes with Ag85B, wherein the splenocytes are obtained by immunizing once (at week 2) with a combination of pcDNA3.3-Ag85B: ESAT6 DNA and Poly6.

Figure 10:
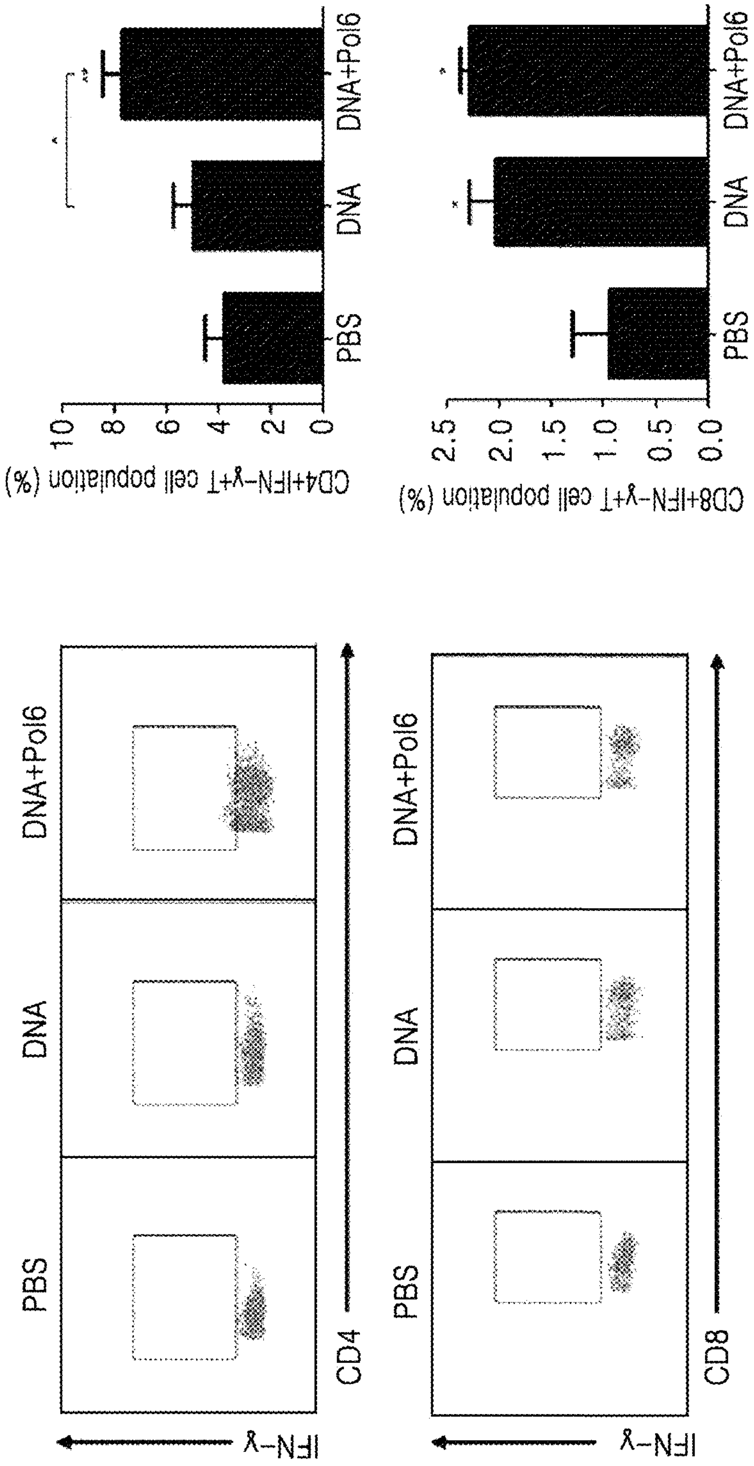

FIG. 10 is a diagram showing data obtained by FACS analysis of CD4 and CD8 T cell populations expressing IFN-γ after stimulating splenocytes with Ag85B, wherein the splenocytes are obtained by immunizing for the second time (at week 4) with the combination of pcDNA3.3-Ag85B:ESAT6 DNA and Poly6 (statistical significance is tested by Student-t-test, *, P<0.05; **, P<0.01).

Figure 11A:
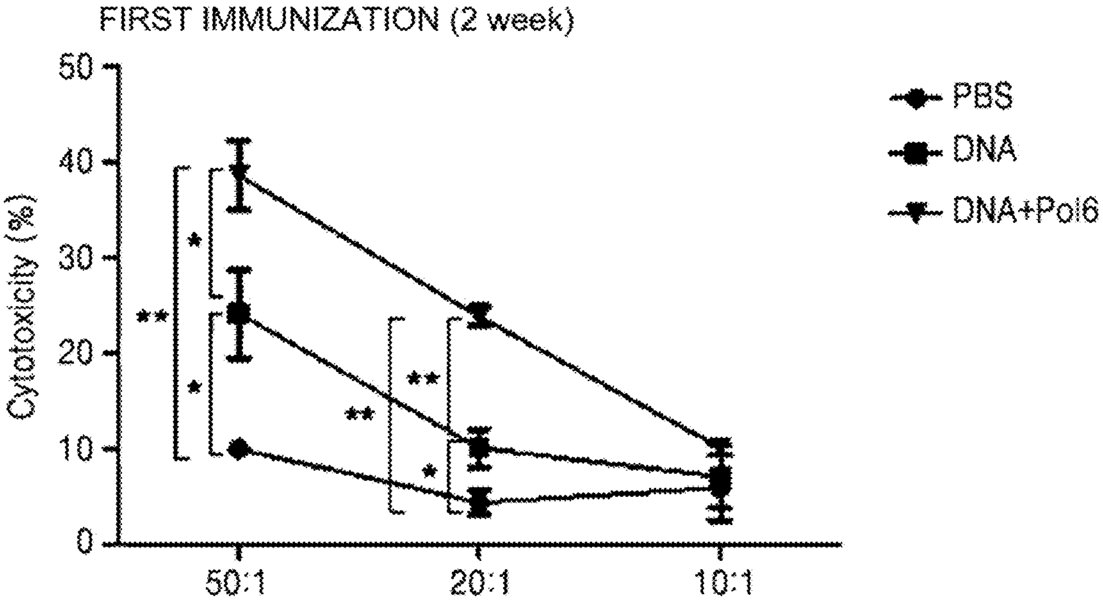
Figure 11B:
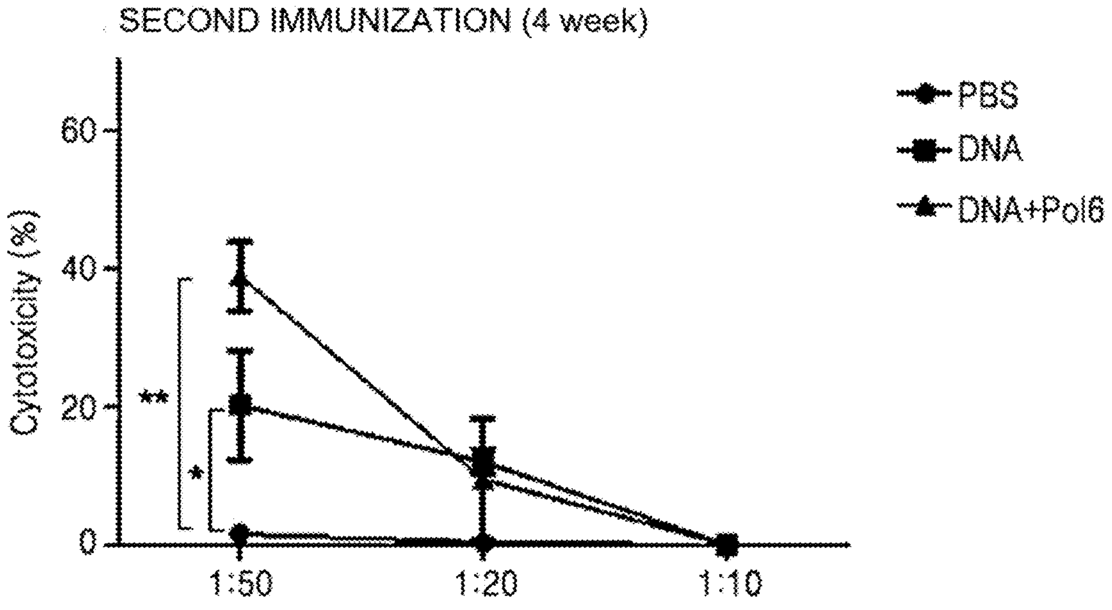

FIG. 11 is a diagram showing results of cytotoxic T lymphocyte (CTL) responses induced by a group immunized with a combination of pcDNA3.3-Ag85B:ESAT6 DNA and Poly6 once and twice ((A) first immunization, (B) second immunization, statistical significance is tested by Student-t-test, *, P<0.05; **, P<0.01).

Figure 12:
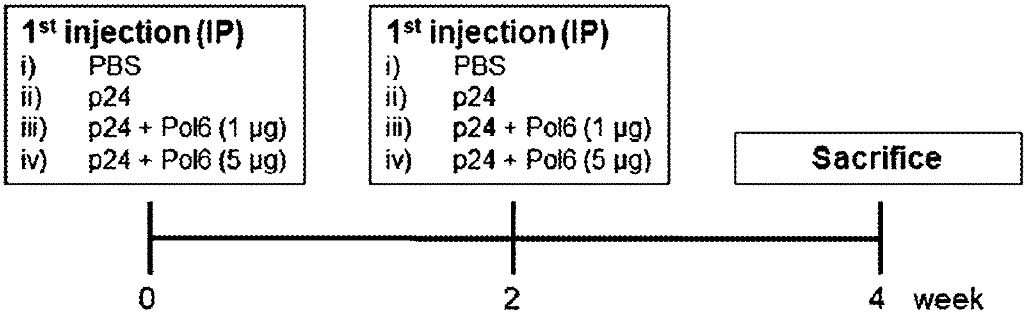

FIG. 12 is a diagram showing a mouse intraperitoneal (IP) immunization schedule using a combination of p24 proteins and Poly6 (at each concentration, 1 μg or 5 μg).

Figure 13:
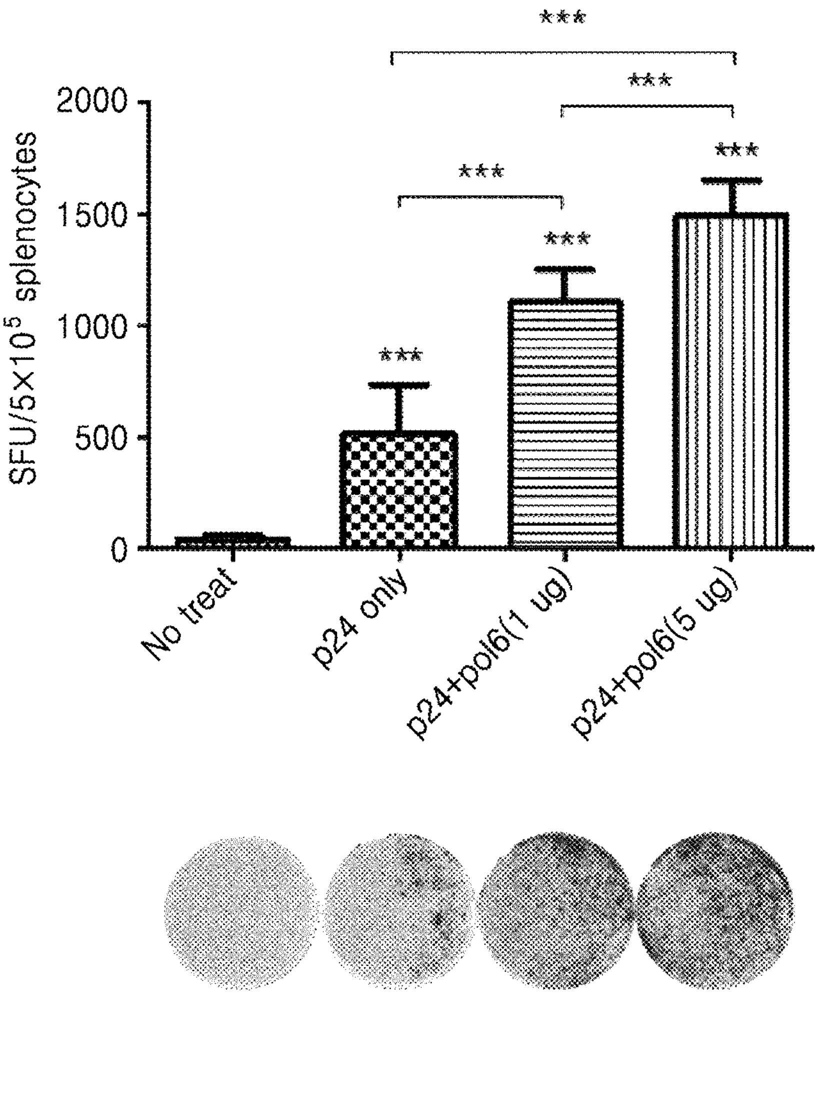
Figure 14A:
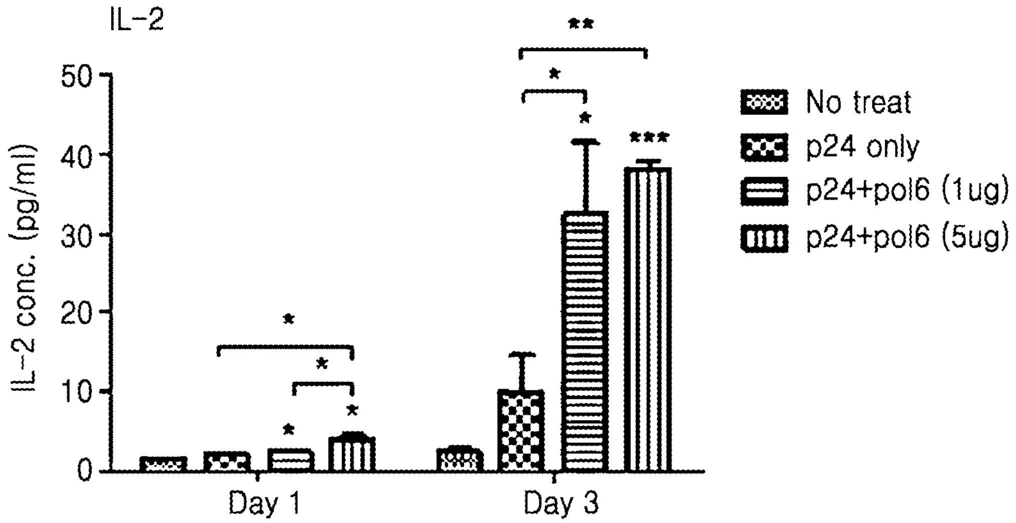
Figure 14B:
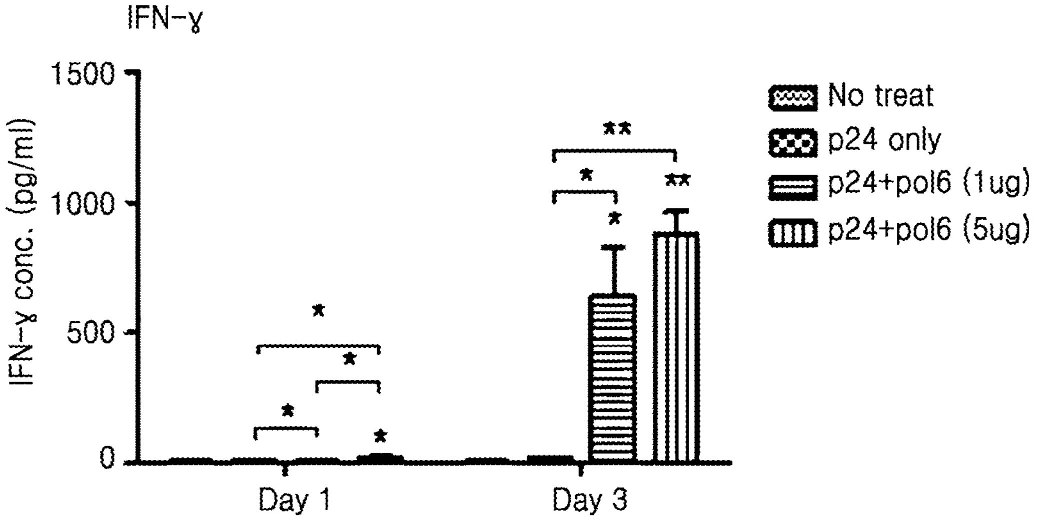
Figure 14C:
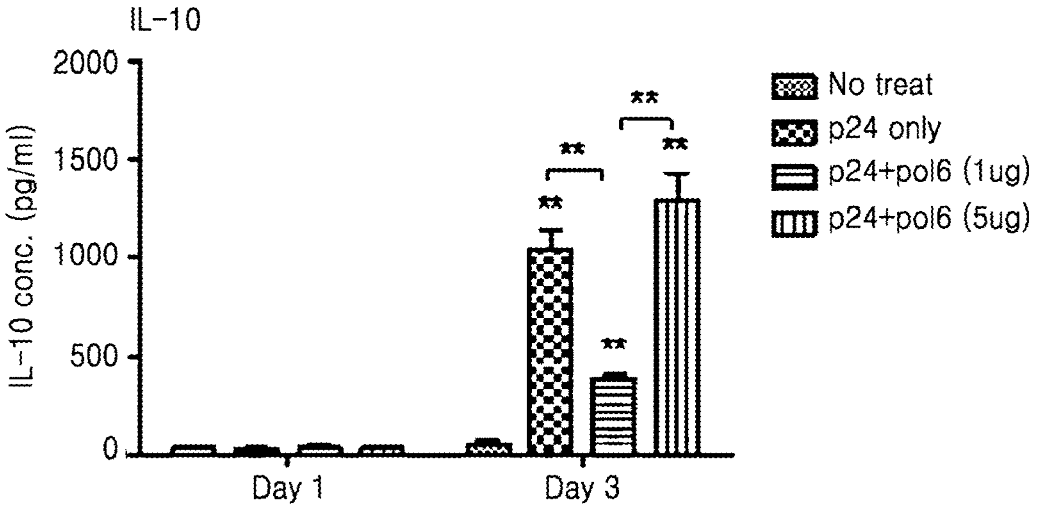
Figure 14D:
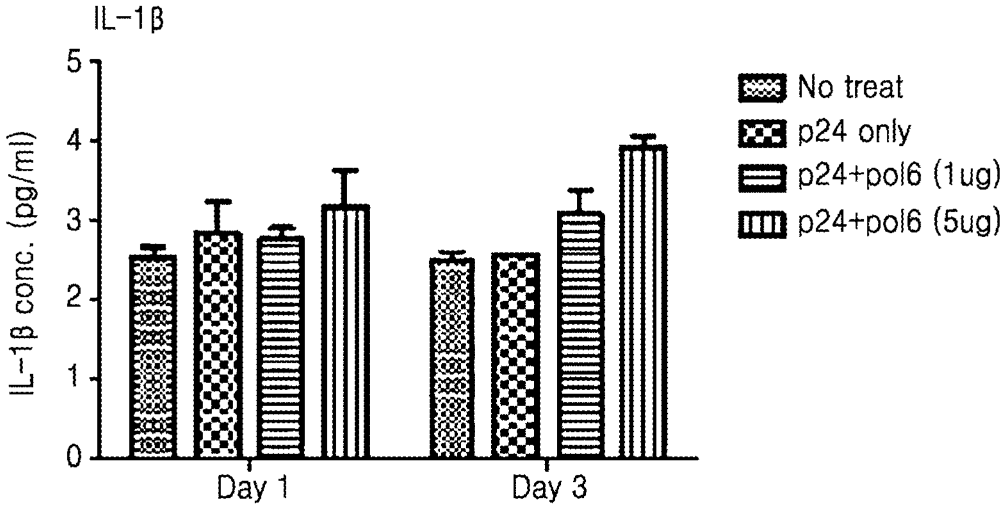
Figure 14E:
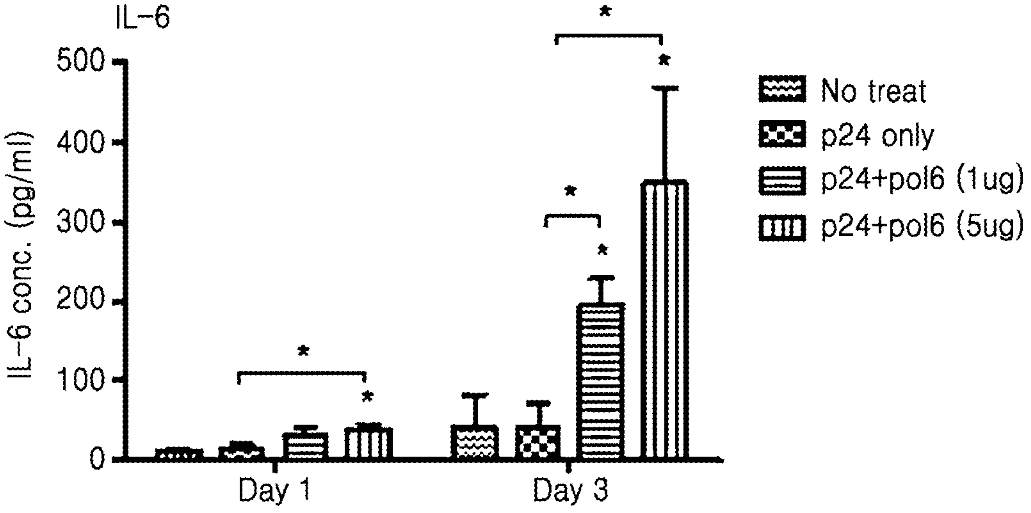
Figure 14F:
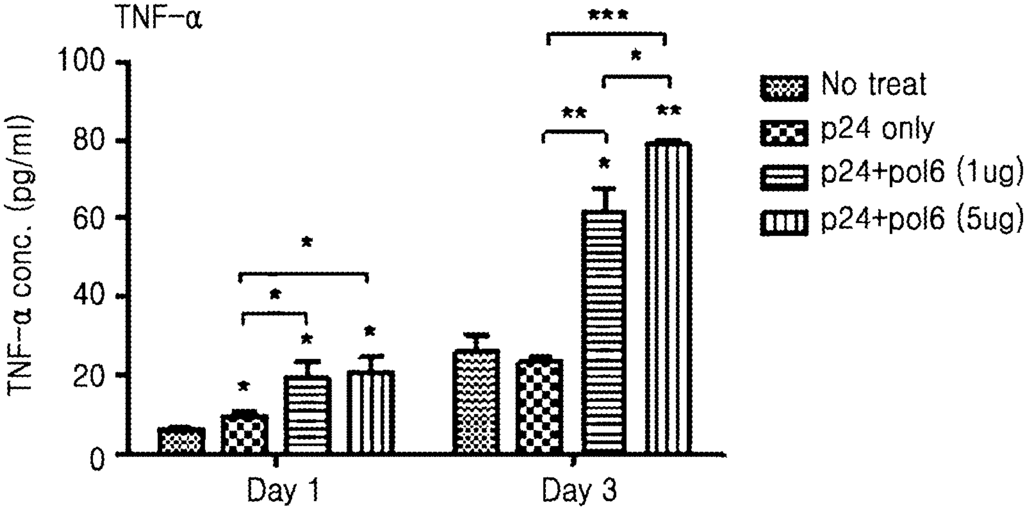

FIG. 13 is a diagram showing data obtained by measuring amounts of IFN-γ expressed in cells by using ELISPOT when splenocytes of mice immunized (IP route) with a combination of p24 proteins and Poly6 (1 μg or 5 μg) are stimulated with p24 (statistical significance is tested by Student-t-test, ***, P<0.001).

FIG. 14 is a diagram showing results of confirming cytokines (A) IL-2 (B) IFN-γ, (C) IL-10, (D) IL-13, (E) IL-6, and (F) TNF-α expressed in cell culture medium by using ELISA, when splenocytes of mice immunized (IP route) with a combination of p24 proteins and Poly6 (1 μg or 5 μg) are stimulated with p24, (statistical significance is tested by Student-t-test, *, P<0.05; , P<0.01; *, P<0.001).

Figure 15A:
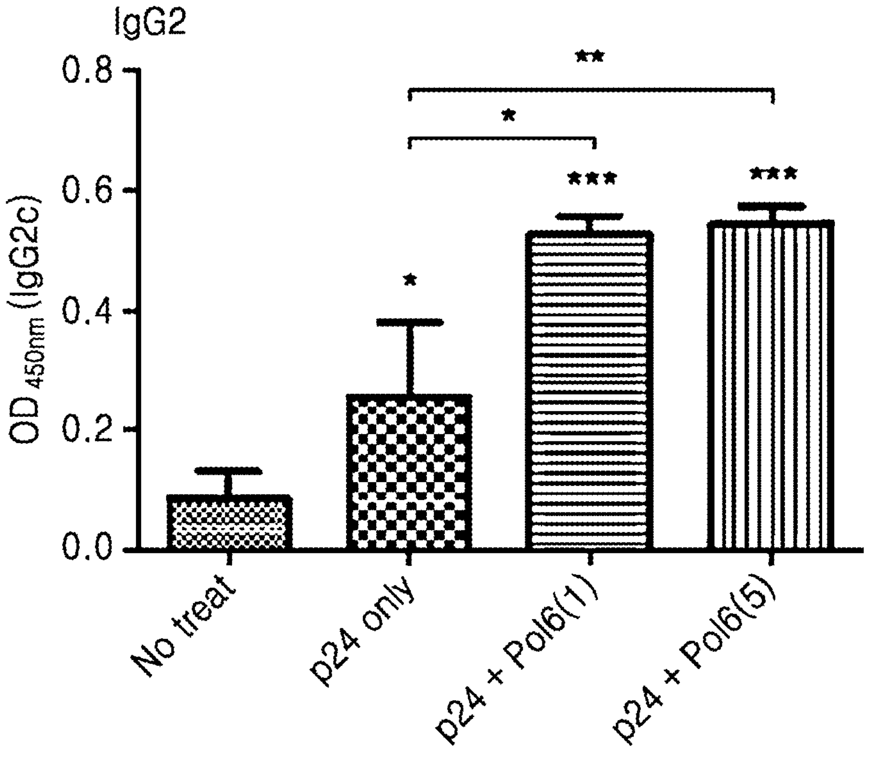
Figure 15B:
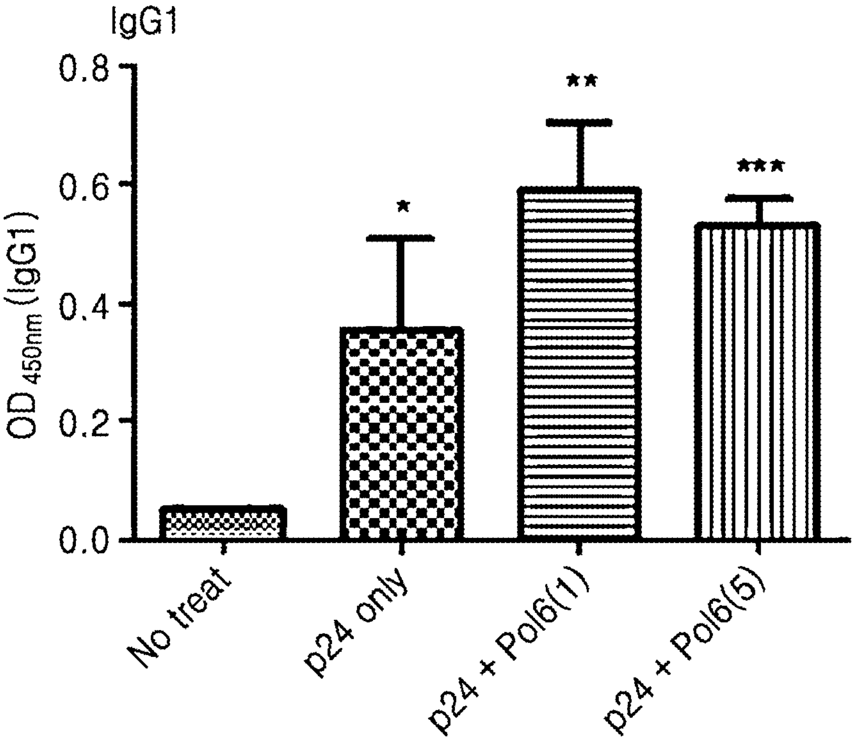
Figure 15C:
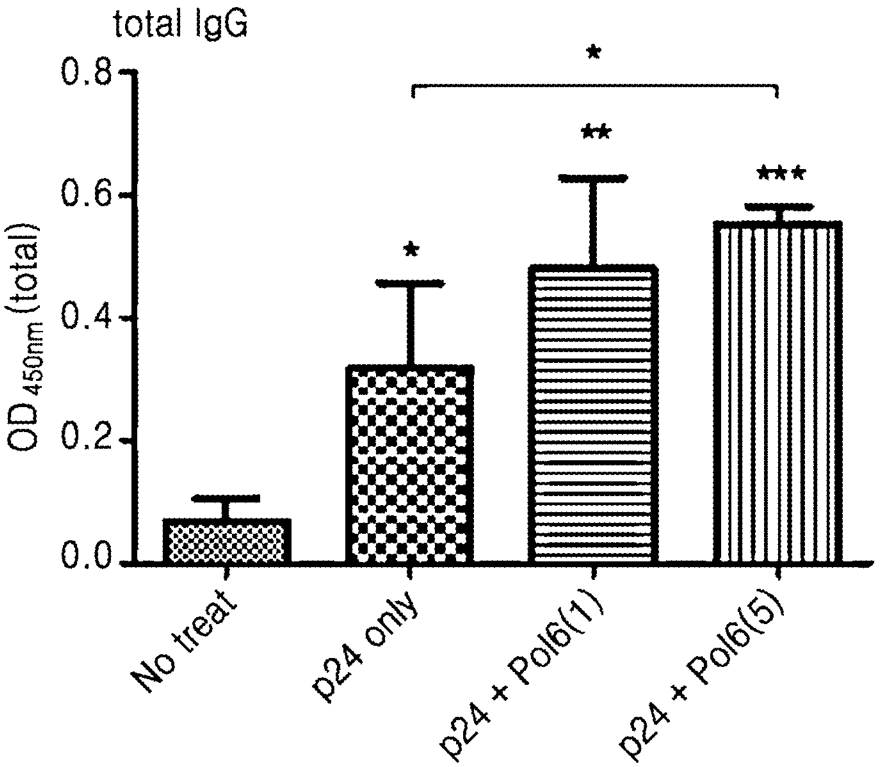

FIG. 15 is a diagram showing results of confirming expression of p24-specific (A) IgG2, (B) IgG1, and (C) total IgG in serum of mice immunized (IP route) with a combination (1 or 5 μg) of p24 proteins and Poly6 by using ELISA, (statistical significance is tested by Student-t-test, *, P<0.05; , P<0.01; *, P<0.001).

Figure 16:
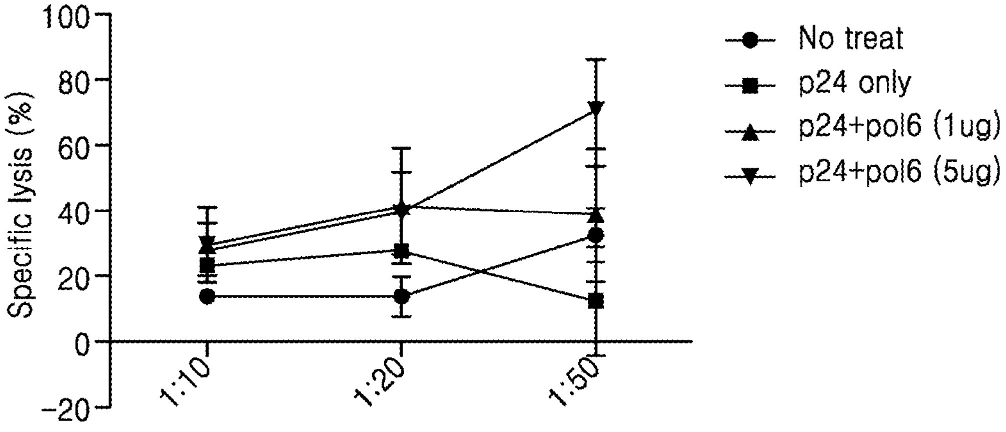

FIG. 16 is a diagram showing results of CTL responses induced by each immunization group.

Figure 17:
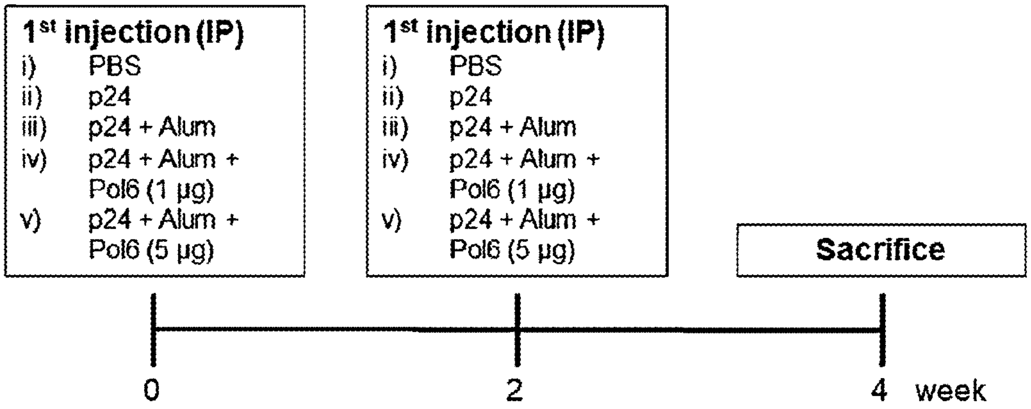

FIG. 17 is a diagram showing a mouse IP immunization schedule by using a combination of p24 proteins, Alum and Poly6 (at each concentration, 1 μg or 5 μg).

Figure 18:
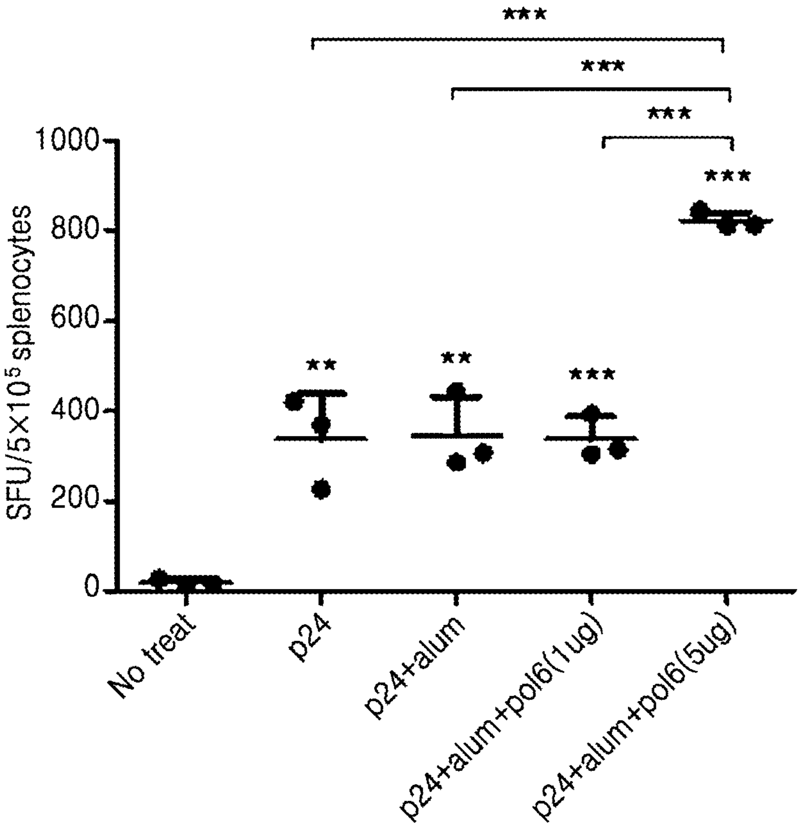
Figure 19A:
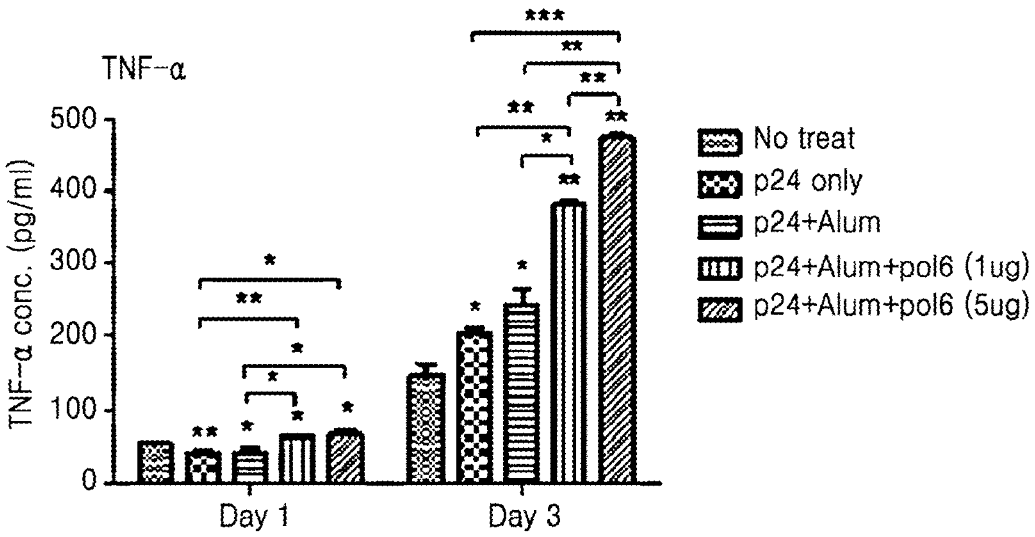
Figure 19B:
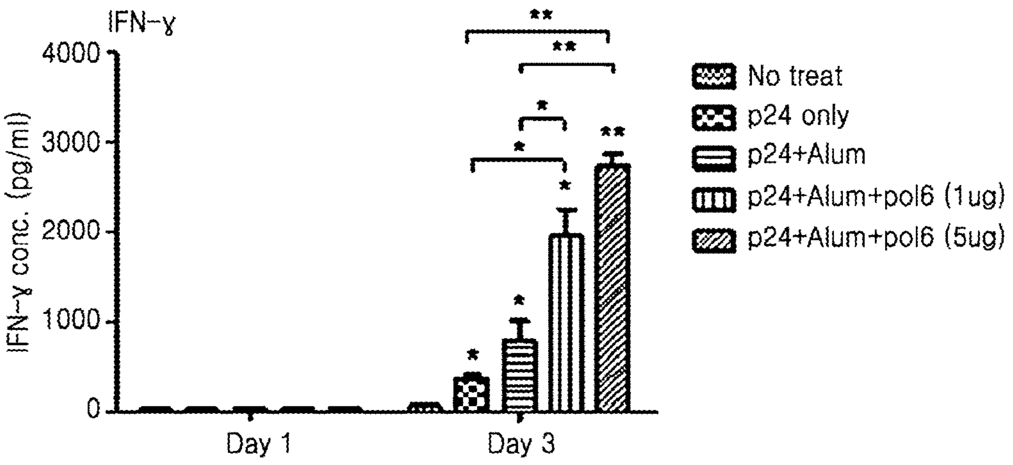
Figure 19C:
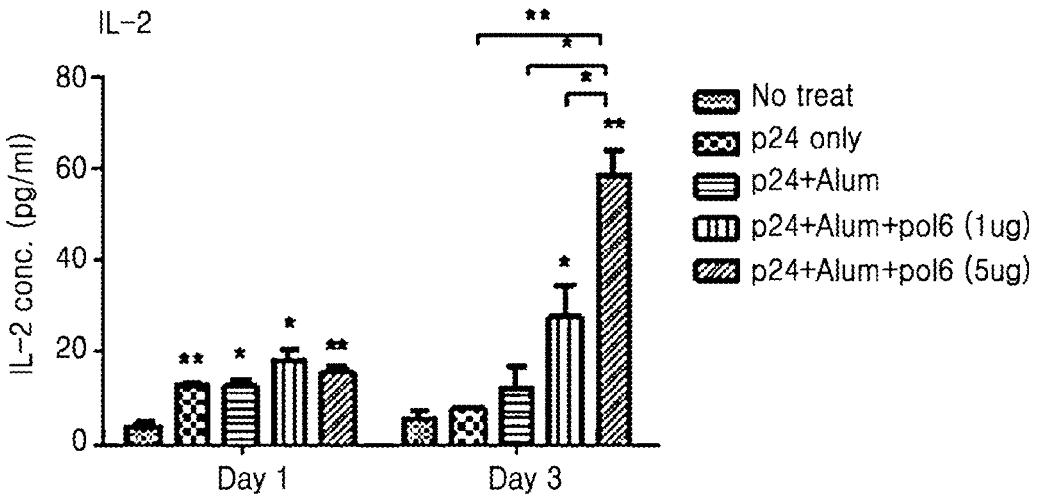
Figure 19D:
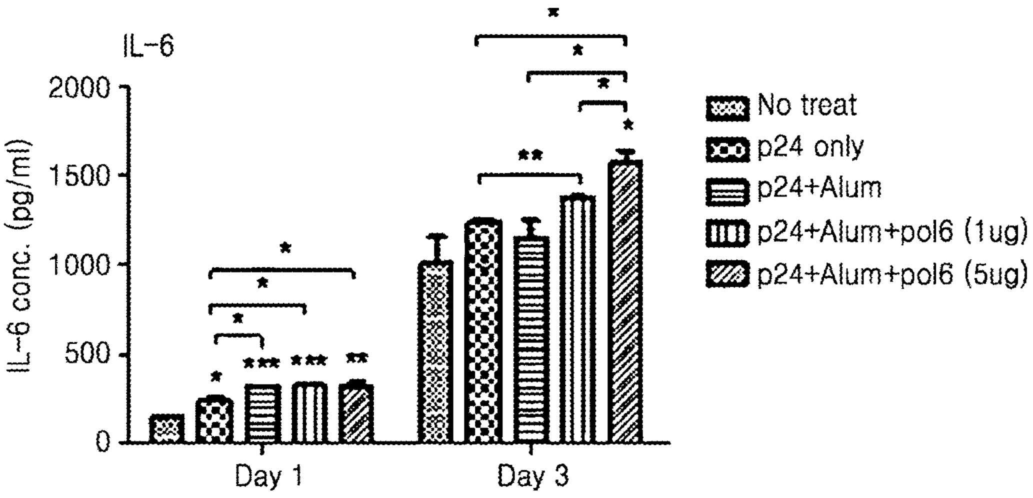
Figure 19E:
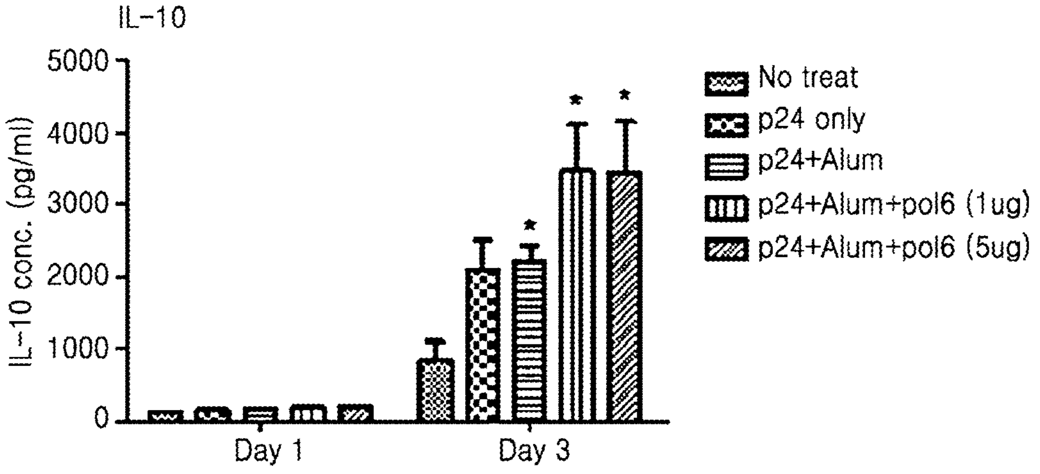

FIG. 18 is a diagram showing data obtained by measuring amounts of IFN-γ expressed in cells by using ELISPOT when splenocytes of mice immunized (IP route) with a combination of p24 proteins, Alum, and Poly6 (1 μg or 5 μg) are stimulated with p24 (statistical significance is tested by Student-t-test, , P<0.01; *, P<0.001).

FIG. 19 is a diagram showing results of confirming cytokines (A) TNF-α (B) IFN-γ, (C) IL-2 (D) IL-6, (E) IL-10, expressed in cell culture medium by using ELISA, when splenocytes of mice immunized (IP route) with a combination of p24 proteins, Alum, and Poly6 (1 μg or 5 μg) are stimulated with p24, (statistical significance is tested by Student-t-test, *, P<0.05; , P<0.01; *, P<0.001).

Figure 20A:
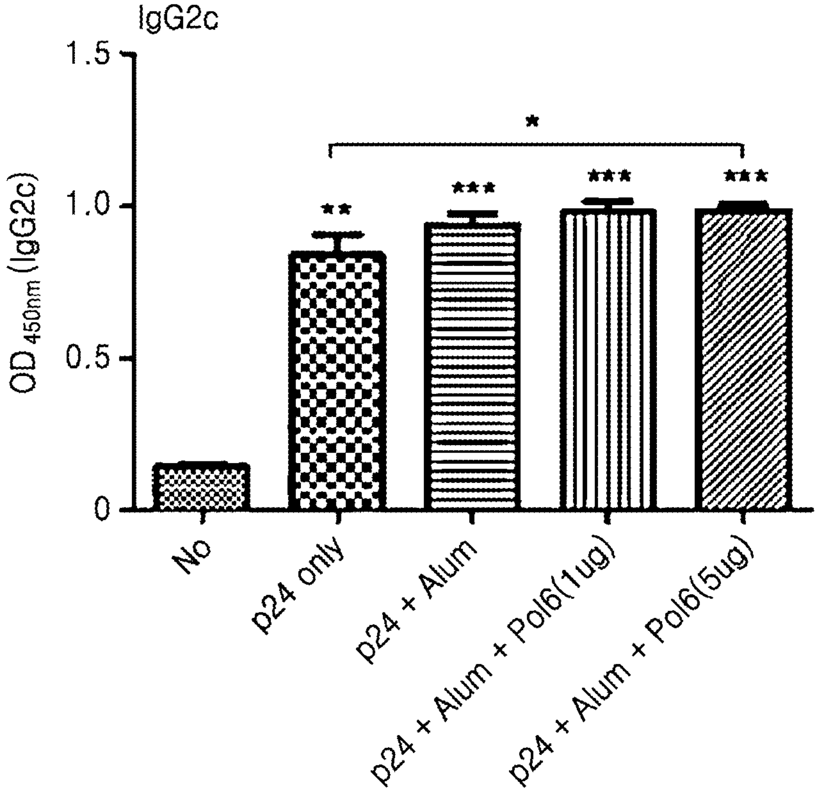
Figure 20B:
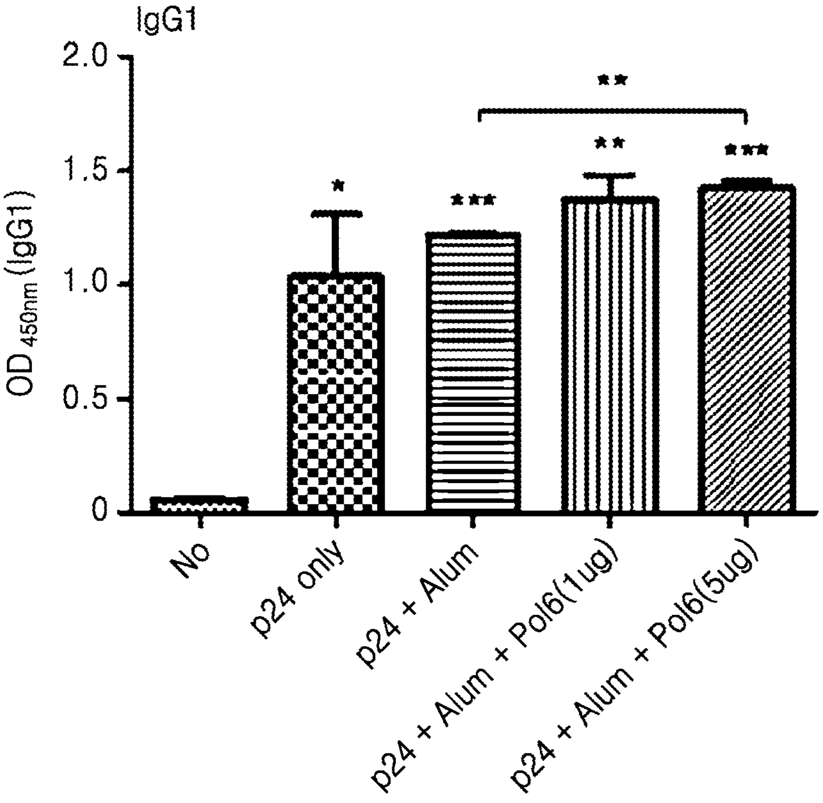
Figure 20C:
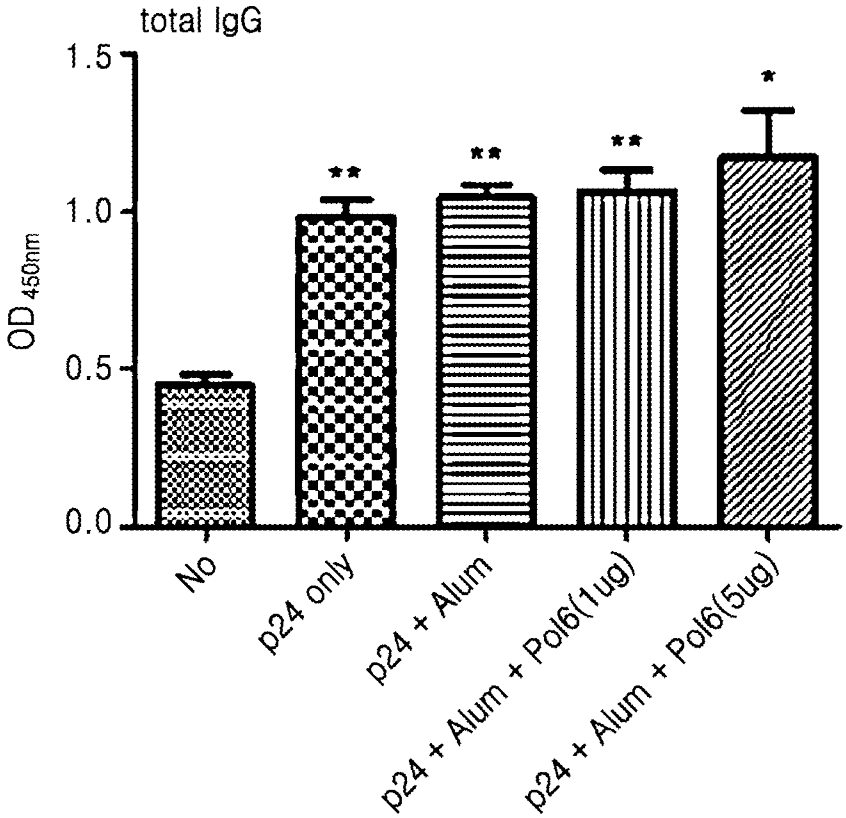

FIG. 20 is a diagram showing results of confirming expression of p24-specific (A) IgG2, (B) IgG1, and (C) total IgG in serum of mice immunized (IP route) with a combination (1 or 5 μg) of p24 proteins, Alum, and Poly6 by using ELISA, (statistical significance is tested by Student-t-test, *, P<0.05; , P<0.01; *, P<0.001).

Figure 21:
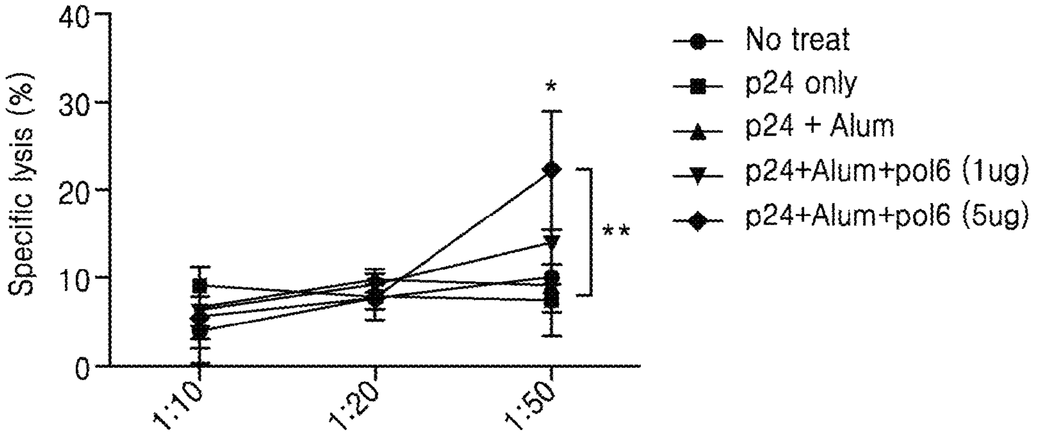

FIG. 21 is a diagram showing results of CTL responses induced by each immunization group (statistical significance is tested by Student-t-test, *, P<0.05; **, P<0.01).

Figure 22:
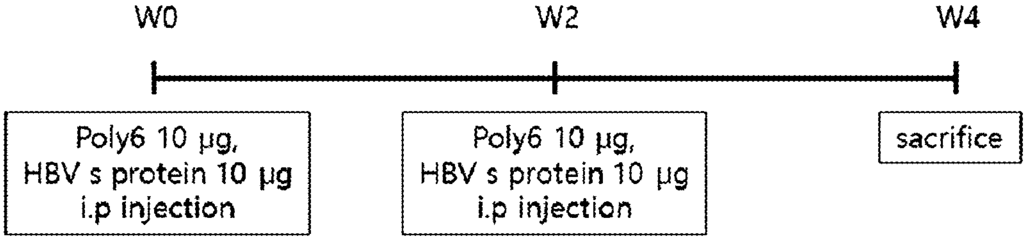

FIG. 22 is a diagram showing a mouse immunization schedule by using a combination of Poly6 and HBV S proteins.

Figure 23:
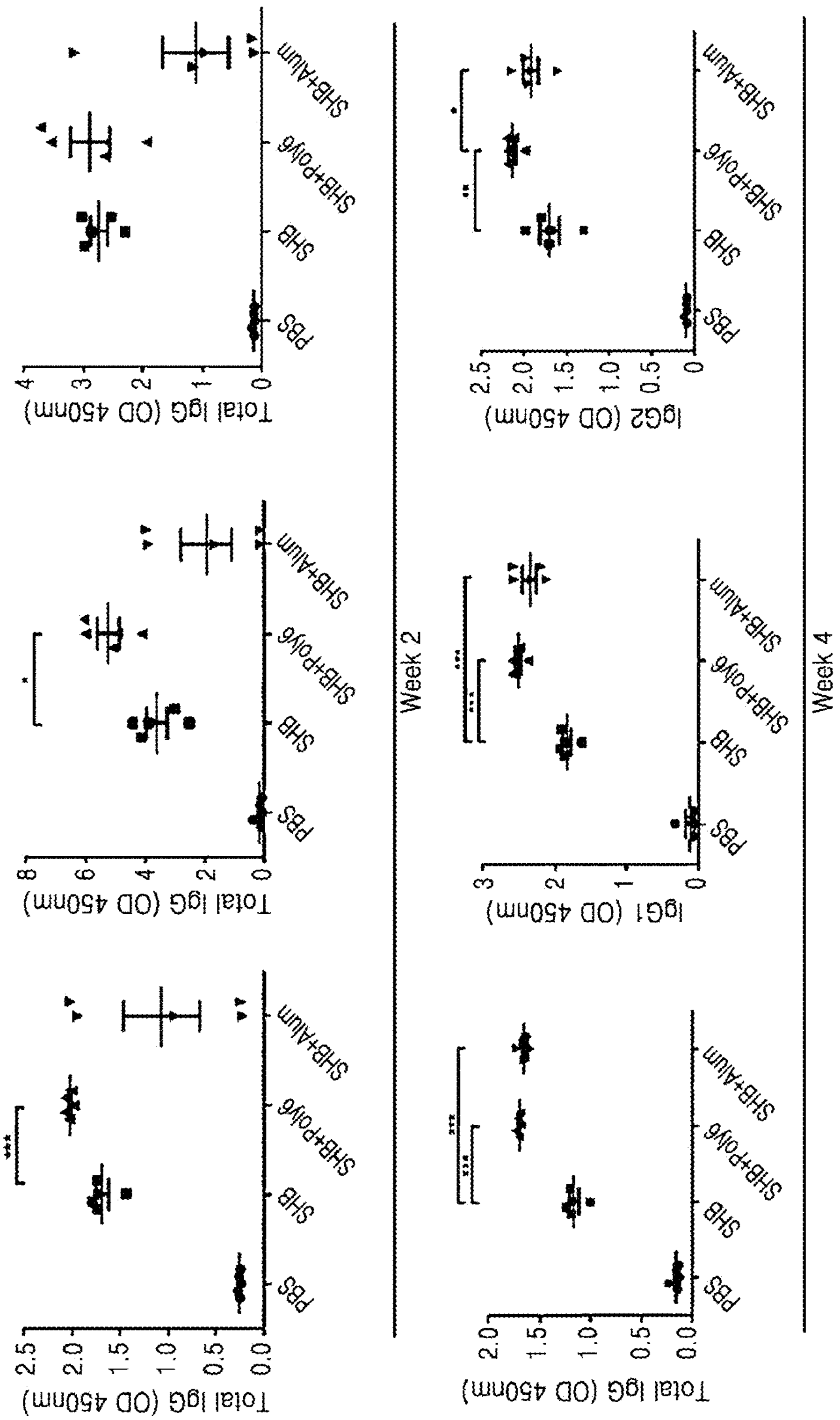

FIG. 23 is a diagram showing results of confirming expression of IgG against S antigens in serum of mice by using ELISA, when the mice are co-immunized with S proteins, Poly6, and Alum (statistical significance is tested by Student-t-test, *, P<0.05; , P<0.01; *, P<0.001).

Figure 24A:
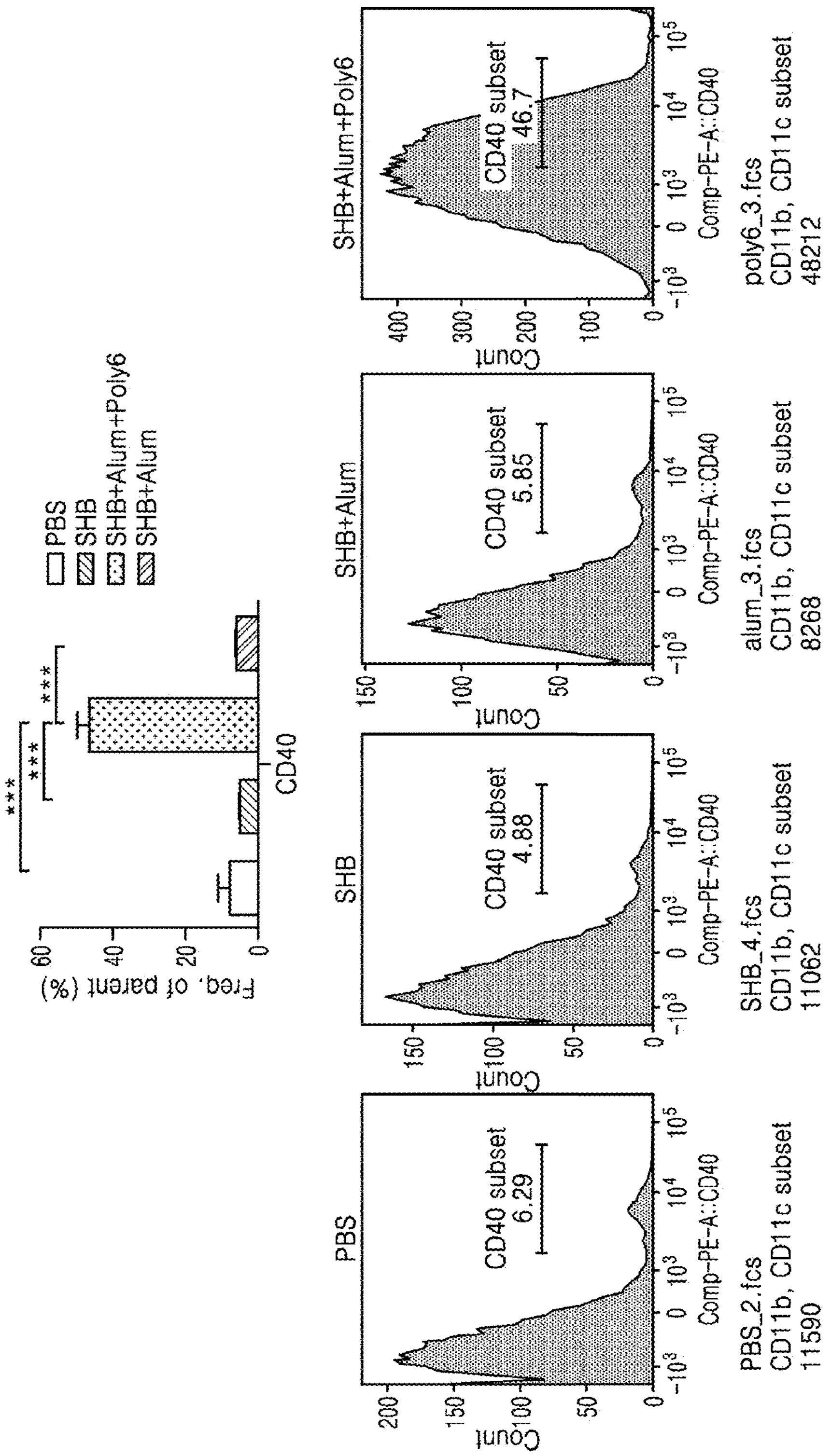
Figure 24B:
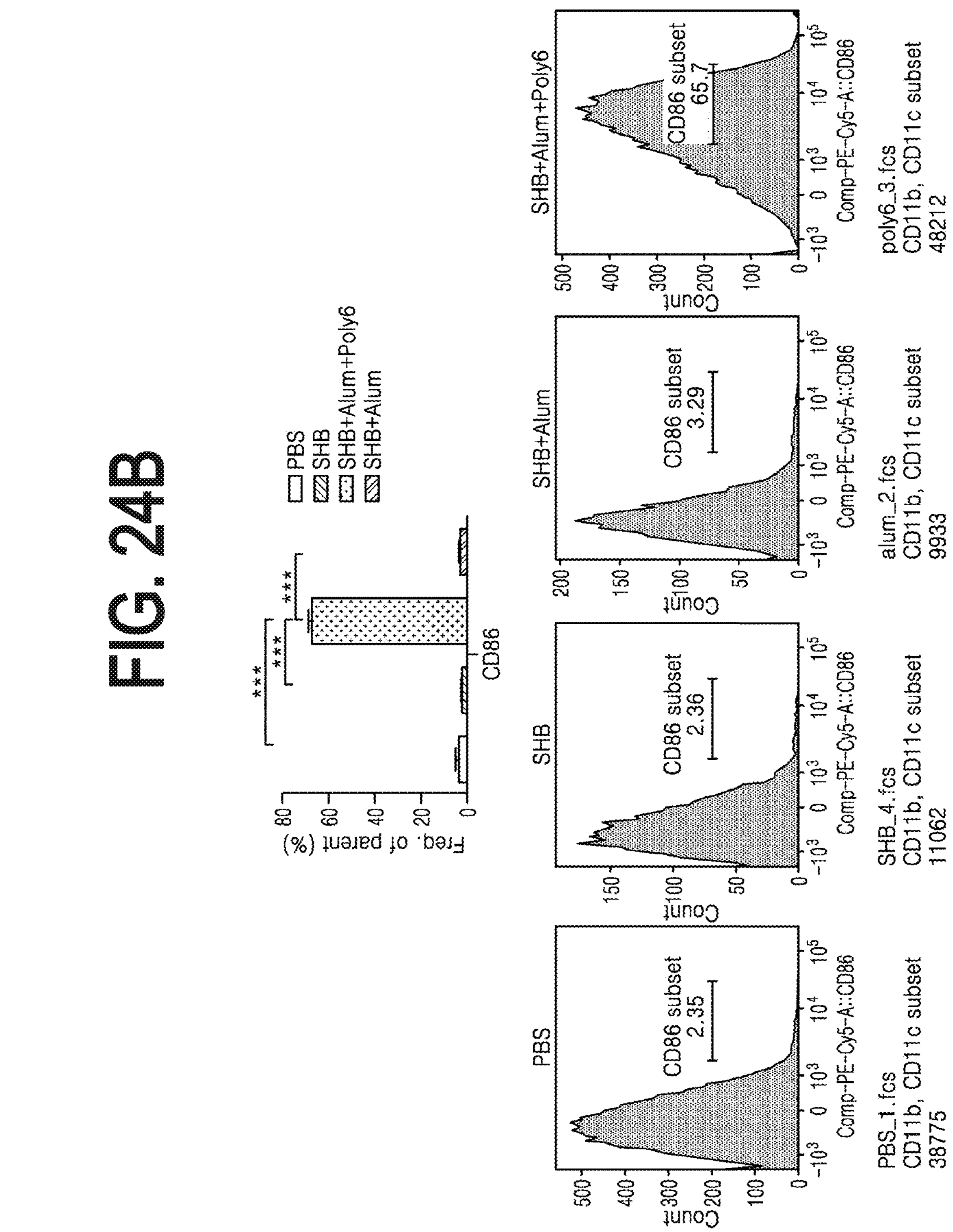

FIG. 24 is a diagram confirming expression of maturation markers (A) CD40, and (B) CD86 of dendritic cells when HBV-derived Poly6 peptides and S proteins are injected into mice (statistical significance is tested by Student-t-test, *, P<0.05; , P<0.01; *, P<0.001).

Figure 25A:
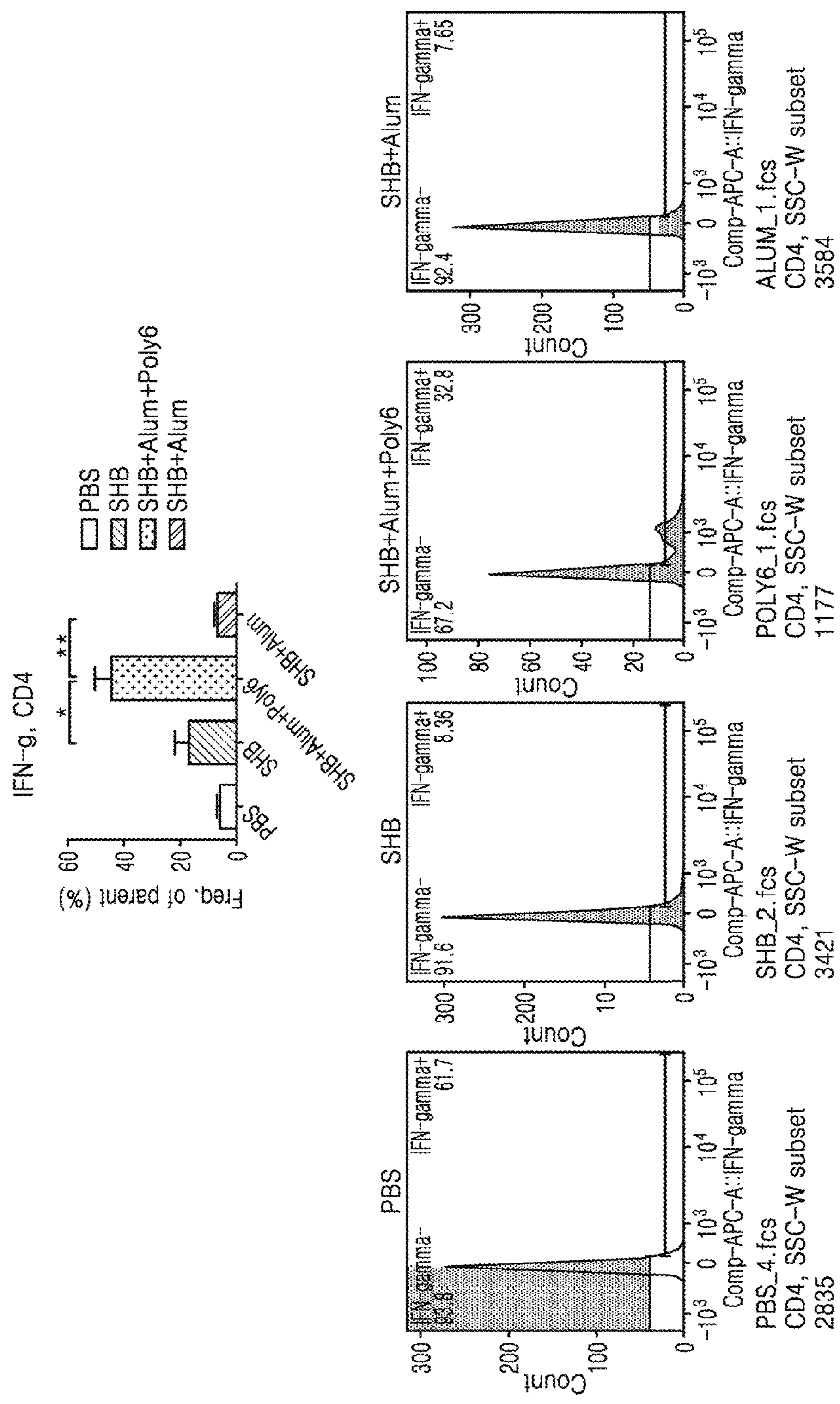
Figure 25B:
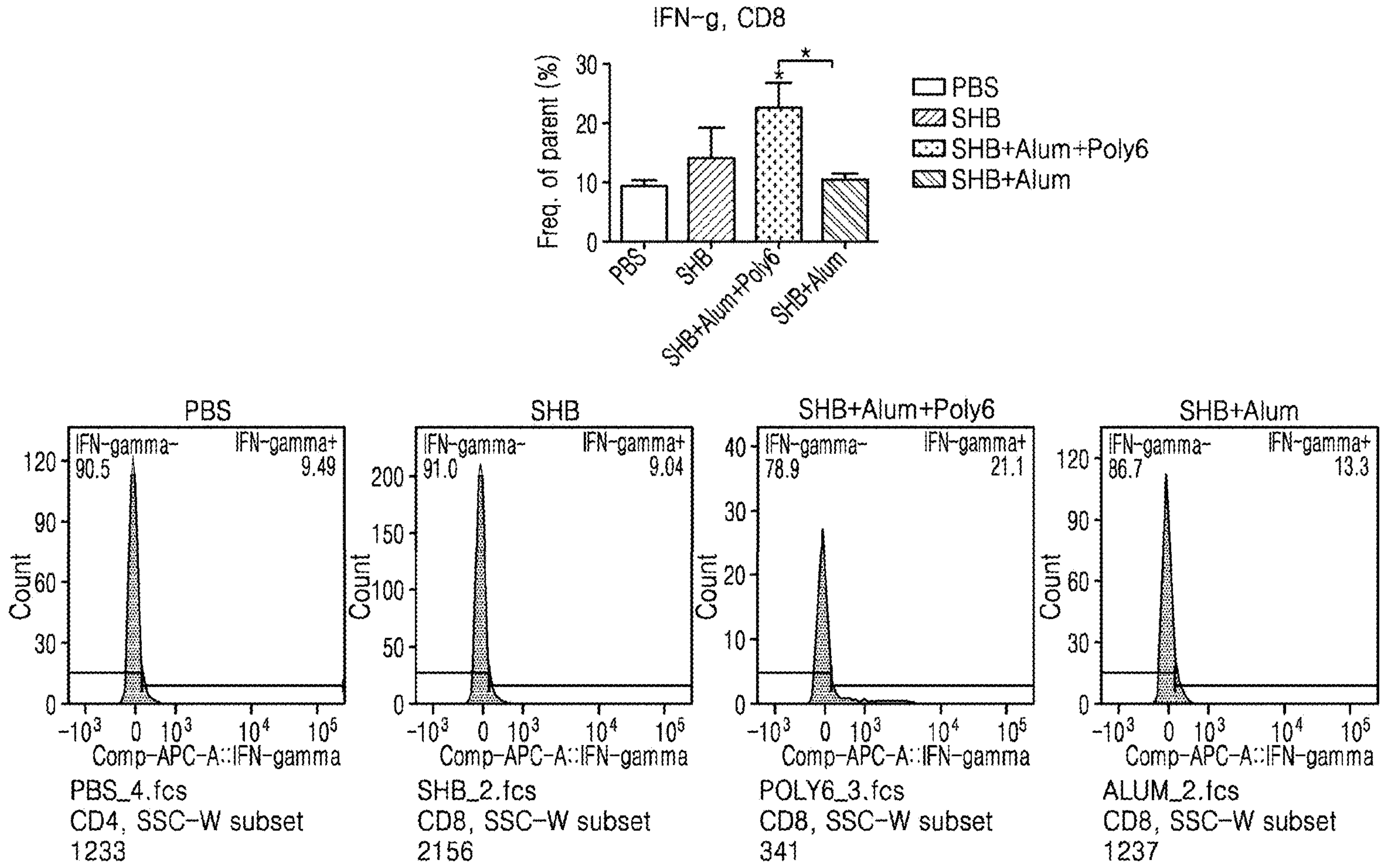

FIG. 25 is a diagram confirming numbers of (A) CD4 T cells, and (B) CD8 T cells secreting IFN-γ from splenocytes, when Poly6 and HBV S proteins are injected into mice in combination (statistical significance is tested by Student-t-test, *, P<0.05; , P<0.01; *, P<0.001).

Figure 26:
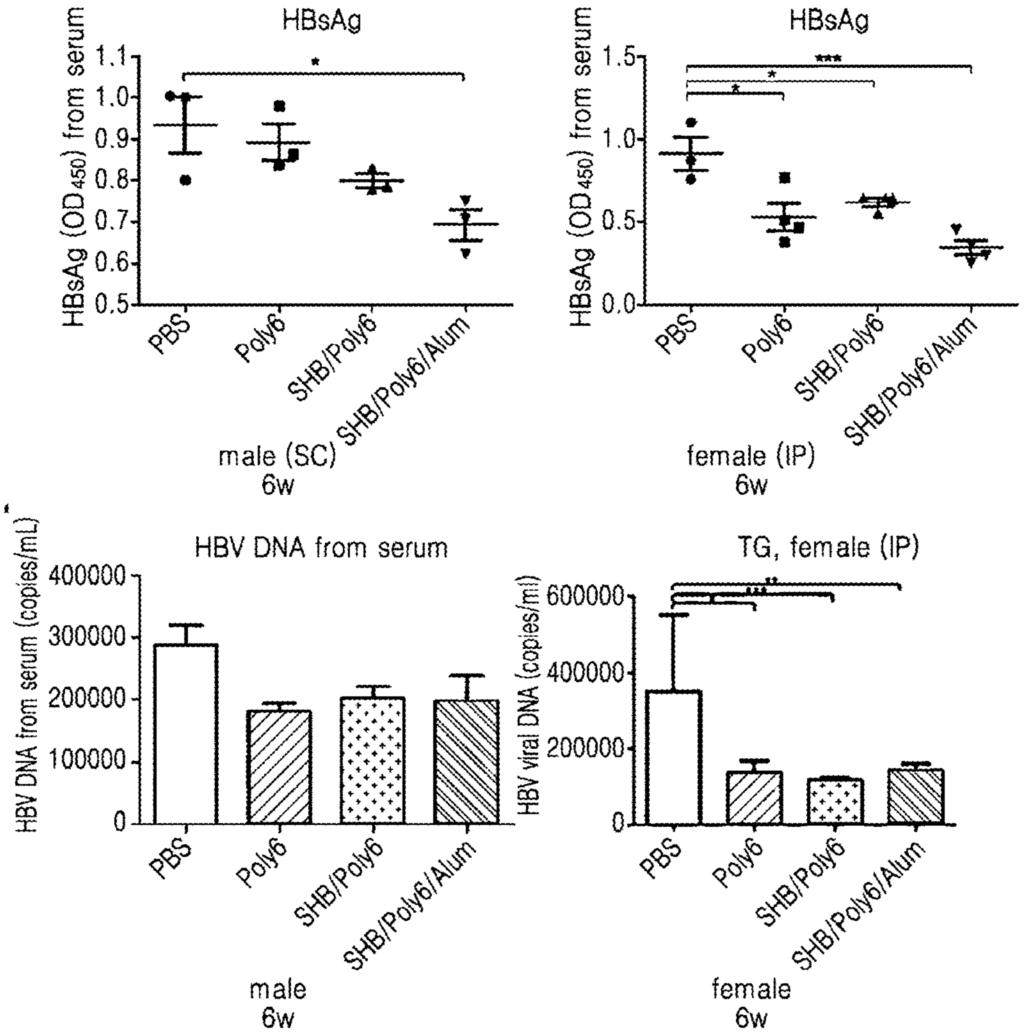

FIG. 26 is a diagram showing results of measuring reduction of HBsAg and HBV DNA in serum when S antigens and Poly6 are co-administered to transgenic (TG) mice.

Figure 27:
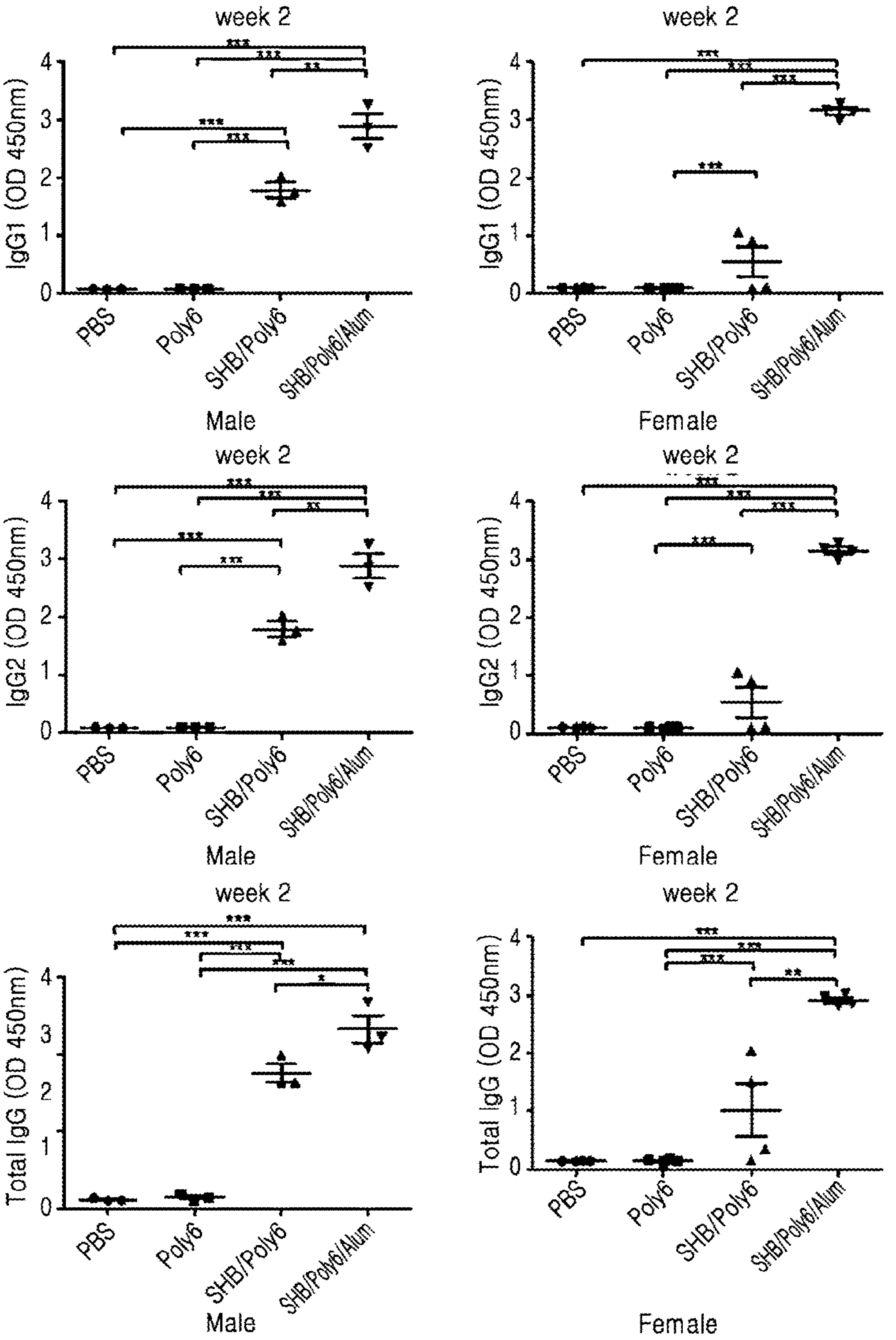

FIG. 27 is a diagram confirming an increase of IgG specific for HBsAg when S antigens and Poly6 are co-administered to TG mice.

Figure 28A:
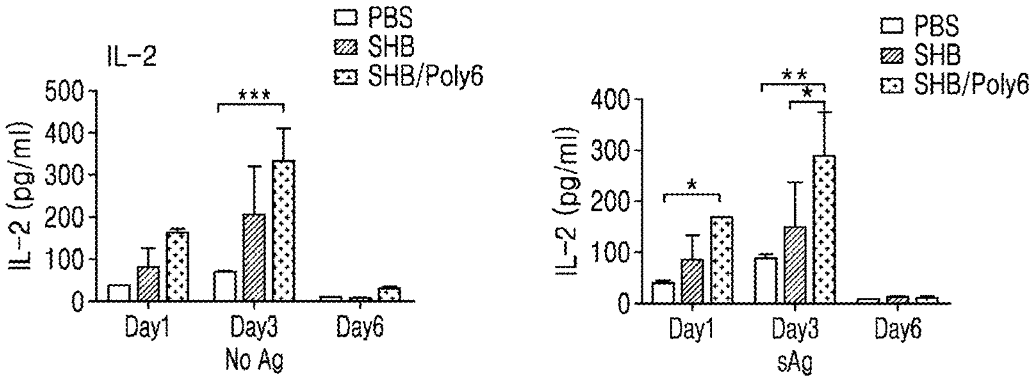
Figure 28B:
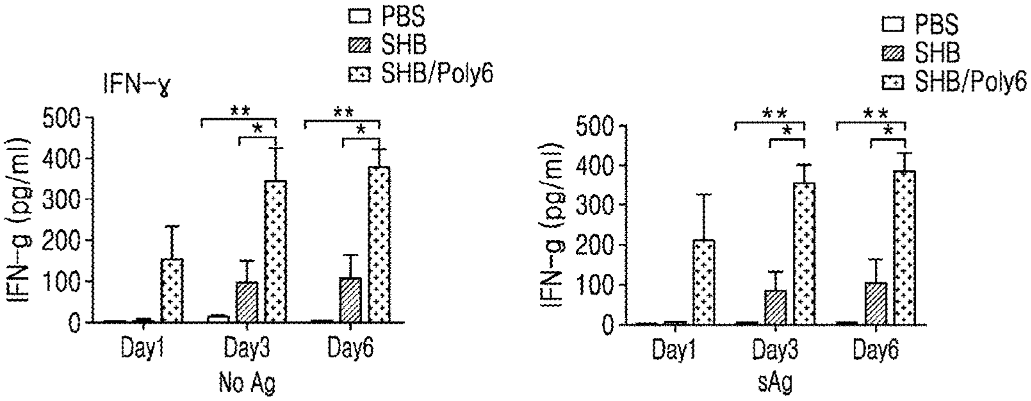
Figure 28C:
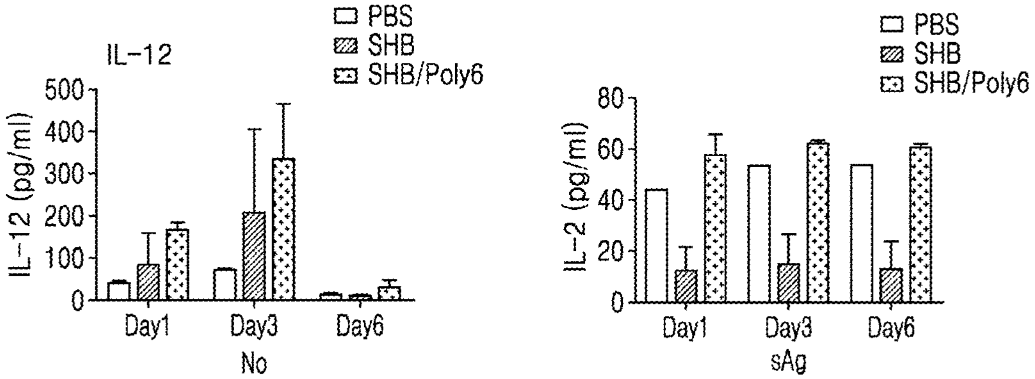

FIG. 28 is a diagram showing measurement results of cytokines secreted from splenocytes when S antigens and Poly6 are co-administered to TG mice.

Figure 29:
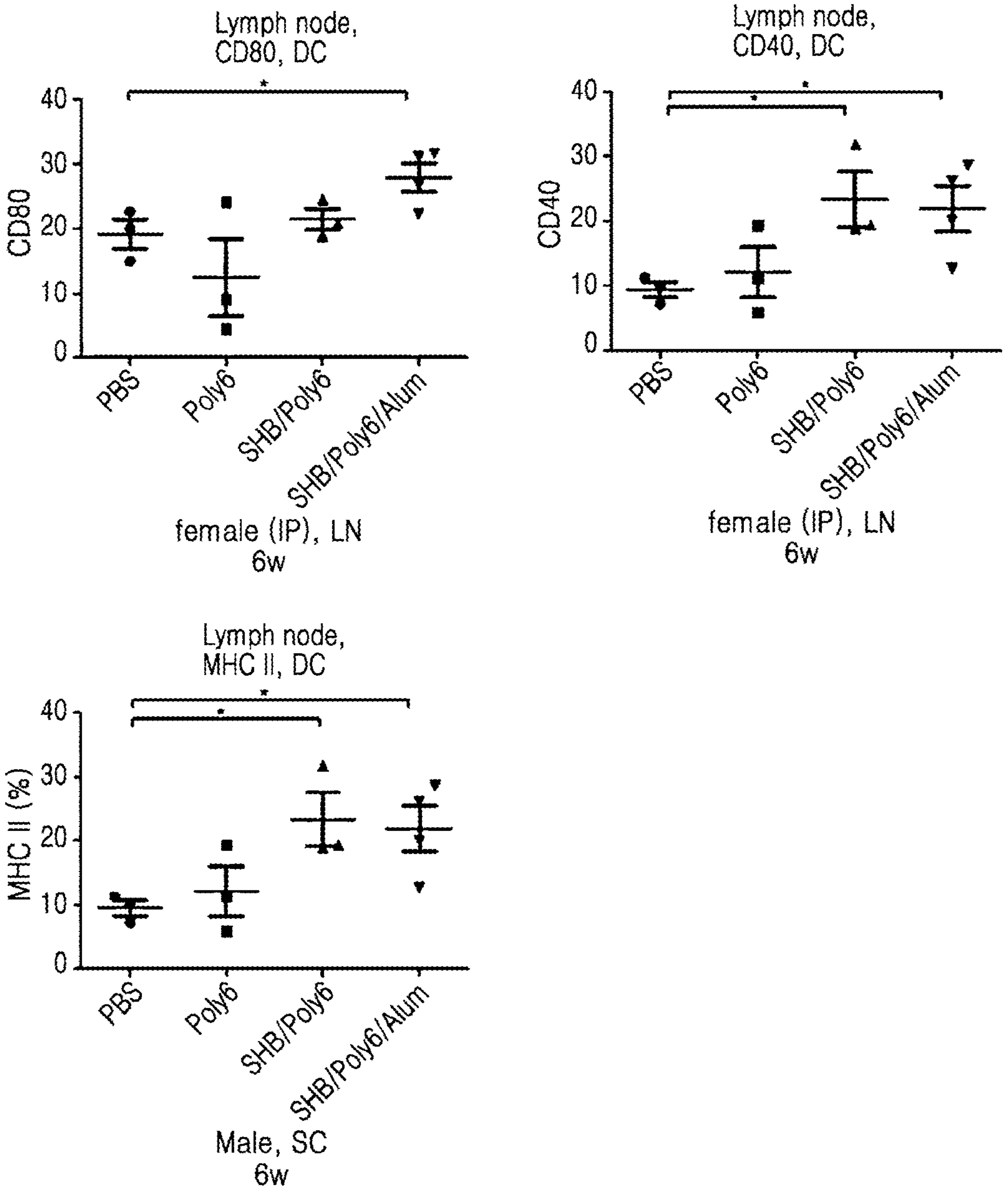

FIG. 29 is a diagram measuring degrees of maturation of dendritic cells in the lymph nodes when S antigens and Poly6 are co-administered to TG mice.

Figure 30:
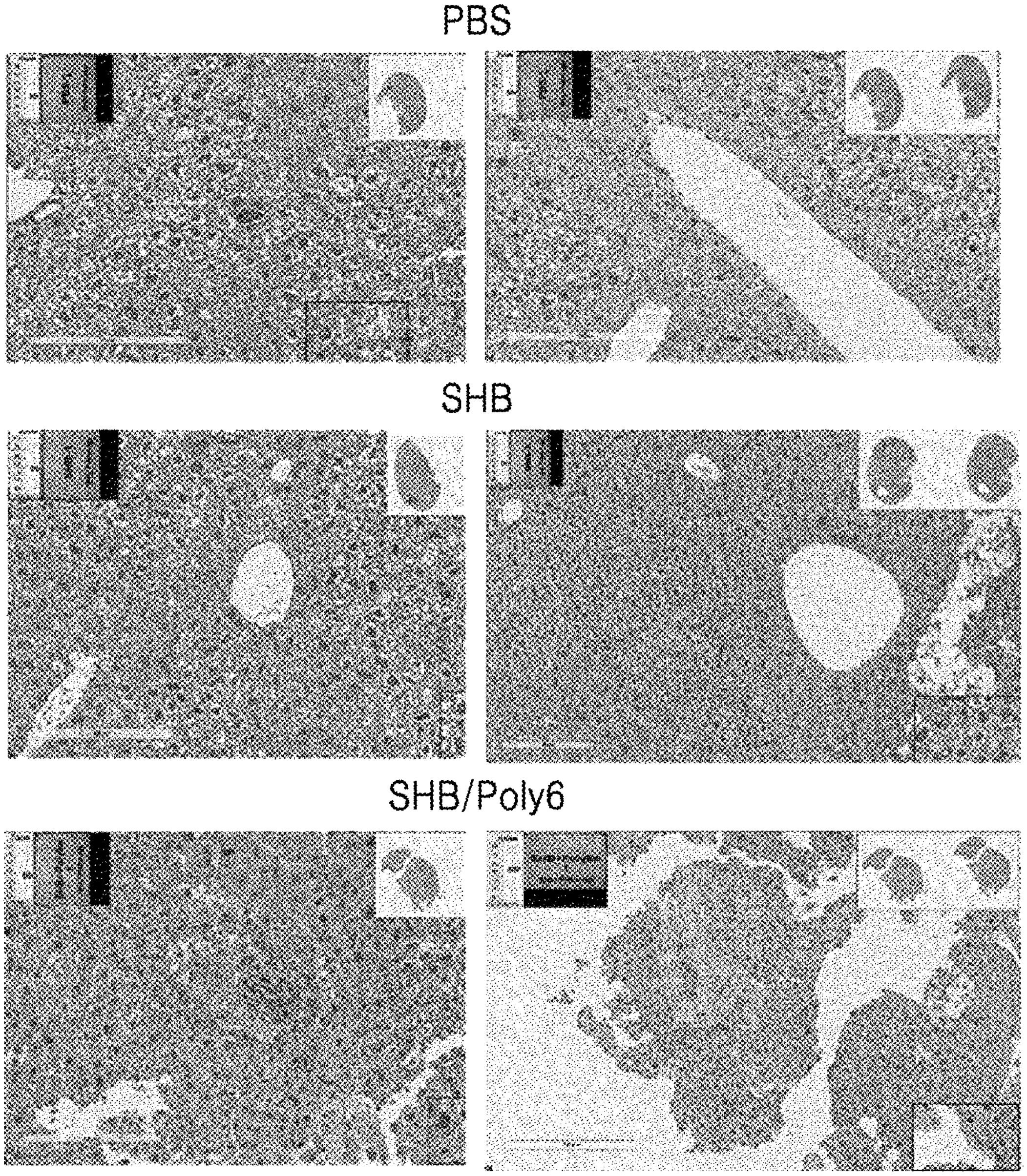

FIG. 30 is a diagram showing histopathological evaluation of the liver tissue of a mouse by using hematoxylin and eosin (H&E) staining, when Poly6 and sAg are co-administered.

Figure 31:
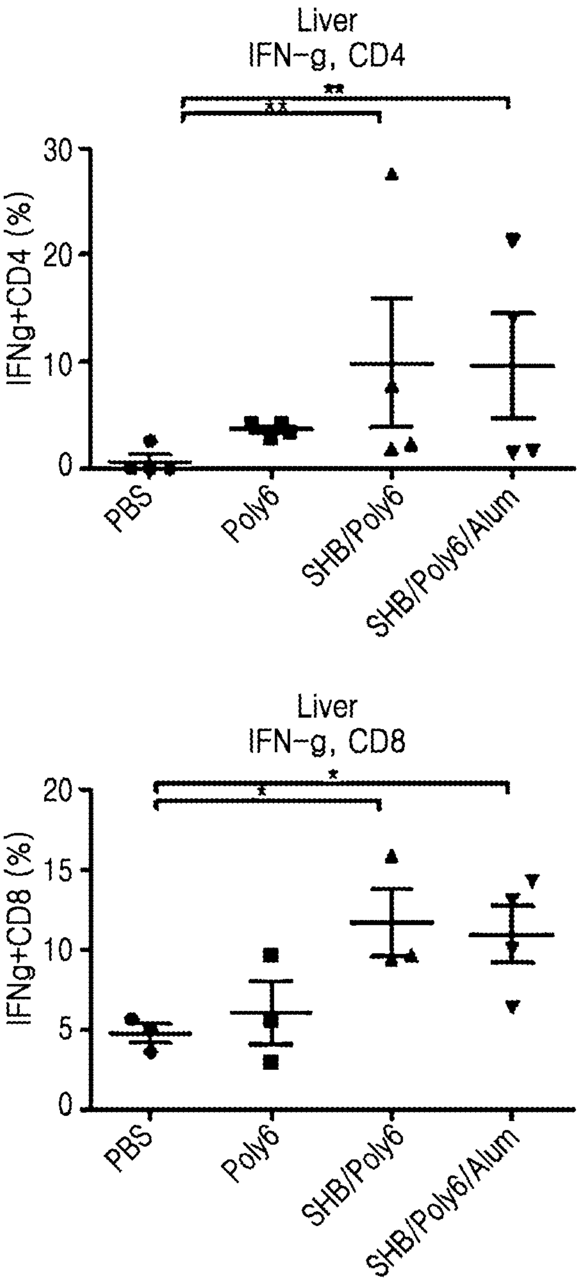

FIG. 31 is a diagram showing results of evaluation of activation of IFN-γ-secreting T cells in the liver tissue of TG mice, when S antigens and Poly6 are co-administered.

Figure 32:
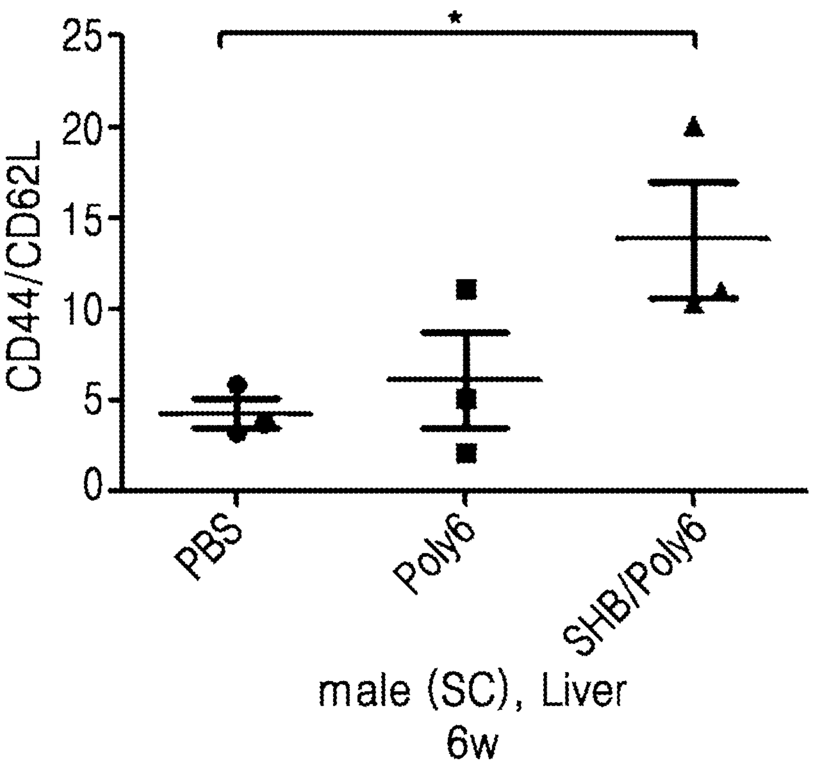

FIG. 32 is a diagram showing results of evaluation of effector memory T cell populations, when S antigens and Poly6 are co-administered.

Figure 33:
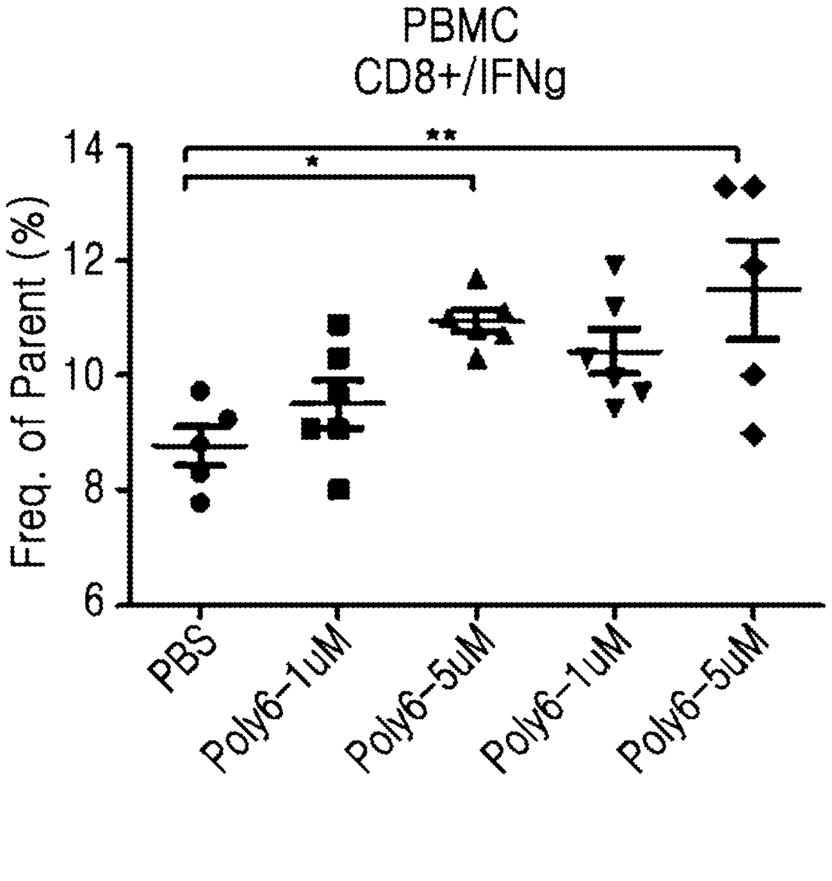

FIG. 33 is a diagram showing results of evaluation of IFN-γ-secreting T cell expression according to Poly6 treatment in peripheral blood mononuclear cells.

Figure 34A:
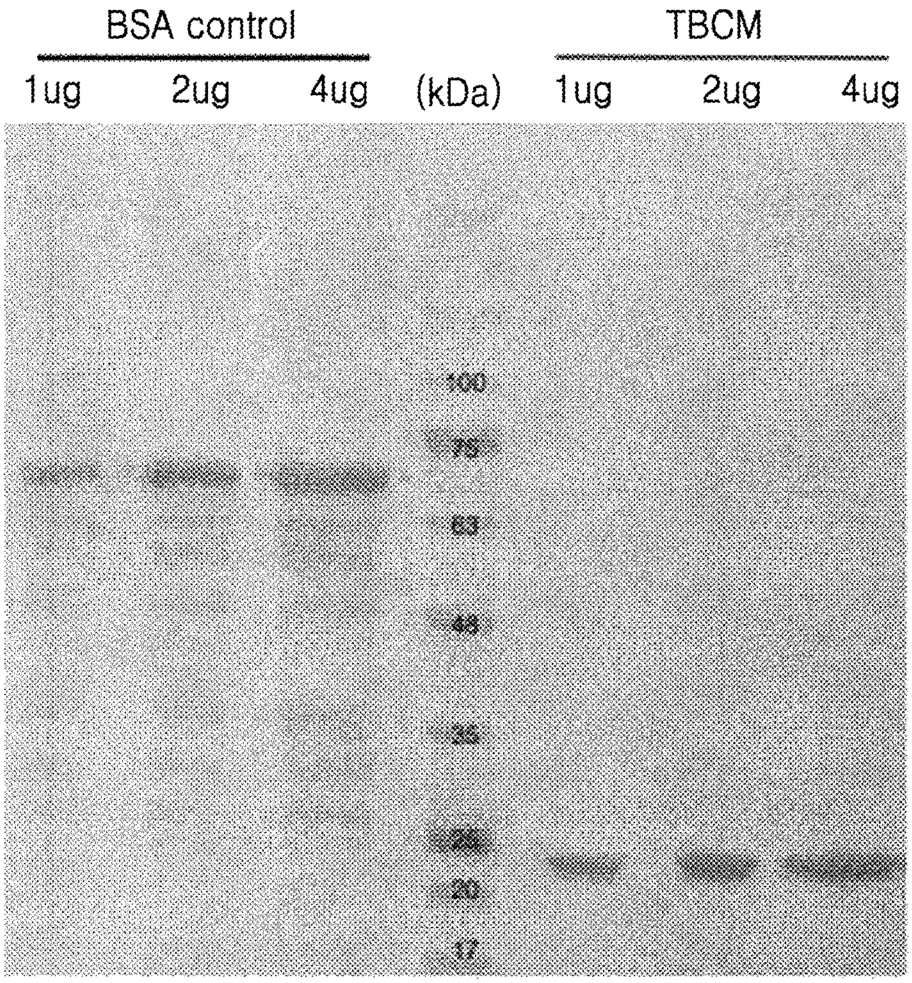
Figure 34B:
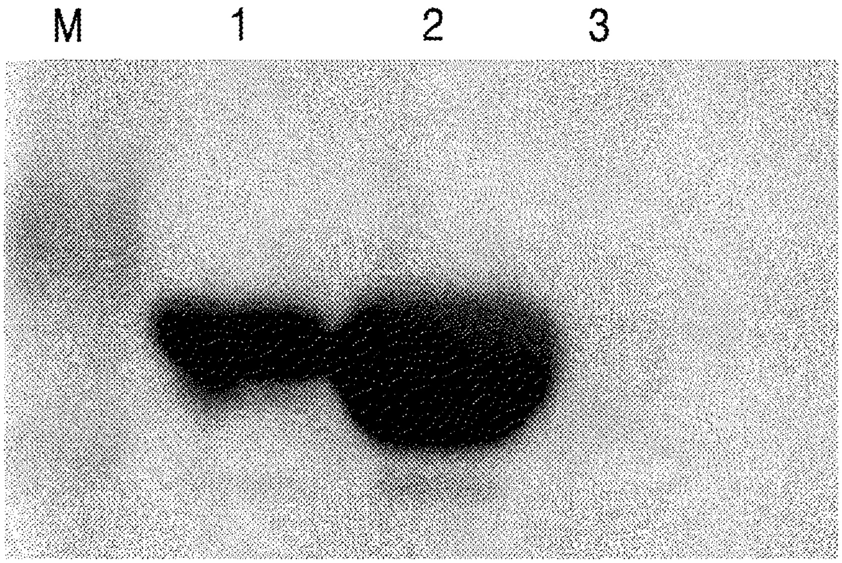

(A) of FIG. 34 shows results of staining with Coomassie blue after performing SDS-PAGE for each concentration with separated and purified TBCM proteins, and (B) shows results of performing western blot on the separated and purified TBCM proteins with polyclonal anti-TBCM antibodies. (M, marker; 1, TBCM (1 μg); 2, TBCM (5 μg); 3, p24 (5 μg)).

Figure 35:
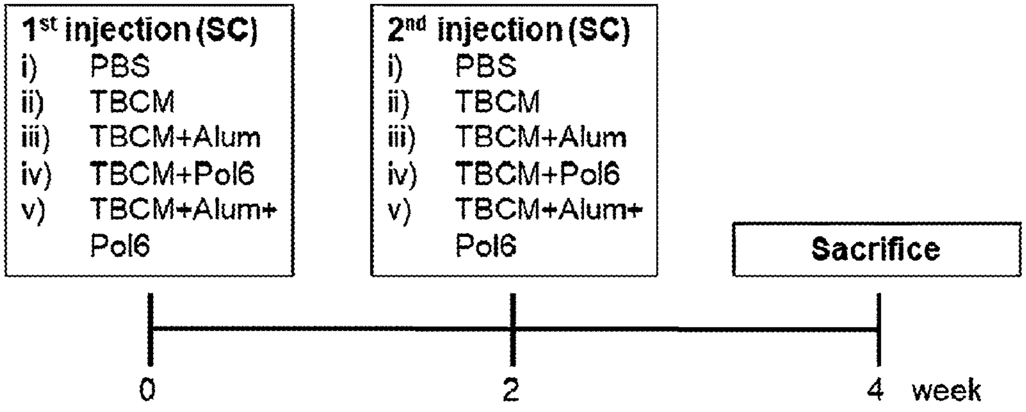

FIG. 35 is a diagram showing a mouse subcutaneous (SC) immunization schedule by using TBCM and various combinations of adjuvants.

Figure 36:
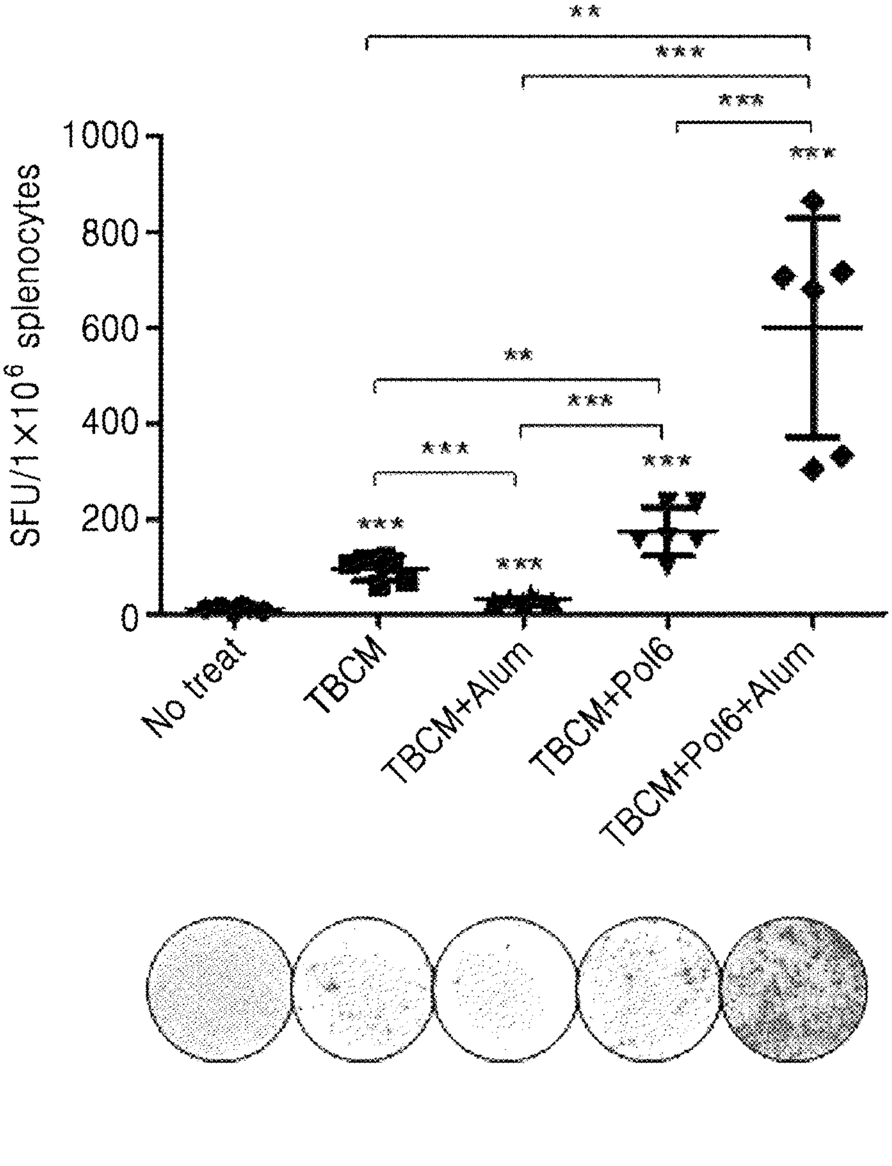
Figure 37A:
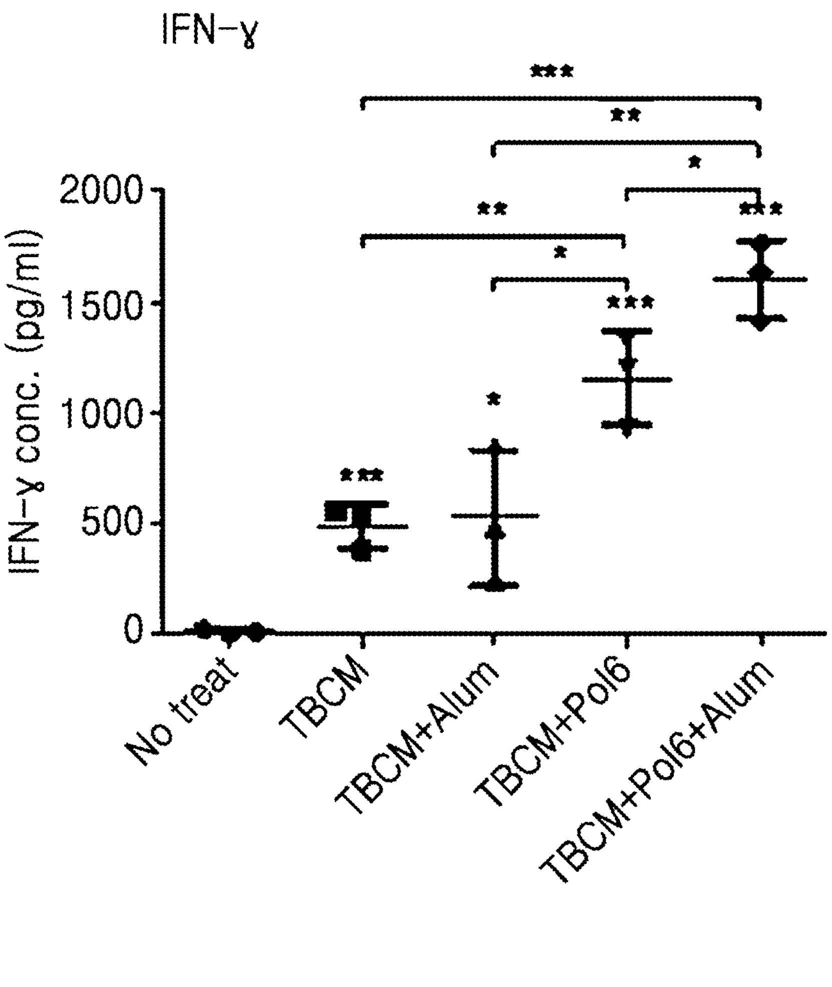
Figure 37B:
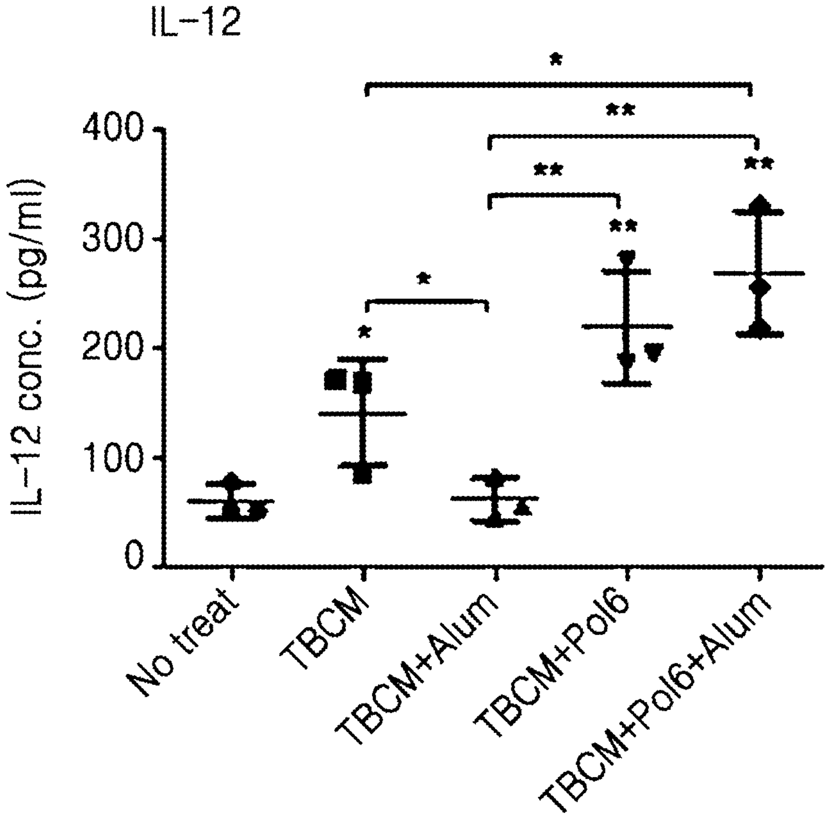
Figure 37C:
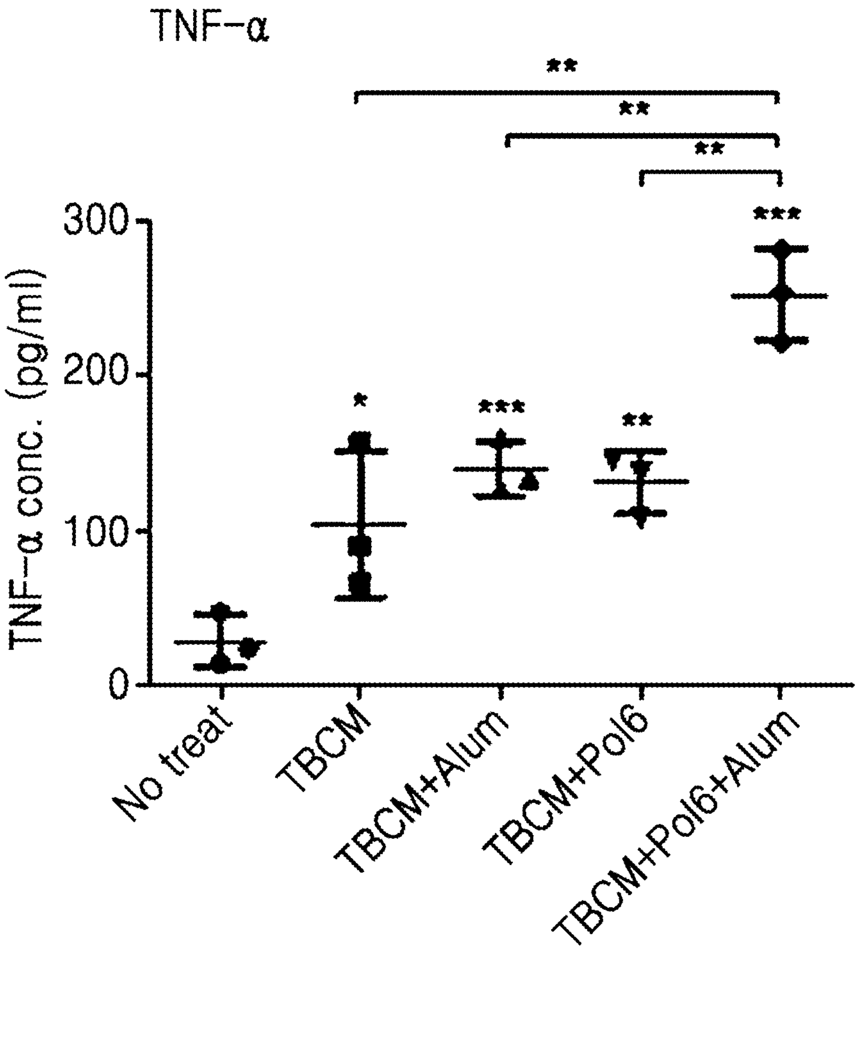
Figure 37D:
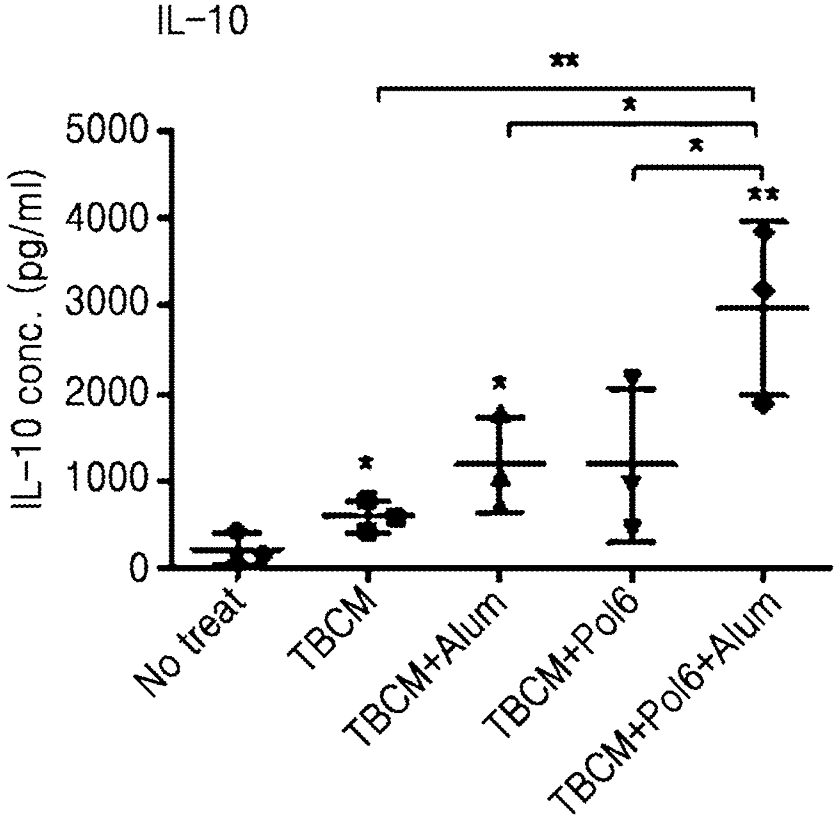

FIG. 36 is a diagram showing data obtained by measuring amounts of IFN-γ expressed in cells by using ELISPOT, when splenocytes, obtained by immunizing with TBCM and various combinations of adjuvants, are stimulated with TBCM (statistical significance is tested by Student-t-test, *, P<0.05; , P<0.01; *, P<0.001).

FIG. 37 shows results of confirming cytokines (A) IFN-γ, (B) IL-12, (C) TNF-α, and (D) IL-10 expressed in cell culture medium by using ELISA, when splenocytes obtained by immunization with TBCM and various adjuvant combinations are stimulated with TBCM (statistical significance is tested by Student-t-test, *, P<0.05; , P<0.01; *, P<0.001).

Figure 38A:
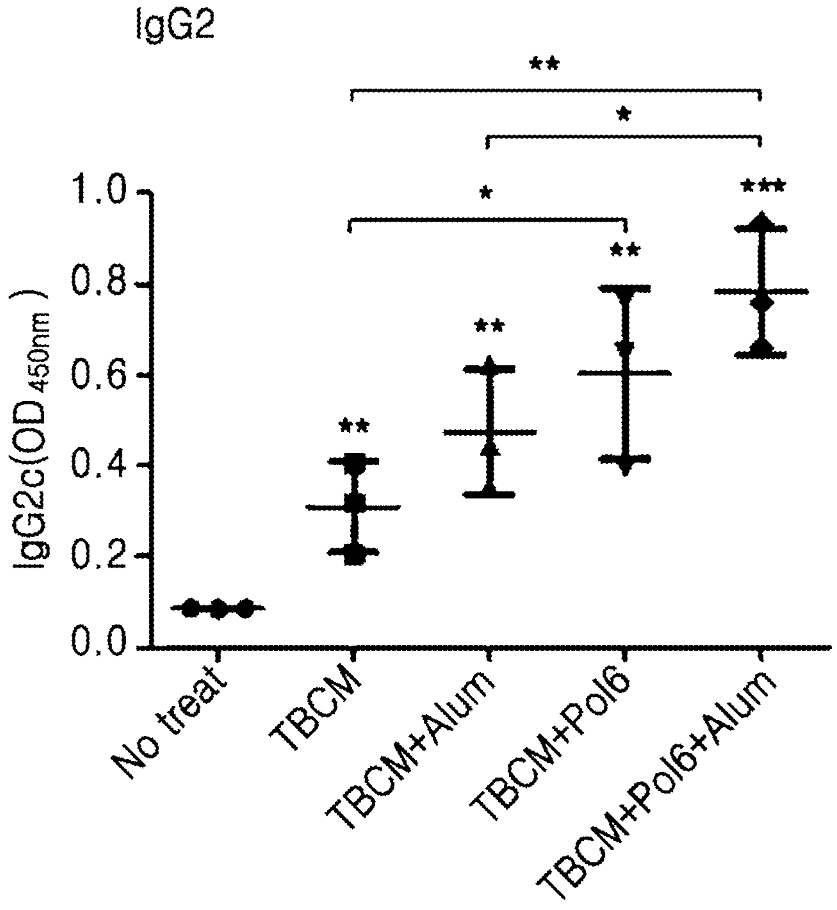
Figure 38B:
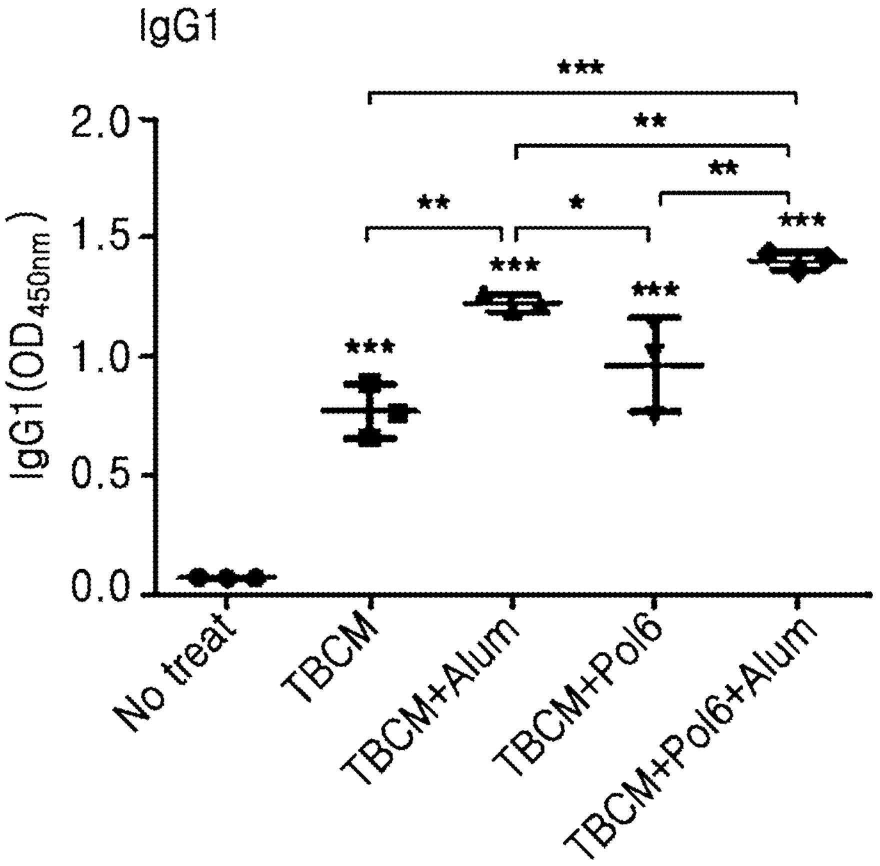
Figure 38C:
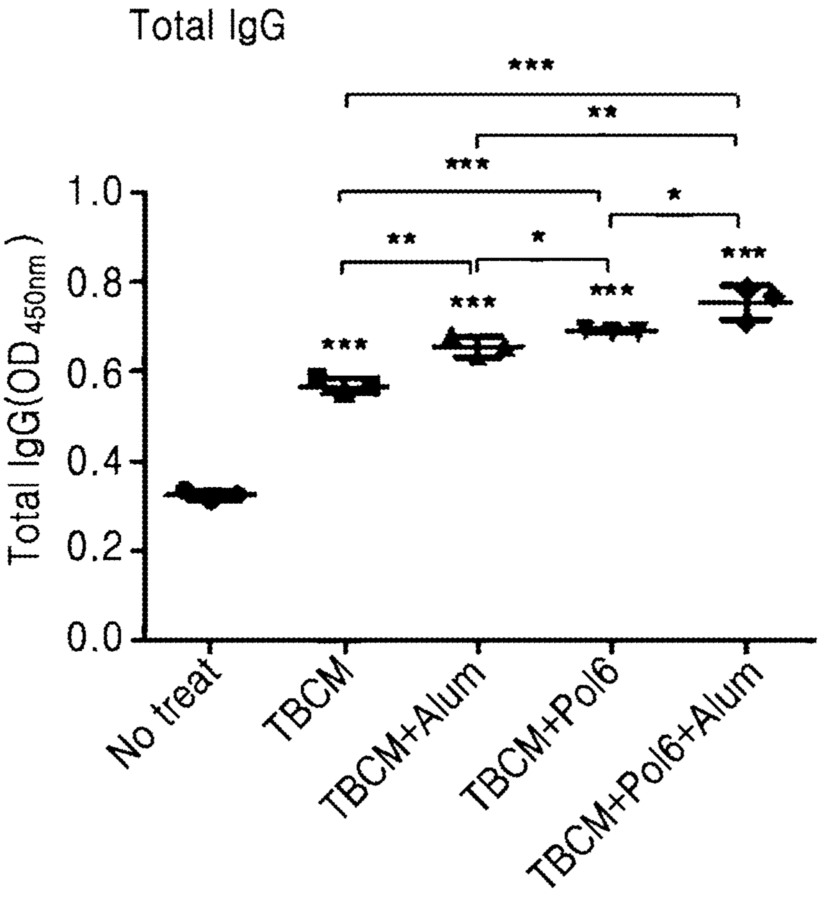

FIG. 38 shows results of confirming expression of TBCM-specific (A) IgG2, (B) IgG1, and (C) total IgG in serum by using ELISA after immunization with TBCM and various adjuvant combinations (statistical significance is tested by Student-t-test, *, P<0.05; , P<0.01; *, P<0.001).

Figure 39:
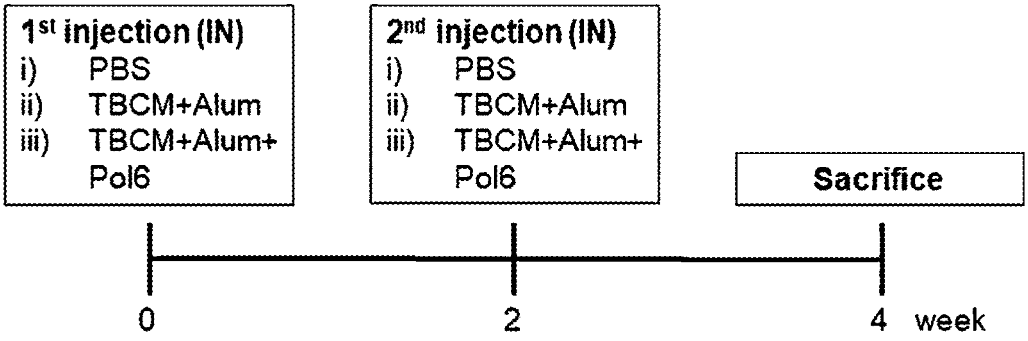

FIG. 39 is a diagram showing a mouse intranasal (IN) immunization schedule by using a combination of TBCM and Alum, or a combination of TBCM, Alum, and additional Pol6.

Figure 40A:
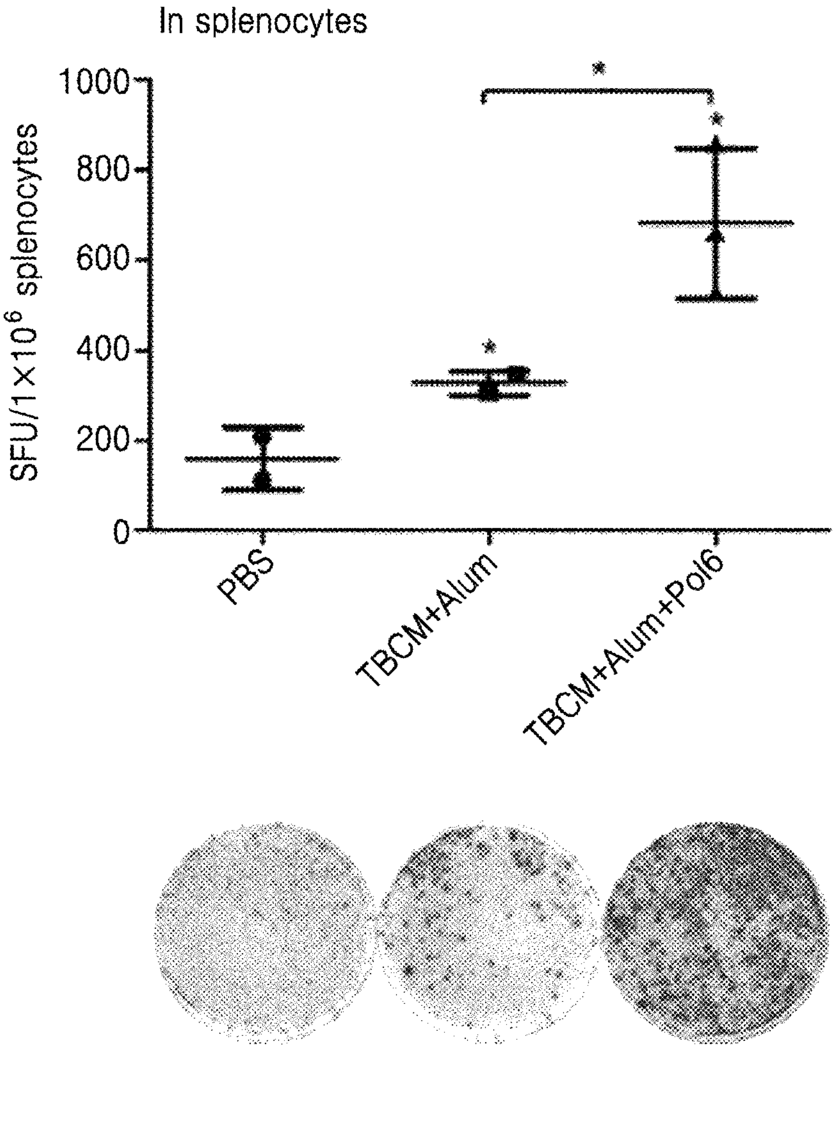
Figure 40B:
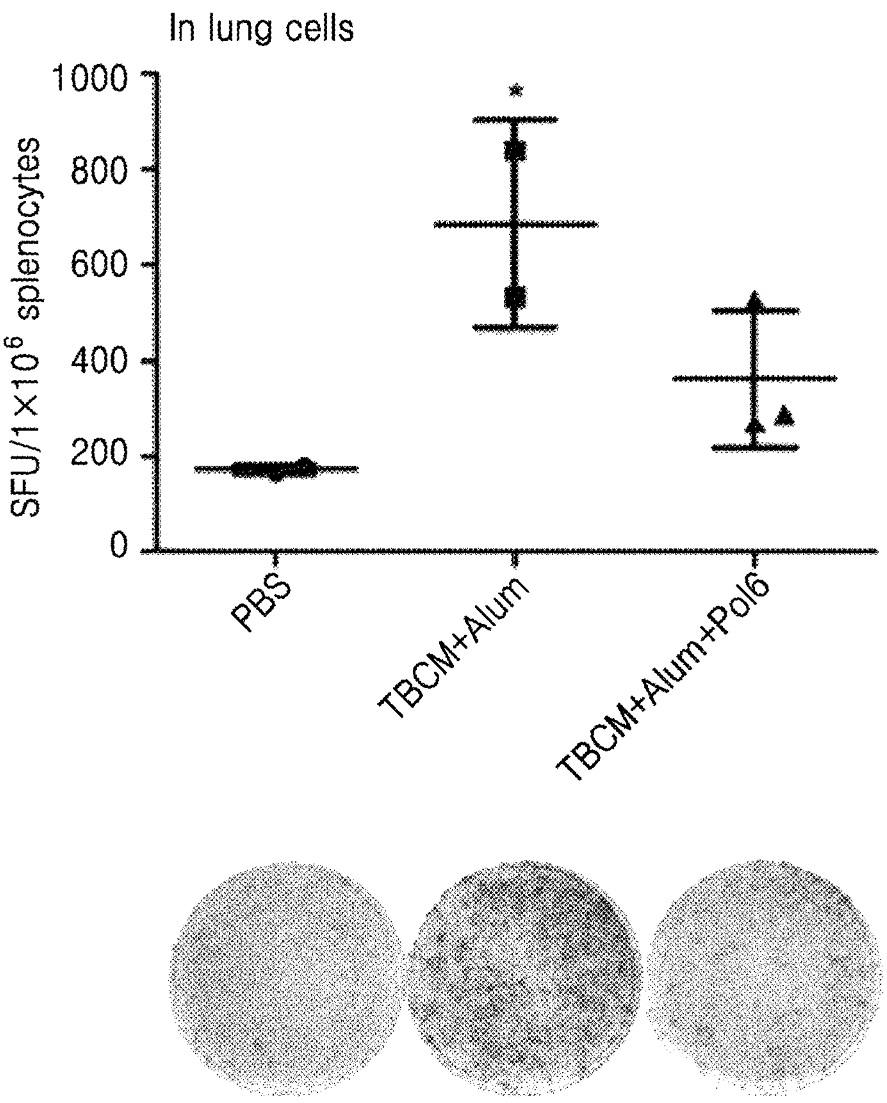
Figure 41A:
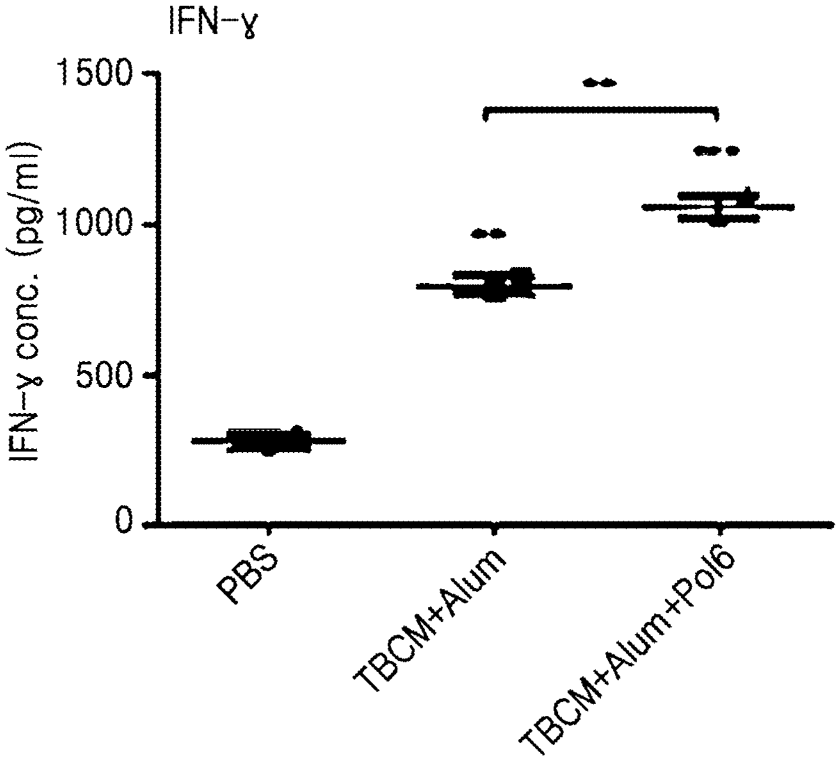
Figure 41B:
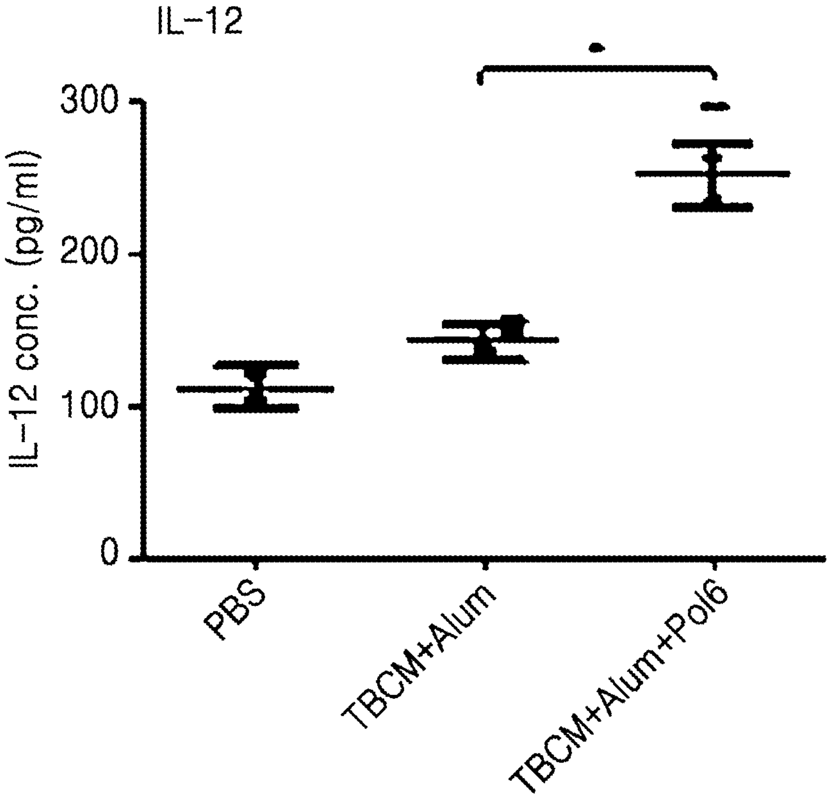
Figure 41C:
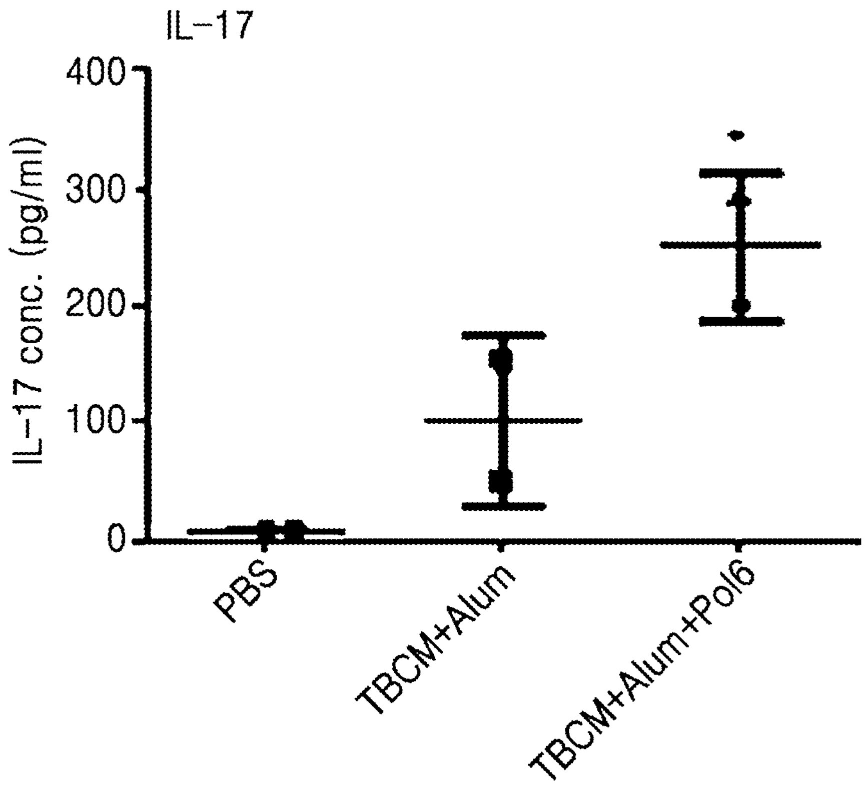
Figure 41D:
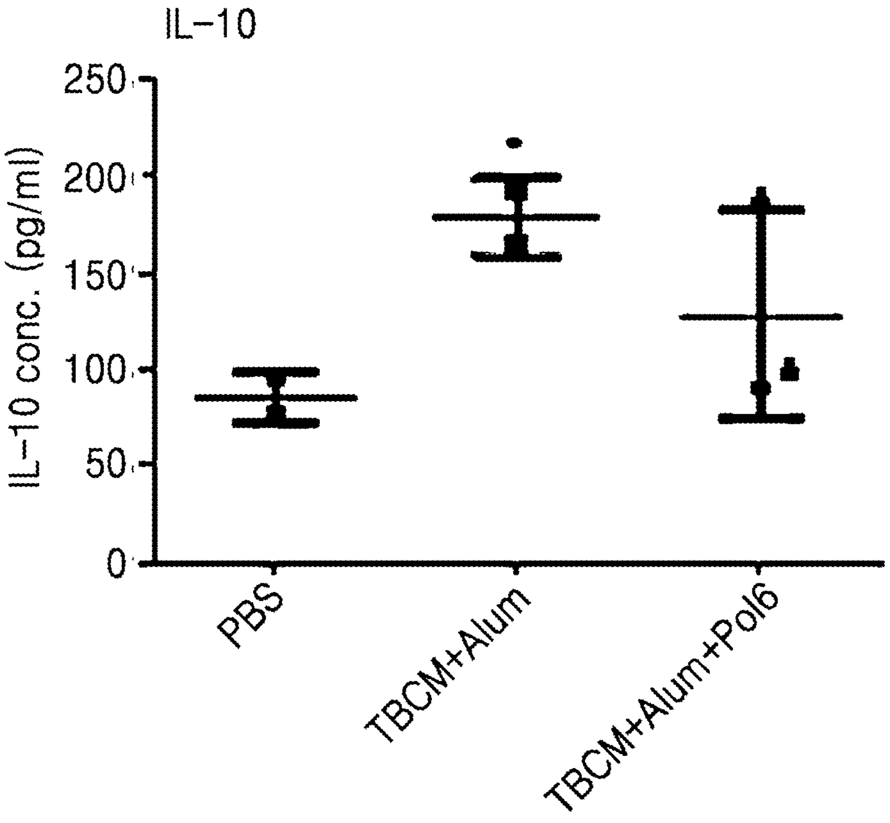
Figure 42A:
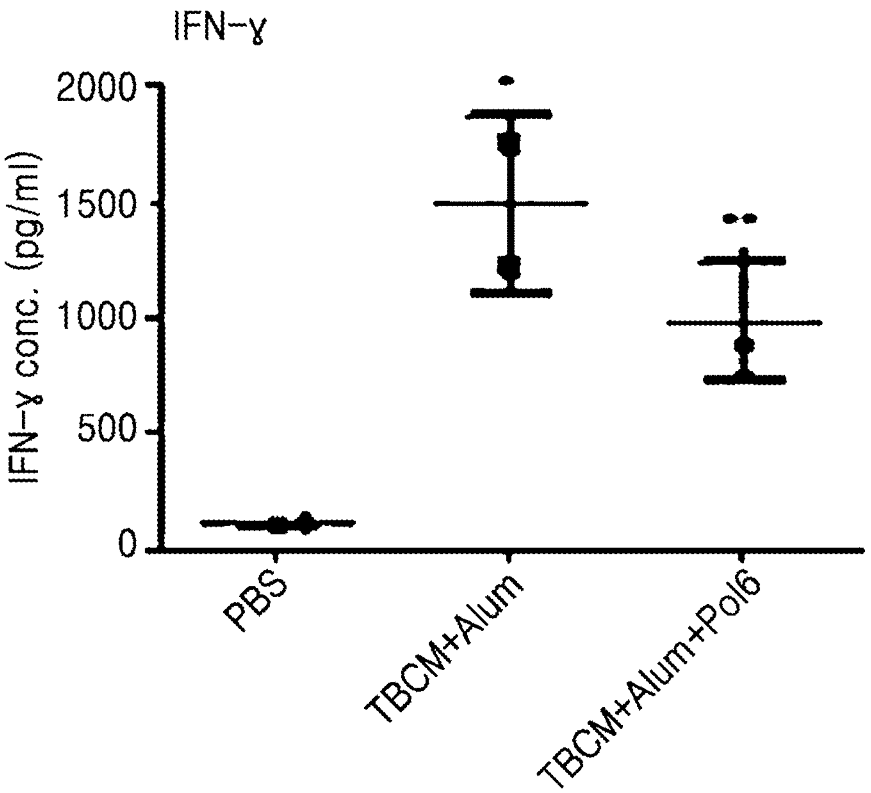
Figure 42B:
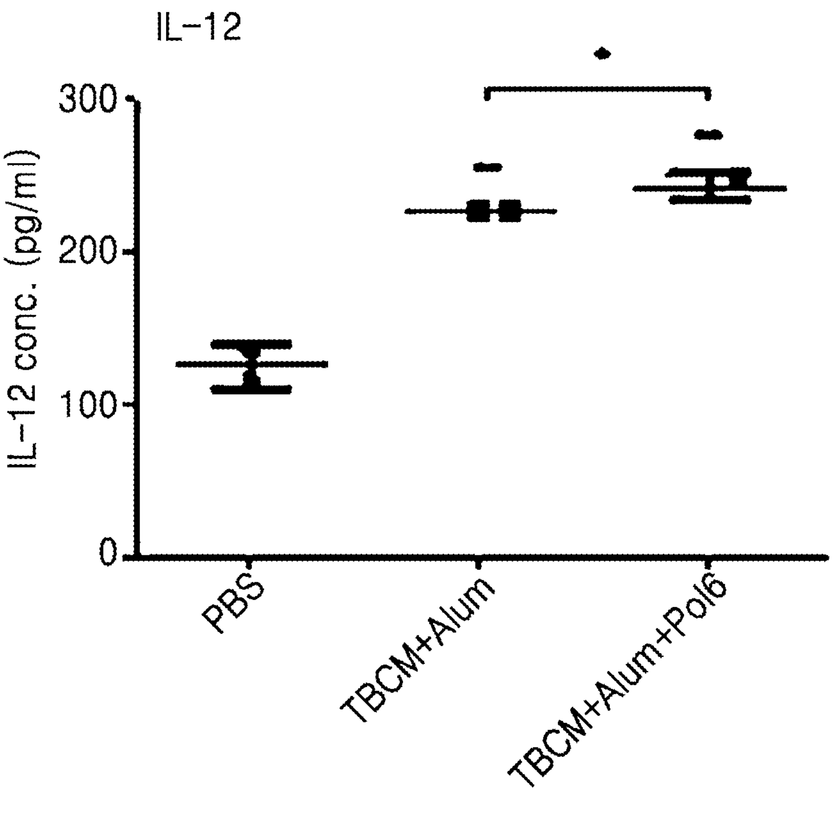
Figure 42C:
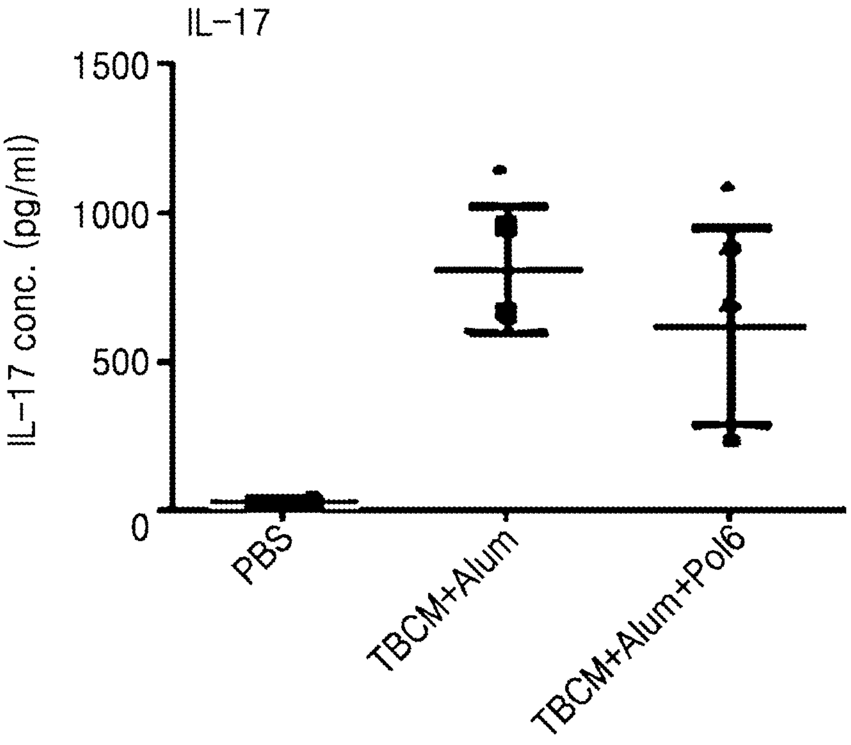
Figure 42D:
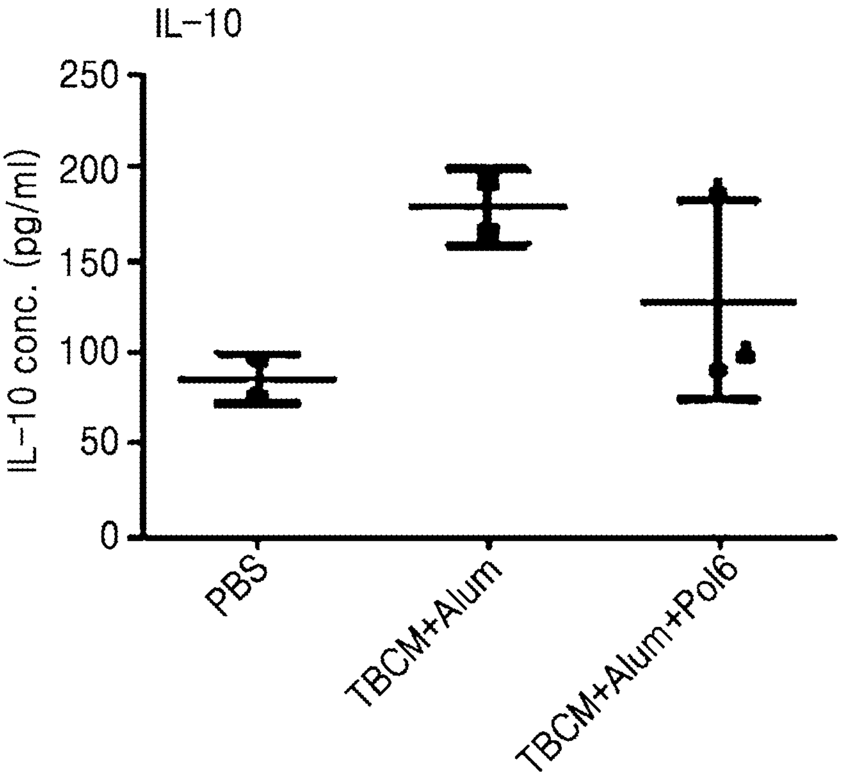

FIG. 40 is a diagram showing data obtained by measuring amounts of IFN-γ expressed in cells by using ELISPOT, when splenocytes and pneumocytes obtained by immunization (IN route) with a combination of TBCM and Alum, or a combination of TBCM, Alum, and additional Pol6 were stimulated with TBCM (statistical significance is tested by Student-t-test, *, P<0.05).

FIG. 41 shows results of confirming cytokines (A) IFN-γ, (B) IL-12, (C) IL-17, and (D) IL-10 expressed in cell culture medium by using ELISA, when splenocytes obtained by immunization (IN route) with a combination of TBCM and Alum, or a combination of TBCM, Alum, and additional Pol6 were stimulated with TBCM (statistical significance is tested by Student-t-test, *, P<0.05; , P<0.01; *, P<0.001).

FIG. 42 shows results of confirming cytokines (A) IFN-γ, (B) IL-12, (C) IL-17, and (D) IL-10 expressed in cell culture medium by using ELISA when pneumocytes obtained by immunization (IN route) with a combination of TBCM and Alum, or a combination of TBCM, Alum, and additional Pol6 were stimulated with TBCM (statistical significance is tested by Student-t-test, *, P<0.05; , P<0.01; *, P<0.001).

Figure 43:
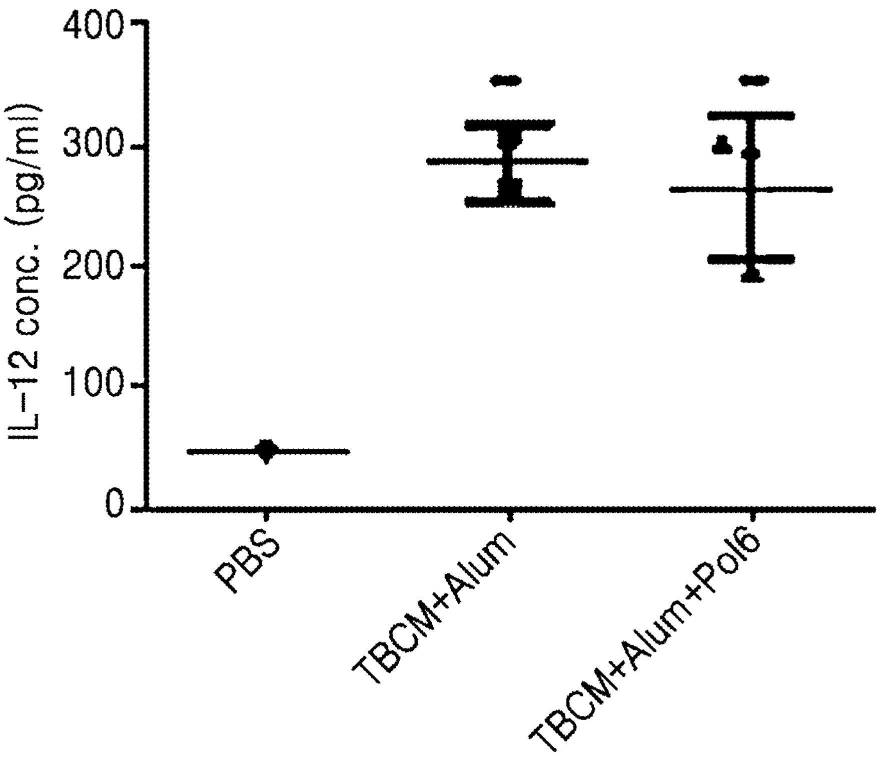
Figure 44A:
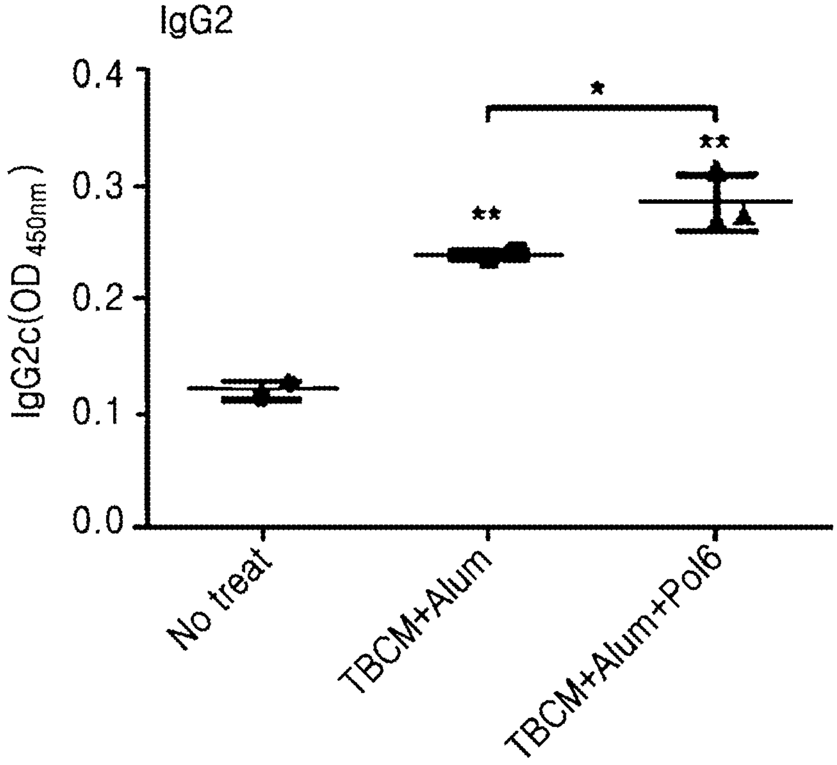
Figure 44B:
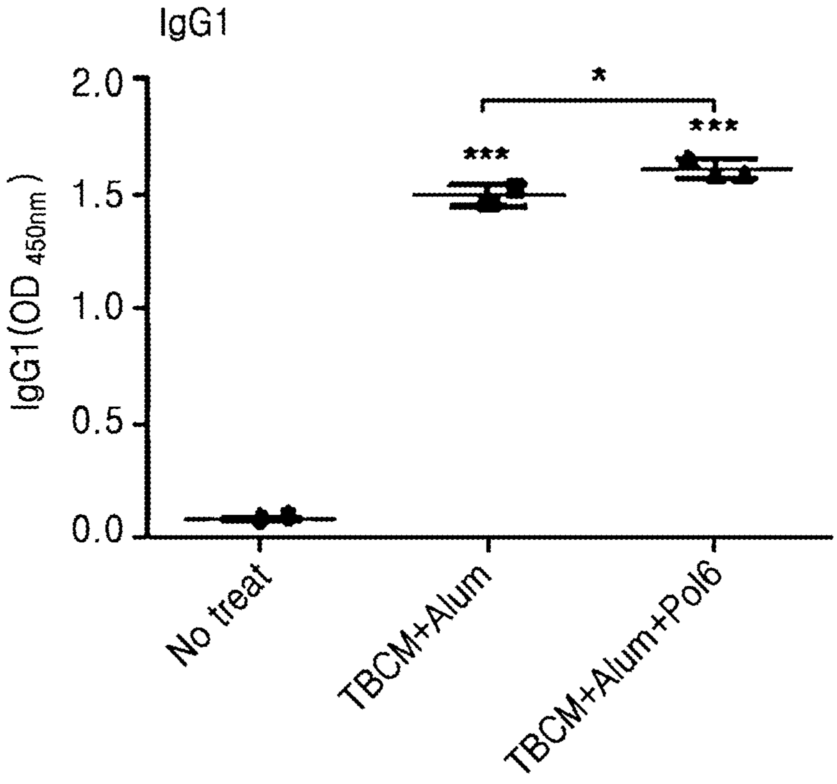
Figure 44C:
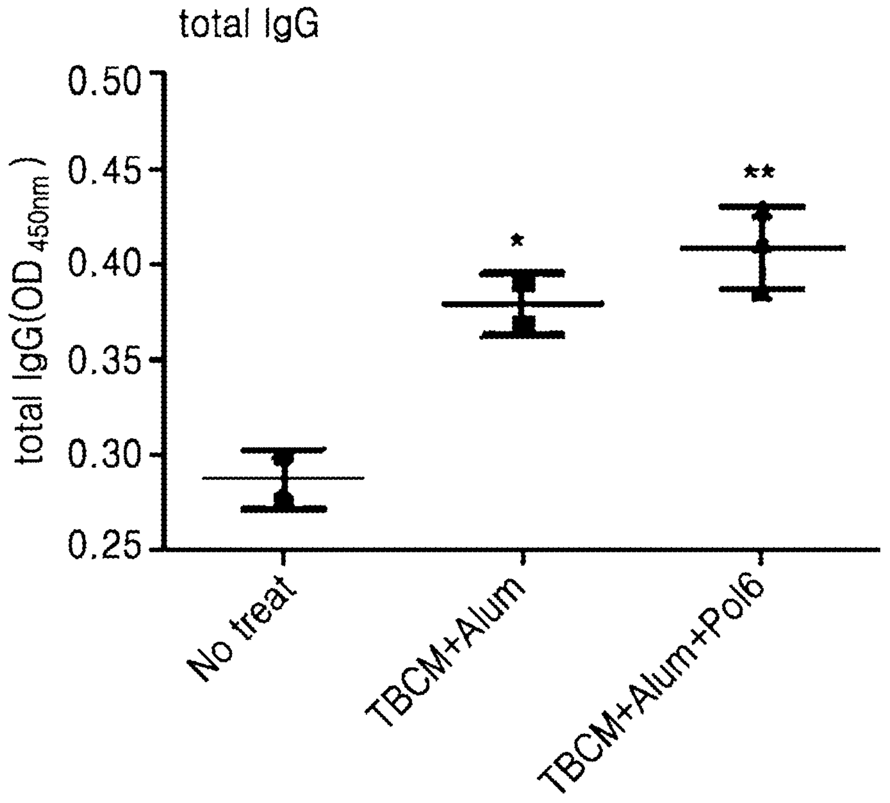
Figure 44D:
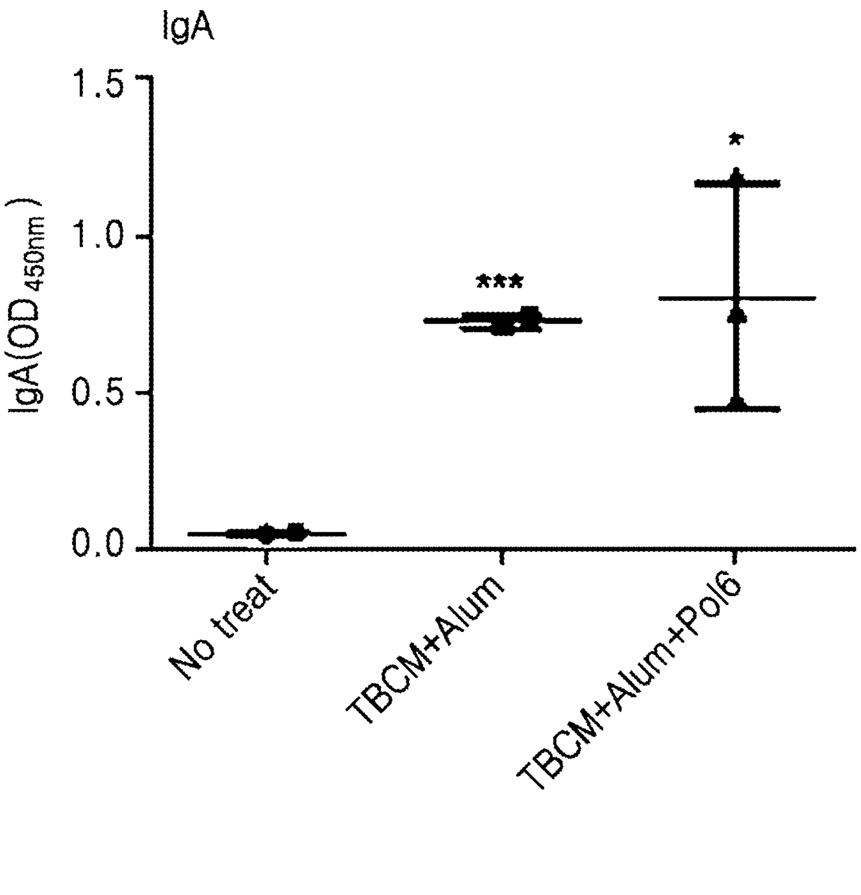

FIG. 43 shows results of confirming expression levels of IL-12 in bronchoalveolar lavage fluid (BAL fluid) by using ELISA, after immunization (IN route) with a combination of TBCM and Alum, or a combination of TBCM, Alum, and additional Pol6 (statistical significance is tested by Student-t-test, **, P<0.01).

FIG. 44 shows results of confirming expression of TBCM-specific (A) IgG2, (B) IgG1, and (C) total IgG in serum and BAL fluid by using ELISA, after immunization (IN route) with a combination of TBCM and Alum, or a combination of TBCM, Alum, and additional Pol6 (statistical significance is tested by Student-t-test, *, P<0.05; , P<0.01; *, P<0.001).

Figure 45:
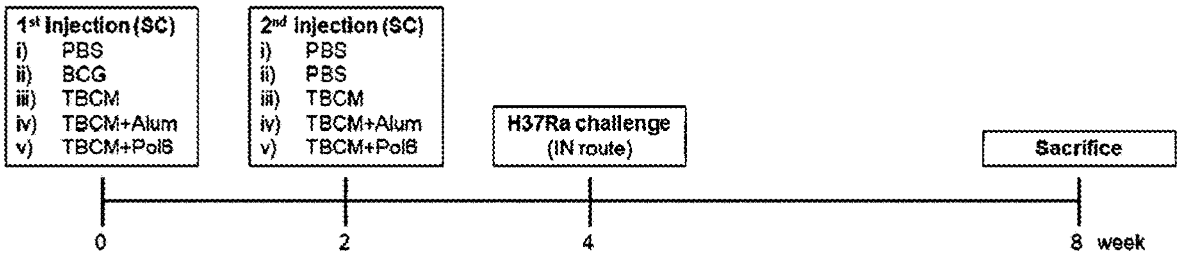

FIG. 45 is a diagram showing a mouse immunization schedule by using TBCM and various combinations of adjuvants. Specifically, a BCG immunization group is selected as a comparison group, and after immunization, mice are sacrificed 4 weeks after H37Ra infection (IN) to observed immune responses and intra-organ colony forming units (CFUs), and lung tissue H&E staining are performed.

Figure 46A:
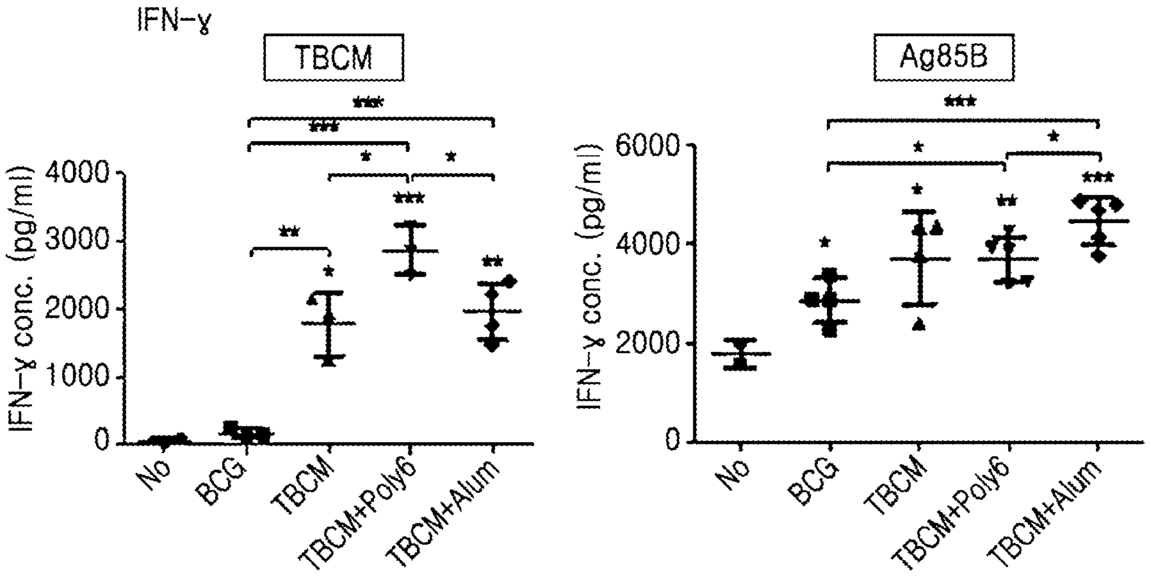
Figure 46B:
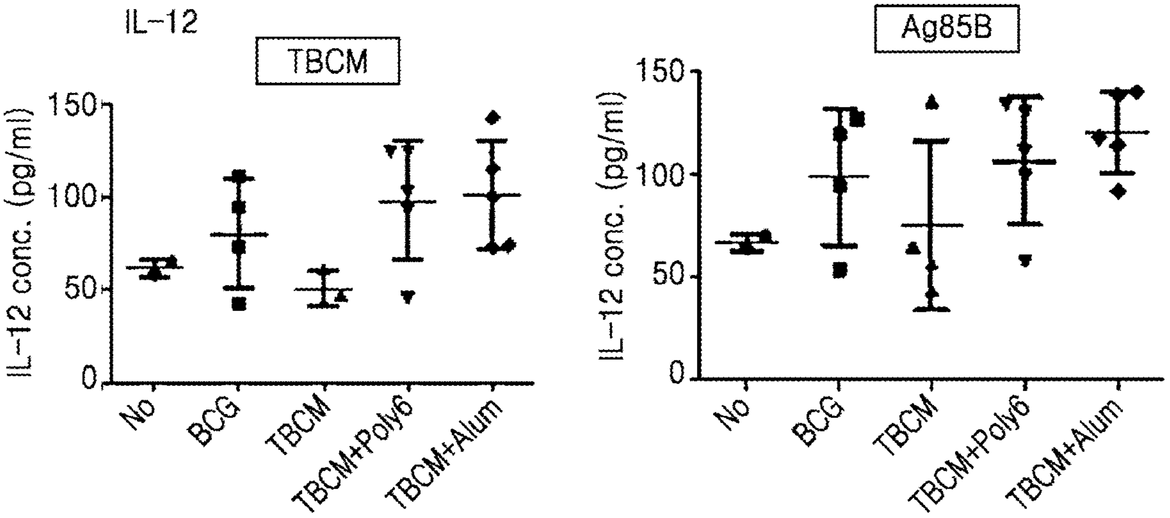
Figure 47A:
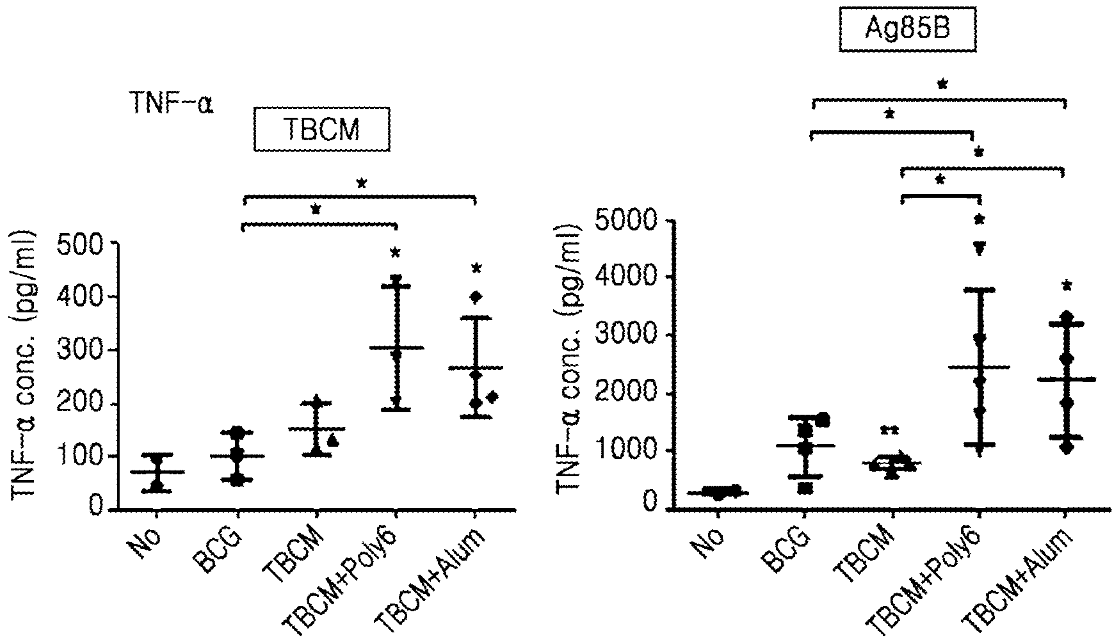
Figure 47B:
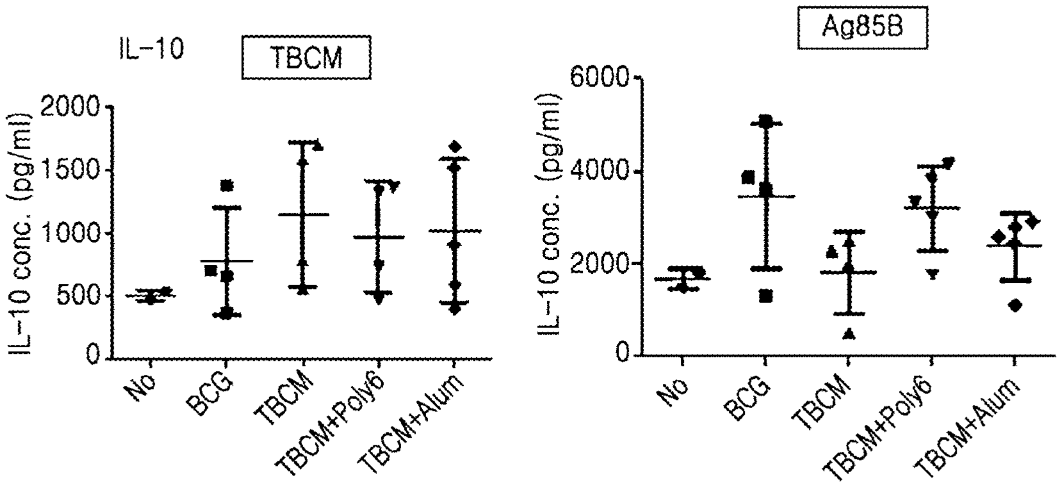
Figure 48A:
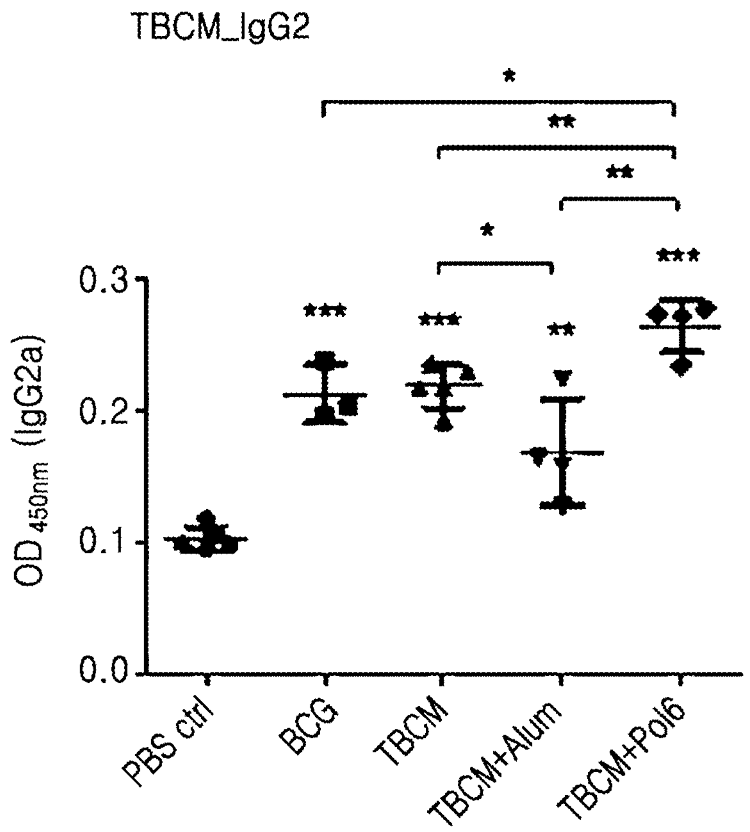
Figure 48B:
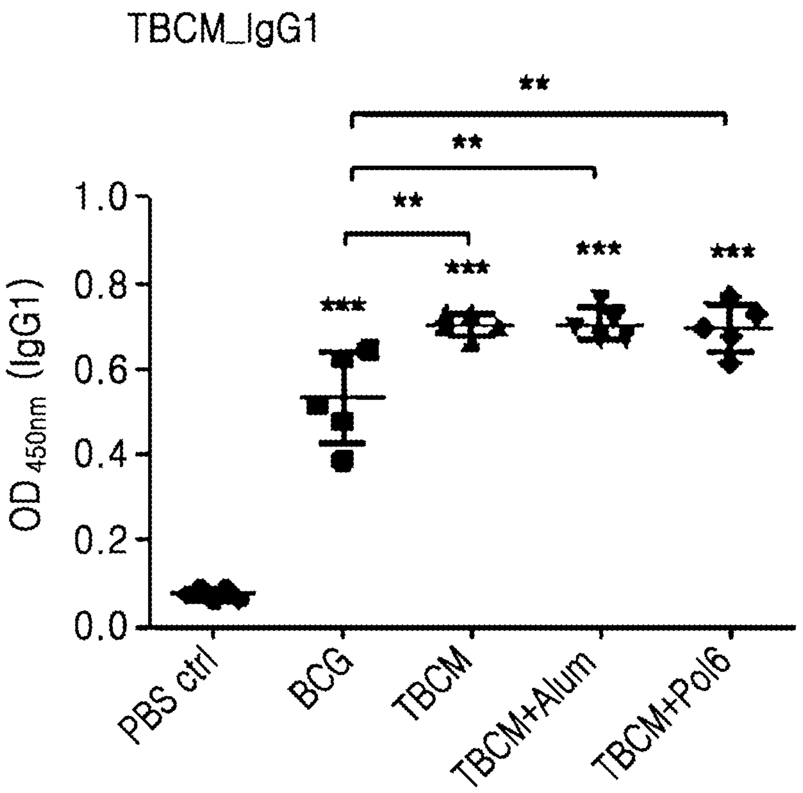
Figure 48C:
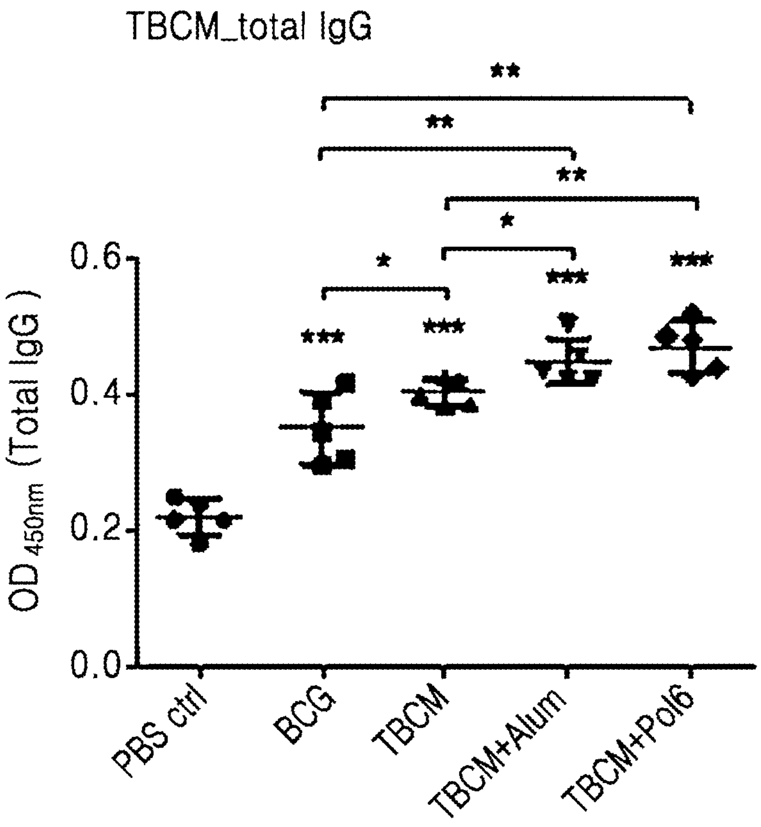
Figure 48D:
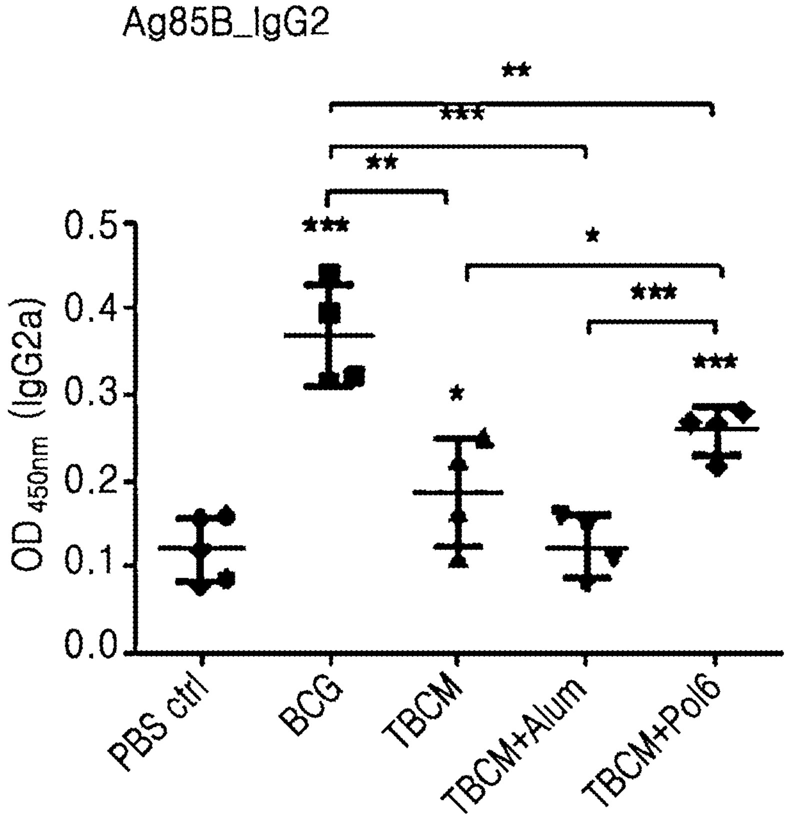
Figure 48E:
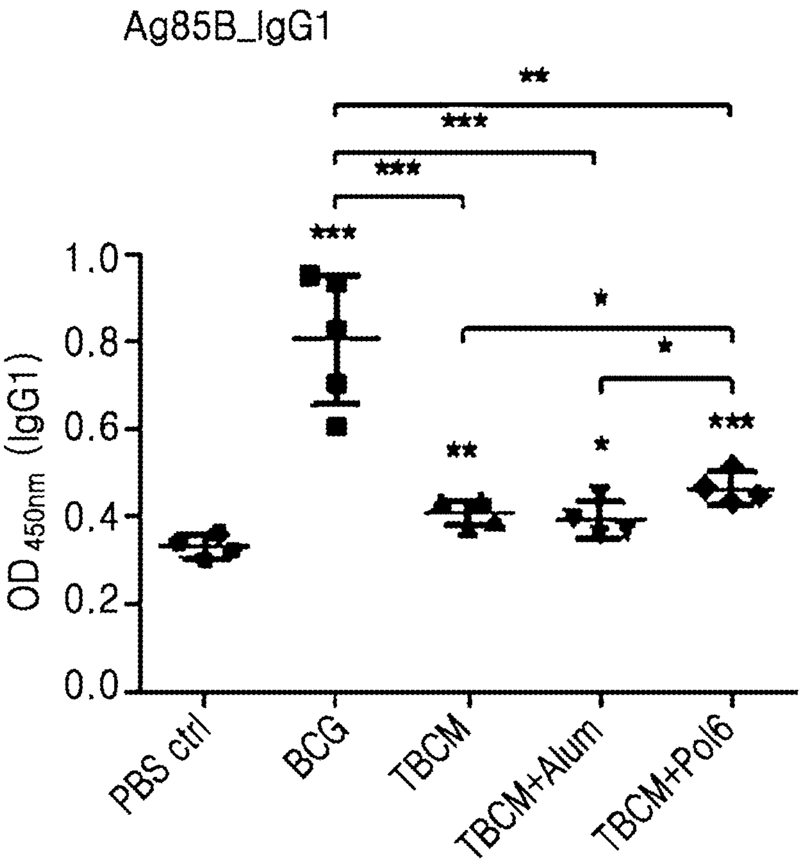
Figure 48F:
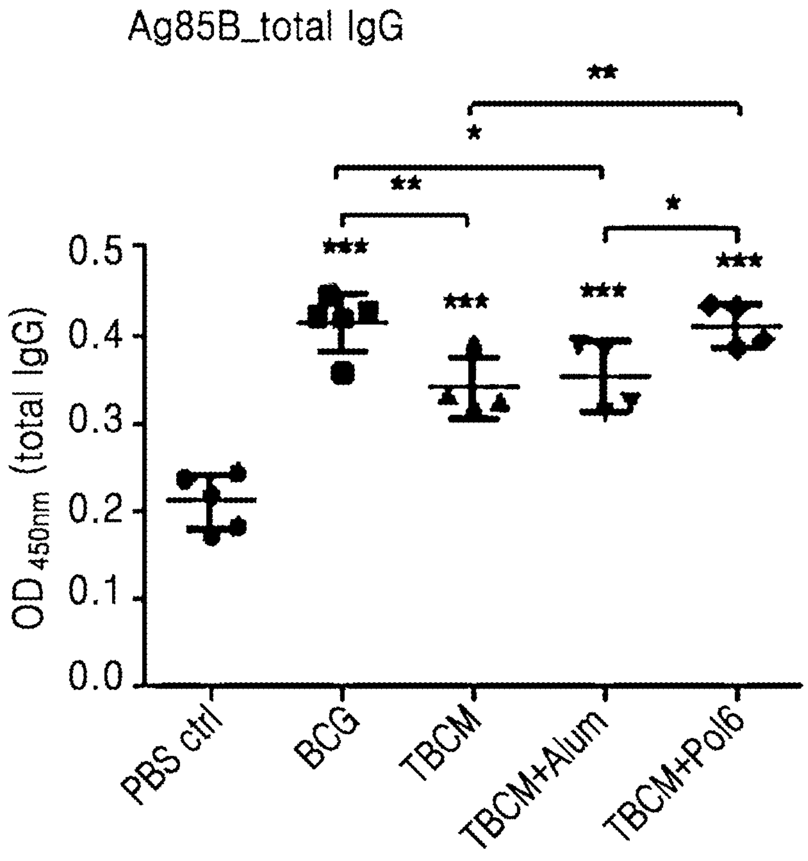

FIGS. 46 and 47 show results of confirming cytokines IFN-γ (FIG. 46A), IL-12 (FIG. 46B), TNF-α (FIG. 47A) and IL-10 (FIG. 47B) expressed in cell culture medium by using ELISA, when splenocytes obtained by infecting H37Ra after immunization with TBCM and various combinations of adjuvants are stimulated with TBCM and Ag85B proteins (statistical significance is tested by Student-t-test, *, P<0.05; , P<0.01; *, P<0.001).

FIG. 48 is a diagram showing results of confirming TBCM- and Ag85B protein-specific IgG2 (A and D), IgG1 (B and E), and total IgG (C and F) in serum obtained by infection with H37Ra after immunization with TBCM and various combinations of adjuvants, by using ELISA (statistical significance is tested by Student-t-test, *, P<0.05; , P<0.01; *, P<0.001).

Figure 49:
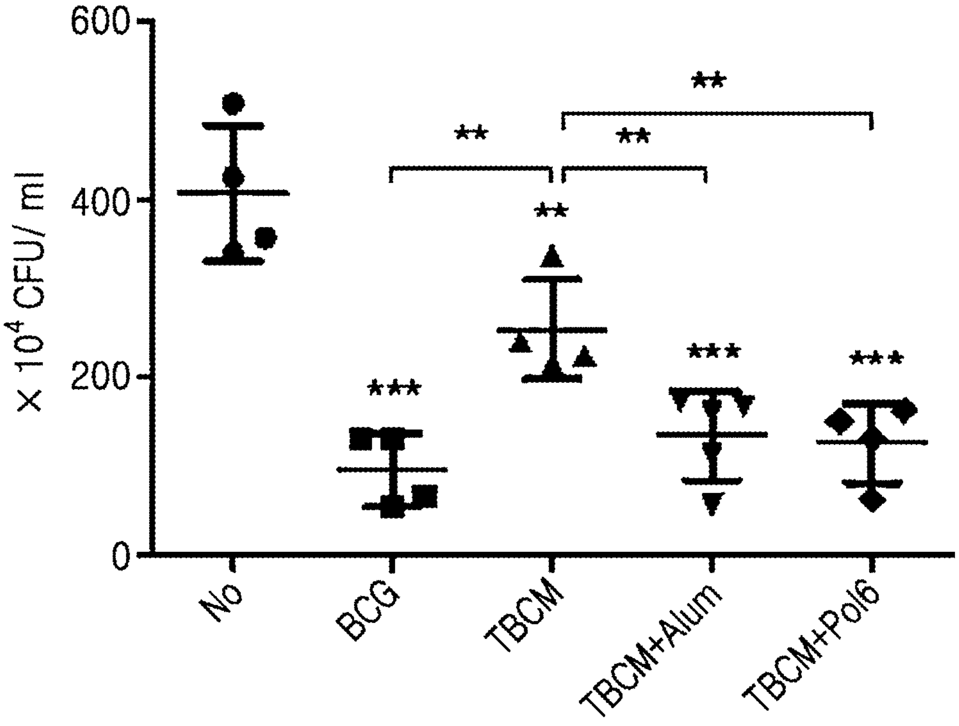

FIG. 49 is a diagram showing results of comparing numbers of H37Ra colonies identified in the lungs (statistical significance is tested by Student-t-test, , P<0.01; *, P<0.001).

Figure 50:
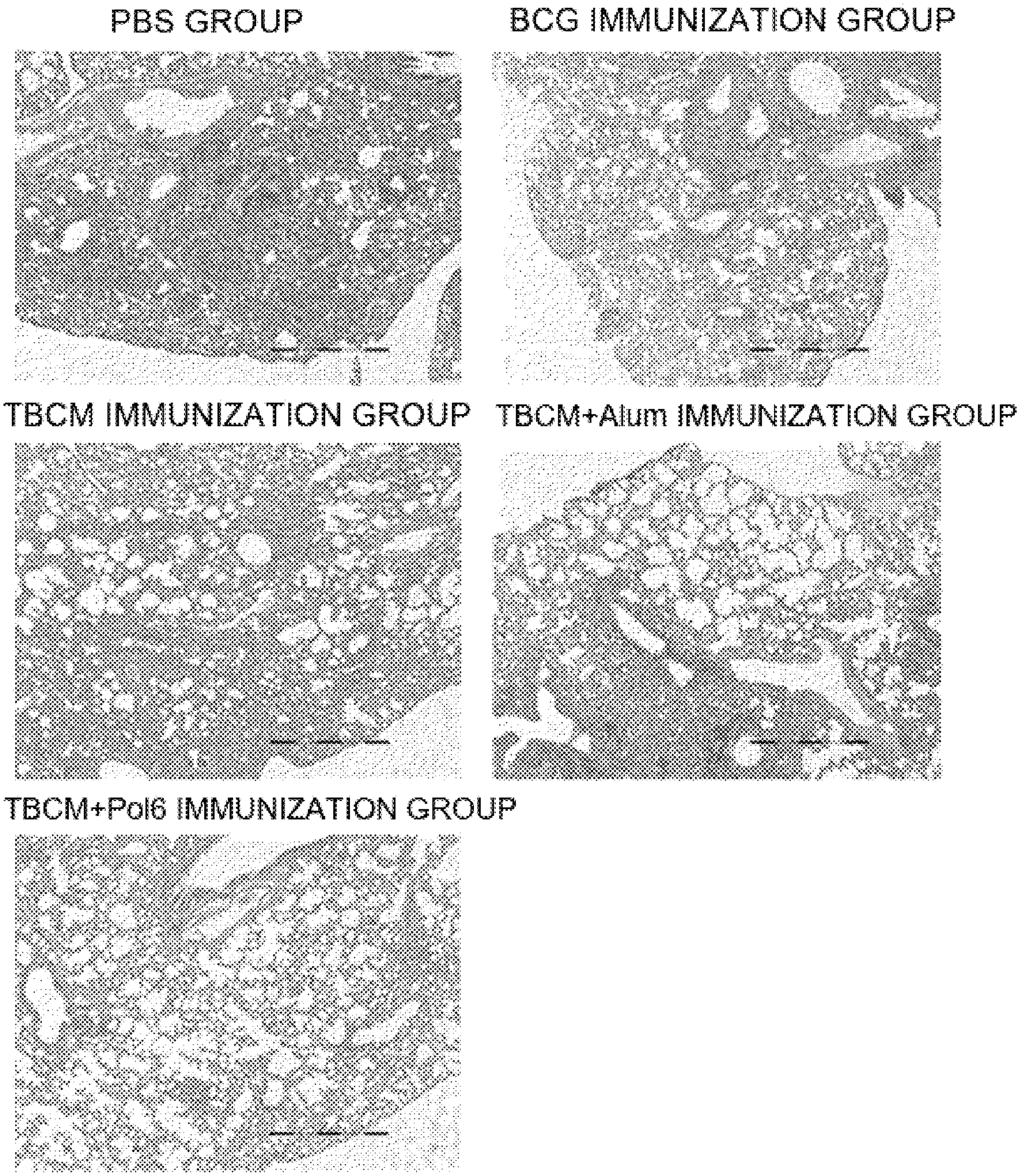

FIG. 50 is a diagram showing photographs of H&E-stained lung tissues of H37Ra-infected mice after immunization with TBCM and various combinations of adjuvants.

Figure 51A:
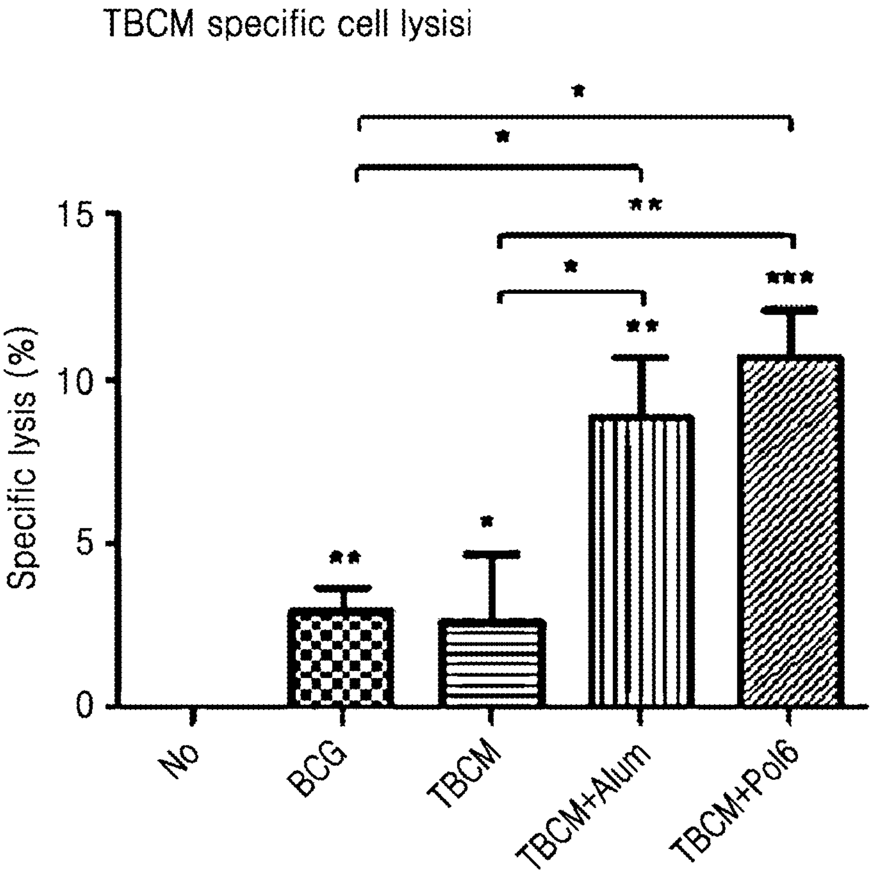
Figure 51B:
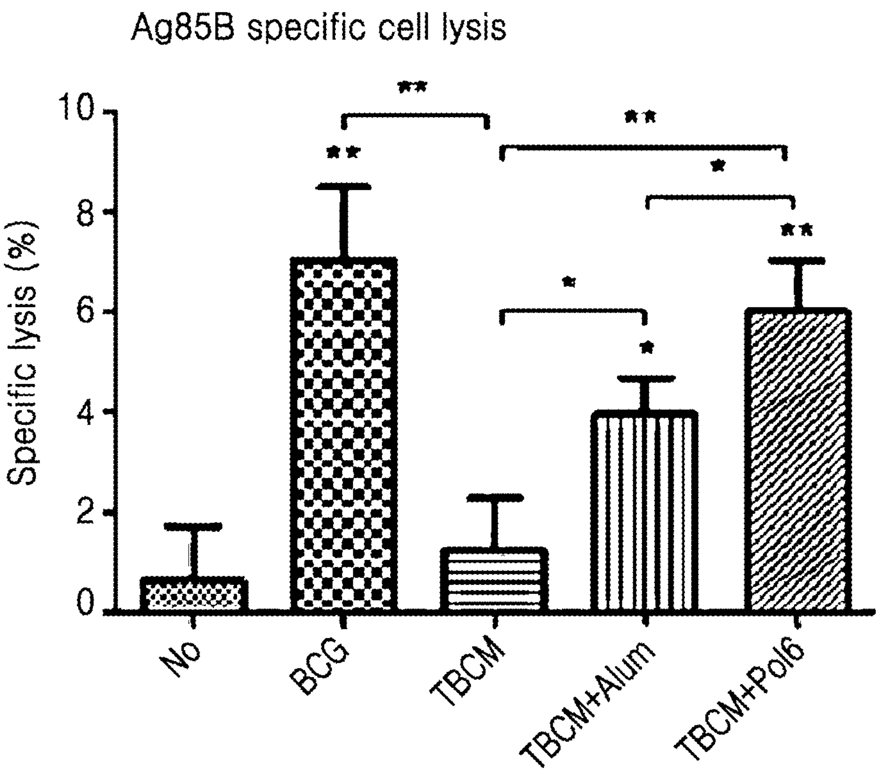

FIG. 51 is a diagram showing results of CTL responses induced by each immunization group. Specifically, (A) of FIG. 51 shows TBCM-specific lysis, and (B) shows Ag85B-specific lysis (statistical significance is tested by Student-t-test, , P<0.01; *, P<0.001).

MODE OF DISCLOSURE

Hereinafter, the present disclosure will be described in more detail through examples. However, these examples are intended to illustrate the present disclosure, and the scope of the present disclosure is not limited to these examples.

EXAMPLE

1. Development of Hepatitis B Virus-Derived Peptide Immune Adjuvant by Using Dendritic Cell Activation Mutants related to the development of a liver disease caused by hepatitis B virus (HBV) of gene type C were screened, and 15, 18, and 21 nucleotide defects at an initiation site of HBV preS1 were found in patients with chronic hepatitis infected with HBV of gene type C2, and the present inventors reported that the nucleotide defects have a major correlation with HBV proliferation and liver disease development in patients.

Figure 1:
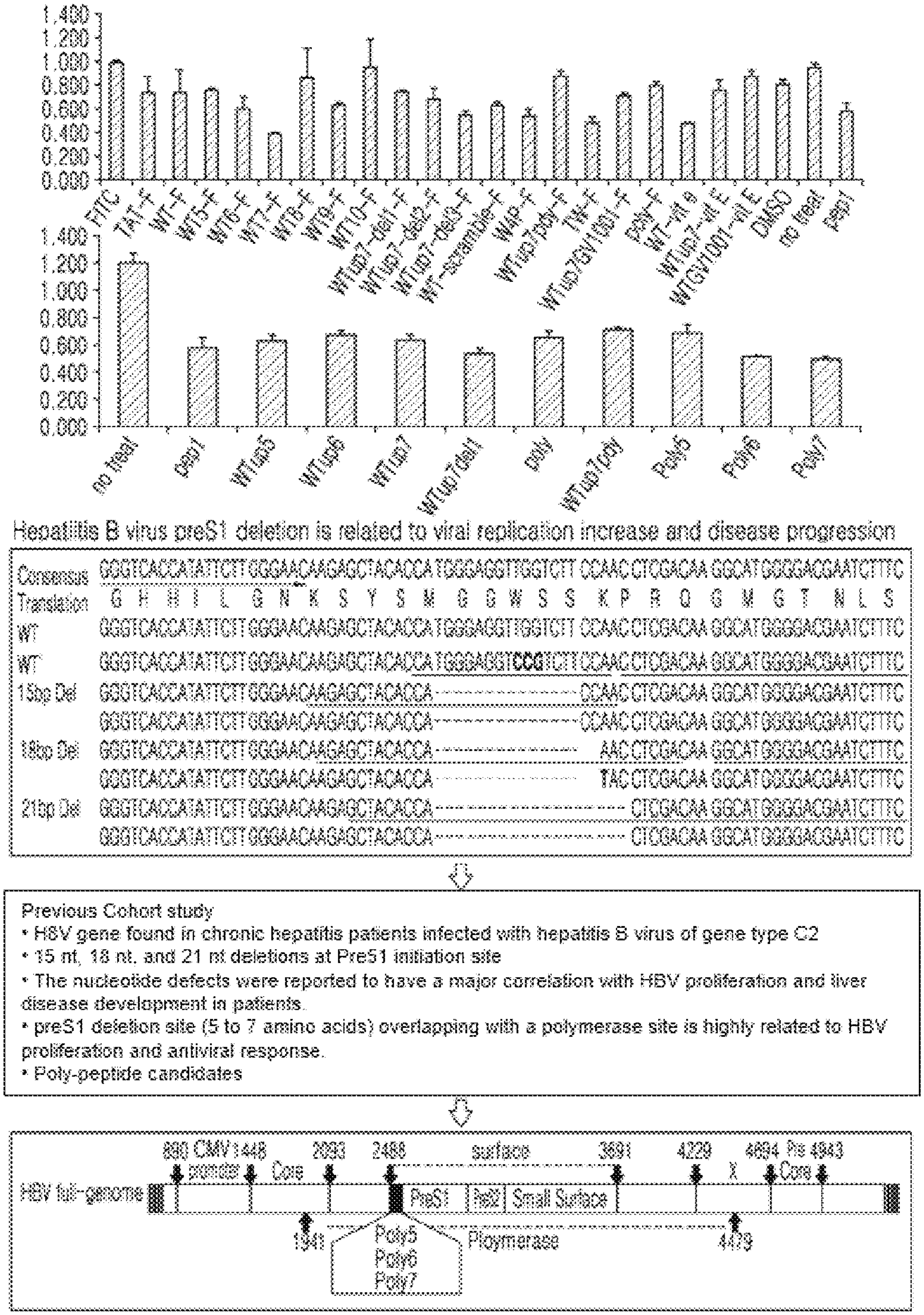
FIG. 1 is a diagram showing processes of screening for HBV-derived vaccine immune adjuvant candidate peptides, and selection and development of Poly6.

Among the screened peptides, it was hypothesized that the preS1 deletion site (5 to 7 amino acids) overlapping with a polymerase site is highly related to HBV proliferation and antiviral response, and polypeptide candidates (Poly5, Poly6 and Poly 7) related thereto were developed. (FIG. 1).

Figure 2:
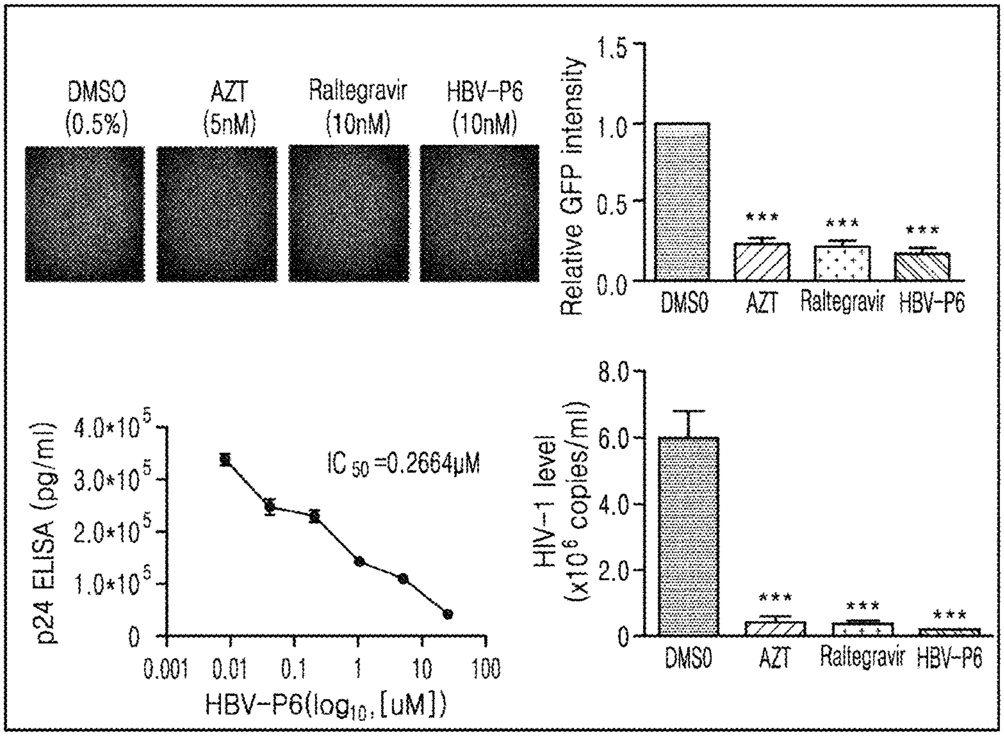
FIG. 2 is a diagram confirming anti-HIV-1 and anti-HBV effects of a hepatitis B virus-derived peptide.
Figure 2:
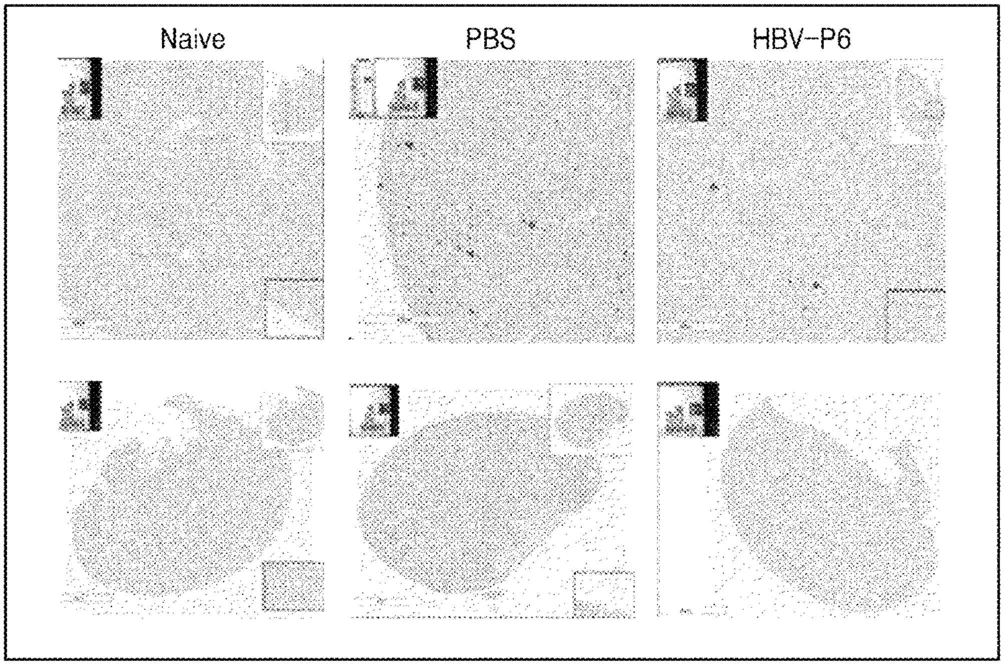

Among the polypeptide candidates Poly5 (GRLVF, SEQ ID NO: 1), Poly6 (GRLVFQ, SEQ ID NO: 2), and Poly7 (GRLVFQT, SEQ ID NO: 3), Poly6 (or Pol6) showed anti-HIV-1 effects and was observed to have antiviral activity on its own, in addition, anti-HBV effects in HBV-carrier mouse models were also observed (hydrodynamic injection) (FIG. 2).

Figure 3:
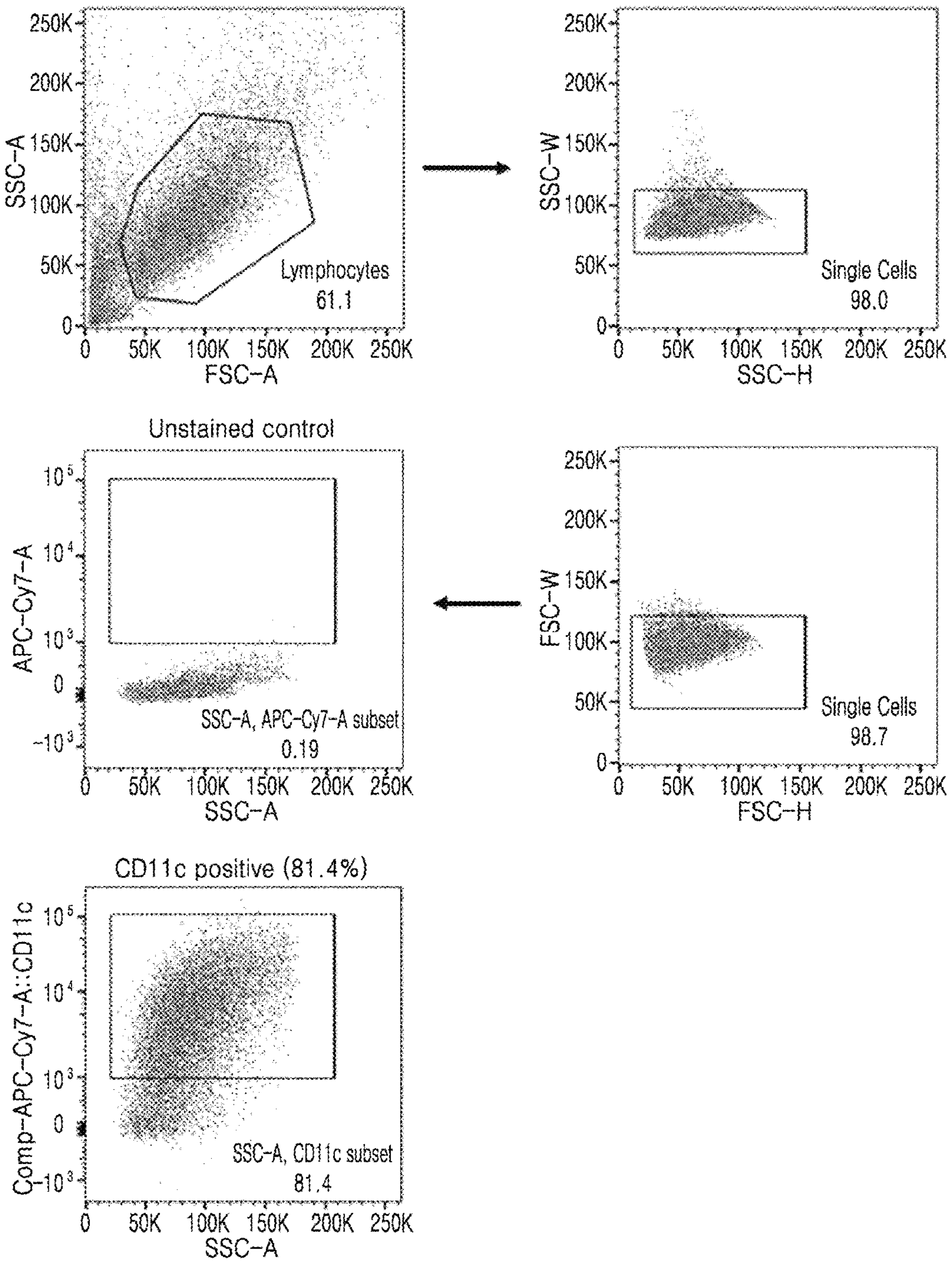
FIG. 3 is a diagram confirming expression levels of CD11c markers in dendritic cells differentiated from mouse bone marrow cells.
Figure 4A:
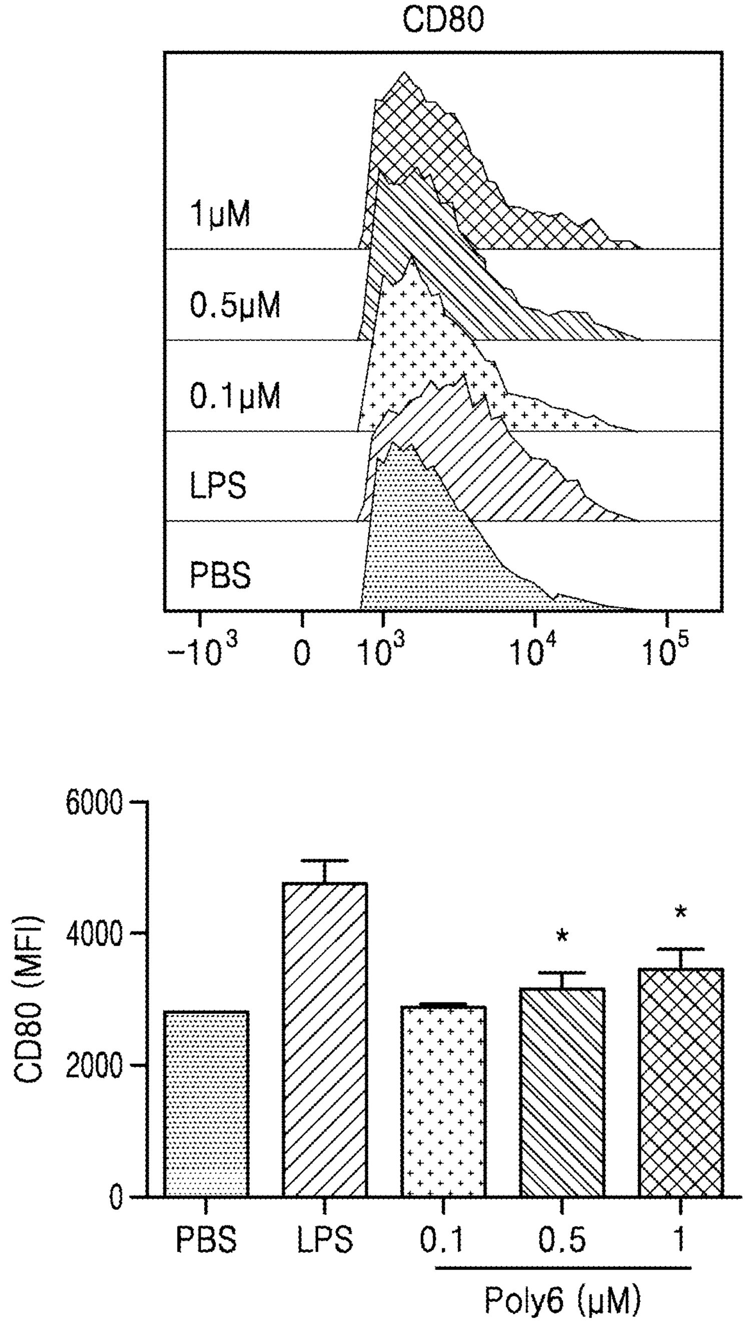
FIG. 4 is a diagram showing measured expressions of maturation markers (A) CD80, (B) CD86, (C) MHC I, and (D) CCR7 in dendritic cells, when Poly6 peptides are treated at different concentrations to the dendritic cells differentiated from mouse bone marrow cells (statistical significance is tested by Student-t-test, *, P<0.05; , P<0.01; *, P<0.001).
Figure 4B:
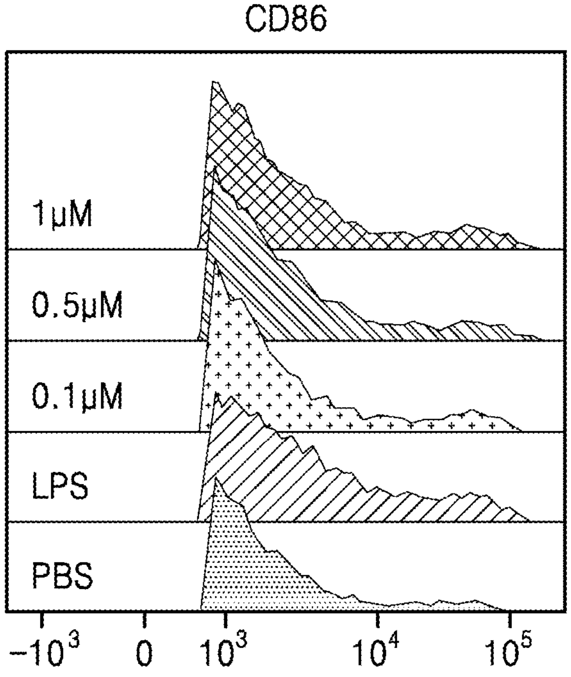
Figure 4B:
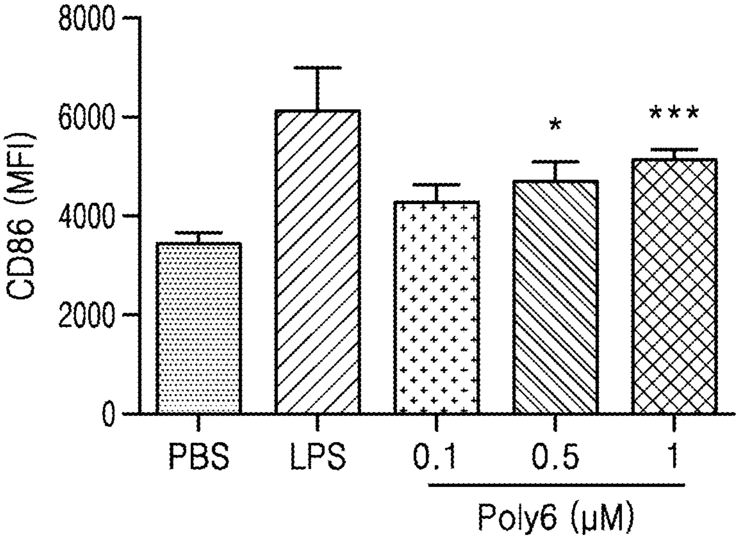
Figure 4C:
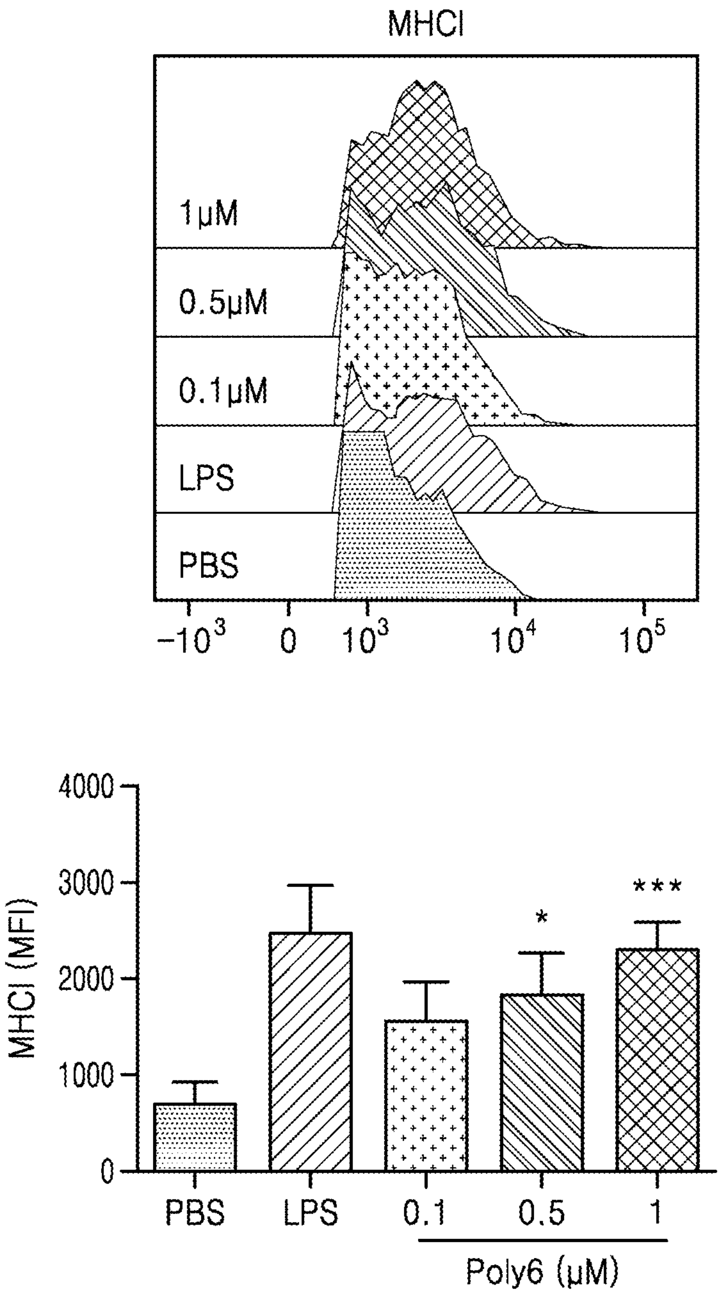
Figure 4D:
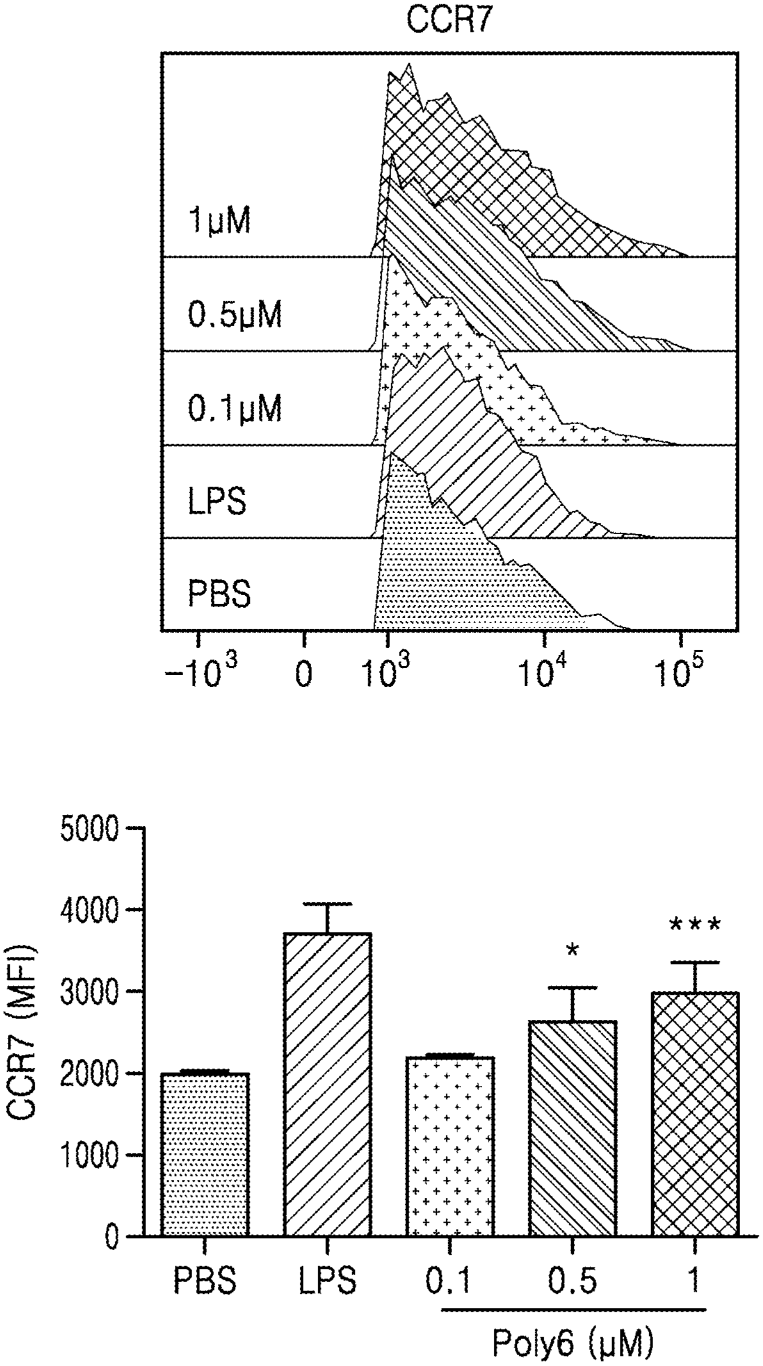

2. Evaluation of Induction of Dendritic Cell Activation by Poly6 Adjuvant (1) Differentiation of Dendritic Cells The femur and tibia of C57BL/6 mice were isolated, and bone marrow cells therein were isolated. The isolated bone marrow cells were cultured in IMDM medium (supplemented with IL-4 and GM-CSF) to induce differentiation of dendritic cells. After culturing for 6 days, dendritic cells having 80% or more of CD11c markers were used in the experiment (FIG. 3).

(2) Confirmation of Expression of Maturation Markers in Dendritic

Cells when HBV-Derived Poly6 Peptides were Treated In order to enhance antiviral effects by inducing an immune response, dendritic cells that activate acquired immunity act as important cells, and thus, whether Poly6 peptides induce maturation of dendritic cells was observed.

Dendritic cells differentiated from mouse bone marrow cells were treated with Poly6 peptides at each concentration of 0.1 μM, 0.5 μM, and 1 μM and cultured for 24 hours, and then expression of representative maturation markers CD80, CD86, and MHC I, and a migration marker CCR7 of dendritic cells were confirmed by fluorescence activated cell sorting (FACS).

As a result, it was confirmed that the expression level of the maturation markers of dendritic cells increased as the concentration of treated Poly6 increased, and through this, it was found that Poly6 peptides stimulate dendritic cells to mature (FIG. 4).

(3) Measurement of Cytokines Secreted by Dendritic Cells when Poly6 Peptides are Treated Secretion of inflammatory cytokines such as TNF-α, IL-6, and IL-12p40 are involved in promoting acquired immune responses, as well as expression of surface maturation markers in dendritic cells activated by Poly6 peptides, and thus, secretion of inflammatory cytokines was also confirmed.

When dendritic cells were treated with Poly6 peptides at concentrations of 0.1 μM, 0.5 μM, and 1 μM for 24 hours, inflammatory cytokines TNF-α, IL-6, and IL-12p40 secreted by dendritic cells were confirmed by ELISA.

Figure 5A:
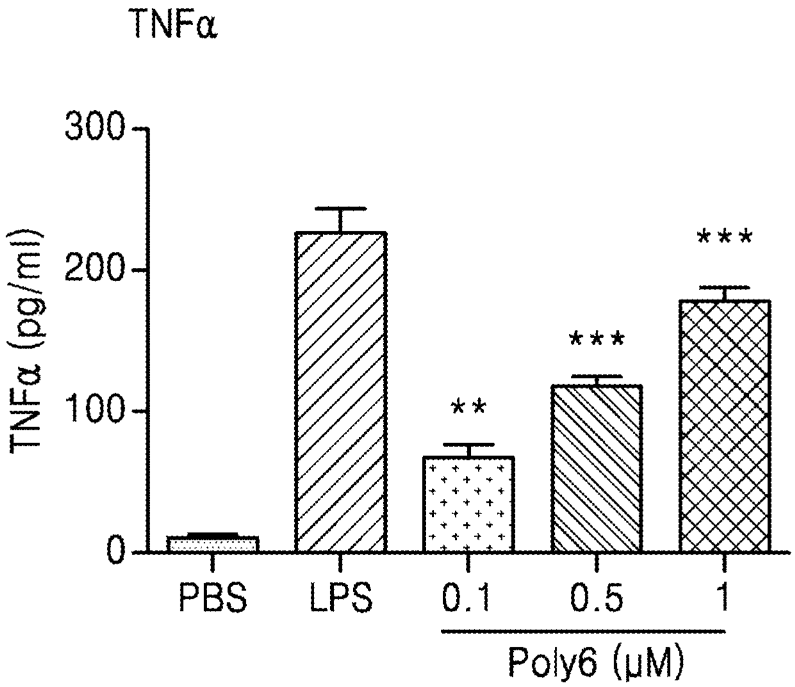
FIG. 5 is a diagram quantifying inflammatory cytokines (A) TNF-α, (B) IL-6, and (C) IL-12p40 of dendritic cells, when Poly6 peptides are treated at different concentrations to the dendritic cells differentiated from mouse bone marrow cells (statistical significance is tested by Student-t-test, *, P<0.05; , P<0.01; *, P<0.001).
Figure 5B:
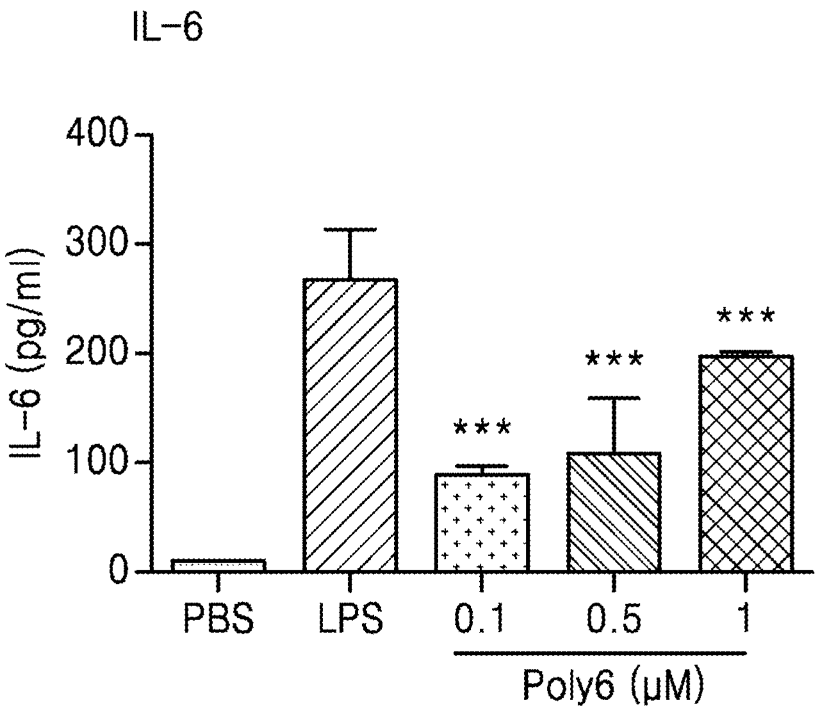
Figure 5C:
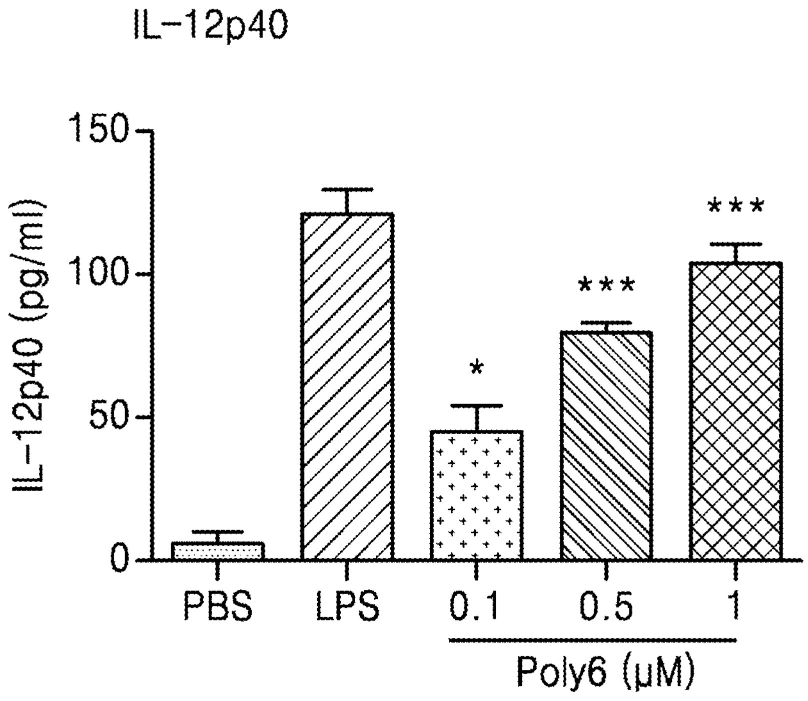

As a result, as the concentration of the treated Poly6 peptides increased, amounts of TNF-α, IL-6, and IL-12p40 secreted by dendritic cells increased, and therefore, it was found that Poly6 peptides stimulate dendritic cells to induce secretion of inflammatory cytokines (FIG. 5).

(4) Confirmation of Migratory Ability of Dendritic Cells when Dendritic Cells Treated with Poly6 Peptides are Injected into Mice Via Footpad Injection As CCR7, a migration marker of dendritic cells activated by Poly6, increased, it was investigated whether dendritic cells migrated to the lymph nodes on their own in mice.

Dendritic cells activated by treatment with Poly6 peptides for 24 hours were fluorescently labeled (CFSE) and injected into C57BL/6 mice by footpad injection, and after 3 days, the inguinal lymph nodes of the mice were extracted to confirm numbers of labeled dendritic cells.

As a result, it was confirmed that numbers of dendritic cells found in the lymph nodes increased statistically significantly when dendritic cells treated with 0.1 μM of Poly6 were injected into mice, compared to when dendritic cells without any treatment were injected. Through this, it was found that Poly6 peptides not only increase expression of surface maturation markers of dendritic cells but also increase migratory ability of dendritic cells in the body (FIG. 6).

3. Evaluation of Immune Induction Ability of Poly6 Adjuvant Combination when Mice are Immunized with Poly6 Adjuvant Combination (1) Presentation of Immunity-Enhancing Effect of Poly6 on DNA Vaccine According to the schedule shown in FIG. 7, mice were immunized once or twice at a 2-week interval (intramuscular injection, IM) using pcDNA3.3-Ag85B:ESAT6 vectors and a combination of the vectors and Poly6. Two weeks after the final immunization, the mice were sacrificed, and immune responses specific to Ag85B were observed in splenocytes and serum. Concentrations of DNA and an adjuvant used in the immunization were as follows.

i) pcDNA3.3-Ag85B:ESAT6 (SEQ ID NO: 6) (50 μg/mouse)
ii) Poly6 (5 μg/mouse)

1) IFN-γ Enzyme-Linked Immunospot (ELISPOT) Assay

Using splenocytes from mice immunized with a combination of pcDNA3.3-Ag85B:ESAT6 DNA and Poly6, expression levels of IFN-γ in response to Ag85B antigen stimulation was confirmed by ELISPOT.

As a result, it was confirmed that in both cases in which immunizations were performed once or twice (mouse sacrificed at week 2 and week 4), the DNA+Poly6 combination increased IFN-γ spots at a statistically significant level compared to when the mice were immunized with DNA alone (FIG. 8).

2) FACS Analysis

Splenocytes of mice immunized with the combination of pcDNA3.3-Ag85B:ESAT6 DNA and Poly6 were stimulated with Ag85B proteins, and then intracellular IFN-γ expression was analyzed by FACS.

As a result, at the week 2 after the immunization, a difference in T cell populations secreting IFN-γ was slight (FIG. 9), but at week 4 after the immunization, a CD4 T cell population secreting IFN-γ was found to be significantly increased by Poly6. When mice were immunized with both DNA and Poly6, CD8+ IFN-γ and T cell population also increased compared to a non-immunized group, but there was no significant difference from a group immunized with DNA alone (FIG. 10).

3) Evaluation of Cytotoxic T Cell (CTL) Activity

Splenocytes (effector cells) of mice immunized with the combination of pcDNA3.3-Ag85B:ESAT6 DNA and Poly6, and MEF cells (H-2b, target cells) stimulated with Ag85B were cultured together for 6 hours at ratios of target:effector cell=1:10, 1:20, and 1:50. Afterwards, cytotoxicity evaluation was conducted by measuring amounts of lactate dehydrogenases (LDH) exposed in the cell culture medium.

As a result, in the group immunized with pcDNA3.3-Ag85B:ESAT6 DNA and Poly6, Ag85B-specific cell lysis was found to be higher than that in the DNA-only immunization group (FIG. 11).

(2) Presentation of Immunity Enhancement Effect of Poly6 on Protein Vaccines

According to the schedule shown in FIG. 12, mice were immunized twice at a 2-week interval (intraperitoneal injection, IP) with a combination of p24 proteins and Poly6 (at each concentration, 1 μg or 5 μg). Two weeks after the final immunization, the mice were sacrificed, and p24-specific immune responses were observed in splenocytes and serum. Concentrations of the proteins and adjuvant used in the immunization were as follows.

i) p24 protein (SEQ ID NO: 7) (30 μg/mouse)
ii) Poly6 (5 μg/mouse)

1) IFN-γ Enzyme-Linked Immunospot (ELISPOT) Assay

Using splenocytes of mice immunized with a combination of p24 proteins and Poly6, expression levels of IFN-γ in response to p24 antigen stimulation were confirmed by using ELISPOT.

As a result, it was confirmed that the group immunized with both p24 and Poly6 increased IFN-γ spots at a statistically significant level compared to the group immunized with p24 proteins alone. In addition, it was confirmed that p24-specific IFN-γ spots increased according to the concentration of Poly6 (FIG. 13).

2) Cytokine Measurement

After splenocytes of mice immunized with the combination of p24 proteins and Poly6 were stimulated with p24 proteins, ELISA was performed for IL-2, IFN-γ. IL-10, IL-1β, IL-6, and TNF-α in the cell culture medium.

As a result, similar to the IFN-γ ELISPOT results, the combination of p24 and Poly6 increased IFN-γ expression compared to immunization with p24-only, and expression levels of IFN-γ increased as the concentration of Poly6 increased. In the remaining cytokines except for IL-10, it was confirmed that expression levels of cytokines increased by Poly6 and as the concentration of Poly6 increased (FIG. 14).

3) Measurement of IgG Expression in Serum

Expression levels of p24-specific IgG2, IgG1, and total IgG in serum of mice immunized with the combination of p24 proteins and Poly6 were evaluated by ELISA.

Expressions of IgG2, IgG1, and total IgG in serum were all increased in the immunization group immunized with a combination including Poly6 compared to the p24-only immunization group, but no difference was observed according to the concentration of Poly6 (FIG. 15).

4) Evaluation of Cytotoxic T Lymphocyte Response (CTL)

Mouse splenocytes (effector cells) immunized with a combination of p24 proteins and Poly6, and P815 cells (H-2d, target cells) stimulated with p24 peptides were cultured together for 6 hours at ratios of target:effector cell=1:10, 1:20, and 1:50. Afterwards, cytotoxicity evaluation was conducted by measuring amounts of lactate dehydrogenases (LDH) exposed in the cell culture medium.

As a result, it was confirmed that immunization with p24 proteins in combination with 5 μg of Poly6 under the culture conditions of 1:50 induced relatively high p24-specific cytotoxicity compared to other immunization methods (FIG. 16).

(3) Presentation of Immunity Enhancement Effect by Using Existing Adjuvant and Poly6 in Combination According to the schedule shown in FIG. 12, mice were immunized twice at a 2-week interval (intraperitoneal injection, IP) with a combination of p24 proteins, Alum and Poly6 (at each concentration, 1 μg or 5 μg). Two weeks after the final immunization, the mice were sacrificed, and p24-specific immune responses were observed in splenocytes and serum. Concentrations of the proteins and adjuvants used in the immunization were as follows.

i) p24 proteins (30 μg/mouse)
ii) Alum (100 μg/mouse)
iii) Poly6 (5 μg/mouse)

1) IFN-γ Enzyme-Linked Immunospot (ELISPOT) Assay

Using splenocytes of mice immunized with a combination of p24 proteins, Alum, and Poly6, expression levels of IFN-γ in response to p24 antigen stimulation were confirmed by ELISPOT.

As a result, a group immunized with p24 and Alum induced IFN-γ spots at a level similar to that of a group immunized with p24 alone. In cases in which mice were immunized with both Poly6 and Alum, when 1 μg of Poly6 was used, there was no significant difference between immunization groups immunized with p24 alone and immunized with p24+Alum, but when immunized with 5 μg of Poly6, the group immunized with both Poly6 and Alum was found to increase IFN-γ spots in a statistically significant level compared to other immunization groups (FIG. 18).

2) Cytokine Measurement

After splenocytes of mice immunized with the combination of p24 proteins and Poly6 were stimulated with p24 proteins, ELISA was performed for TNF-$\alpha$, IFN-$\gamma$. IL-2, IL-6, and IL-10 in the cell culture medium.

As a result, cytokine expression was relatively higher in a group immunized with the combination of p24 and Alum than in a group immunized with p24 alone. However, when immunization was performed by adding Poly6 to the combination of p24 and Alum, the cytokine expression level was further increased, and it was confirmed that the cytokine expression level was generally increased as the concentration of Poly6 increased (FIG. 19).

3) Measurement of IgG Expression in Serum

Expression levels of p24-specific IgG2, IgG1, and total IgG in serum of mice immunized with the combination of p24 proteins, Alum and Poly6 were evaluated by using ELISA.

As a result, the expression of IgG2, IgG1, and total IgG in the serum tended to be relatively increased in a group immunized with an adjuvant, compared to a group immunized with p24 only, but the difference according to use of Alum and Poly6 in combination and the concentration of Poly6 was insignificant. (FIG. 20).

4) Evaluation of Cytotoxic T Lymphocyte Response (CTL)

Mouse splenocytes (effector cells) immunized with a combination of p24 proteins, Alum, and Poly6, and P815 cells (H-2d, target cells) stimulated with p24 peptides were cultured together for 6 hours at ratios of target:effector cell=1:10, 1:20, and 1:50. Afterwards, cytotoxicity evaluation was conducted by measuring amounts of lactate dehydrogenases (LDH) exposed in the cell culture medium.

As a result, in a group immunized with the combination of p24, Alum, and Poly6 under the culture condition of 1:50, p24 specific-cytotoxicity induction ability was found to be increased compared to the group immunized with p24 alone or the combination of p24 and Alum, in addition, cytotoxicity was confirmed to be increased depending on the concentration of Poly6 (FIG. 21).

4) Presentation of S Antigen-Specific Immune Induction Ability, when Poly6 and HBV S Antigens are Used in Combination (Evaluation of Preventive Vaccine Efficacy)

As shown in FIG. 22, 7-week-old C57BL/6 mice were immunized with 10 μg of Poly6 peptides and 10 μg of HBV S proteins twice at a 2-week interval by intraperitoneal injection, and after 2 weeks, expression of surface maturation markers of dendritic cells in splenocytes of the mice were confirmed by FACS.

1) Measurement of IgG Expression in Serum

After immunizing mice with Poly6 in combination with S proteins, serum was obtained through orbital sinus blood sampling at week 2 and week 4, and then whether antibodies against hepatitis B virus surface antigen (HBsAg) were produced was confirmed by IgG ELISA.

As a result, it was confirmed that IgG1, IgG2, and total IgG against S antigens were significantly increased in a group immunized with Src homology 2 domain-containing adapter protein B (SHB) and Poly6, both at week 2 and week 4, and the induction time of the group was also earlier than that of a group immunized with Alum-combined SHB, a common control group, and it was confirmed that at week 2, antibodies against the S antigens were significantly formed only in the group immunized with Poly6-combined SHB. Therefore, potential of S antigens used in combination with Poly6 as a preventive vaccine was confirmed (FIG. 23).

2) Evaluation of Immune Activation Ability of Dendritic Cells in Immunized Mouse Splenocytes Splenocytes from C57BL/6 mice injected with Poly6 and HBV S proteins were isolated and separated into single cells, and expression of surface maturation markers on dendritic cells was confirmed by using FACS.

As a result, it was confirmed that when HBV-derived Poly6 peptides and S proteins were injected together, CD40 and CD86, which are maturation markers of dendritic cells, increased at a statistically significant level compared to untreated mice. Through this, it was found that combined administration of Poly6 peptides and S proteins increases immune activity of dendritic cells in mice (FIG. 24).

3) Confirmation of T Cell Activity in Immunized Mouse Splenocytes

In splenocytes of C57BL/6 mice injected with Poly6 and HBV S proteins, expression of CD40 and CD86, maturation markers of dendritic cells, increased, and it was expected that dendritic cells activated by injection of Poly6 and HBV S proteins induce expression of inflammatory cytokines in helper T cells or cytotoxic T cells.

A ratio of T cells secreting IFN-$\gamma$ was analyzed by using FACS through intracellular cytokine staining in splenocytes of mice administered with Poly6 peptides and HBV S proteins in combination.

As a result, it was confirmed that helper T cells and cytotoxic T cells secreting IFN-$\gamma$ increased in the group administered with HBV-derived Poly6 peptides and S proteins in combination. Through this, it was found that the ratio of T cells secreting inflammatory cytokines in mouse splenocytes increased through the combined administration of Poly6 peptides and HBV S proteins (FIG. 25).

(5) Evaluation of Antiviral Efficacy of S Antigens and Poly6 Used in Combination as a Therapeutic Vaccine 1) Effect of Reducing HBV DNA and HBsAg Antigen in Serum when Poly6 was Co-Injected with S Protein Vaccine in Mice Based on the fact that dendritic cells and T cells are activated when immunizing with Poly6 in combination with S antigens as described above, antiviral ability, which is the ultimate goal of a therapeutic vaccine, was measured. In this regard, the Poly6-combined protein vaccine was administered to transgenic (TG) mice that continuously secreted HBV DNA into the serum. In order to observe differences according to administration methods, S protein vaccine and Poly6 were co-administered to female and male mice via subcutaneous and intraperitoneal injection, respectively, and after 2 weeks and 4 weeks, blood was collected through orbital sinus blood sampling, and the serum, and liver tissues were separated. HBV viral DNA in the serum was extracted from the serum and liver tissues by using a QIAamp DNA Blood kit (QIAGEN).

qPCR was performed by using a primer (SamII S gene, SF/SR, positions 309 to 328) for quantifying HBV, and quantification by using a standard, and group comparison were performed.

In addition, the serum was diluted (1:100 or 1:20), HBsAg ELISA was performed according to the manufacturer's protocol, and secretion amounts of HBsAg antigens in serum were measured by comparing OD values measured with a TECAN device, and antiviral activity was observed.

As a result, it was confirmed that HBsAg and HBV DNA decreased in TG mice co-immunized with Poly6 and S antigens, which showed a more significant difference when administered with Alum, a commercially available immune adjuvant (FIG. 26).

2) Measurement of IgG in Serum

HBsAg-specific IgG2, IgG1, and total IgG in the serum of mice immunized with a combination of proteins and an adjuvant were measured by ELISA.

As a result, IgG1, IgG2, and total IgG were all increased in all TG mouse groups SC or IP injected compared to the groups injected with phosphate buffered saline (PBS), and Poly6 alone, respectively. Through this, it was found that the expression of IgG specific to HBs antigens increased when Poly6 was co-administered with sAg proteins. Even at this time, it was observed that the effect increased more significantly when co-administered with Alum (FIG. 27).

3) Evaluation of Cytokine Expression in Splenocytes

Splenocytes from TG mice co-administered with S proteins and Poly6 were obtained, and expression of IL-2, IFN-γ, and IL-12, which are cytokines secreted into the cell culture medium, was measured by using ELISA.

As a result, it was observed that IL-2, IFN-γ, and IL-2 were significantly increased in TG mice co-administered with Poly6 and S proteins (SHB) compared to groups respectively administered with PBS and S proteins alone. However, cytokines secreted by an antigen challenge were not observed in transgenic (TG) mice (FIG. 28).

4) Measurement of Maturity of Dendritic Cells in Lymphocytes

After co-administration of Poly6 and S proteins to TG mice, the lymph nodes were isolated and separated into single cells, and then maturity of dendritic cells was measured by using FACS.

When Poly6 and S proteins are co-administered to C57BL/6 mice, CD80, CD40, and MHCII, which are markers of dendritic cell activity, were significantly increased in lymphocytes of TG mice, just as immune activity of dendritic cells in splenocytes was increased. Through this, it was found that the co-administration of Poly6 and S proteins increased immune activation ability of dendritic cells even in lymphocytes, which are a secondary immune system (FIG. 29).

5) Histopathological Evaluation of Liver Tissue

Mice to which Poly6 was co-administered with S antigens were sacrificed, and a part of the liver tissue was fixed in formalin. The fixed samples were embedded in paraffin and subjected to hematoxylin-eosin staining (H&E staining). The stained tissue was observed under a microscope to confirm a degree of infiltration of immune cells.

As a result of confirming the H&E staining results, infiltration of immune cells was found in several places in the liver tissue of mice co-administered with S antigens and Poly6 compared to groups respectively administered with PBS and S antigens only. Through this, it was confirmed that activity and migration of immune cells may be further increased when S antigens and Poly6 are co-administered than when the S antigens are administered alone (FIG. 30).

6) Evaluation of T Cell Population Secreting IFN-γ in the Liver Tissue of TG Mice when Poly and S Proteins were Co-Administered By confirming the antiviral activity and the infiltration of immune cells into the liver tissue in serum and liver tissue in TG mice, it was hypothesized that not only activation of dendritic cells, but also activation of the secondary immune system, and ultimately, activation and migration of functional T cells showing antiviral activity would be observed, by co-administration of Poly6 and S antigens.

Liver tissues of TG mice co-administered with Poly6 and S proteins were isolated, made into single cell units, and analyzed by using FACS. As a result, it was found that numbers of CD4 and CD8 T cells secreting IFN-γ in the group co-immunized with Poly6 and S proteins were significantly increased compared to groups respectively immunized with PBS and Poly6 alone. However, no significant difference was observed according to an additional co-administration of Alum. Through this, it was confirmed that Poly6 may induce activation of functional T cells showing actual antiviral activity in accordance with the original main purpose of developing a therapeutic vaccine using a Poly6 peptide immune adjuvant and S proteins in combination (FIG. 31).

7) Evaluation of Effector T Cell Population when Co-Immunizing with

Poly6 and S Proteins In addition to increasing functional T cells and IFN-γ expression, the combination of Poly6 with S proteins was confirmed to activate effector memory T cells ($CD44^{high}$ $CD62L^{low}$), which are capable of functioning upon antigen infiltration with a memory of an antigenic infiltration long after the vaccination, by isolating liver tissues and by using FACS.

8) Increased Expression of IFNγ-Secreting T Cells in Peripheral Blood Mononuclear Cells (PBMC) by Treatment with Poly6

As an increase of immune activation ability of dendritic cells, activation of functional T cells, and activation of memory function of T cells due to treatment of Poly6 were confirmed, in order to confirm whether such functions are actually exhibited in human cells, peripheral blood mononuclear cells (PBMC) were extracted, and treated with IL-2 cytokines for three days for T cell expansion, and then, Poly6 was treated at various concentrations, and activation of T cells was measured.

As a result, treatment with Poly6 significantly increased IFN-γ-expressing T cells compared to a group treated with PBS, and a concentration-dependent trend was also observed. Therefore, immune activation function was observed in human cells as well as in cell units and mouse animal experiments, and this reconfirmed that Poly6 may be a great advantage in deriving clinically significant results in the future vaccine development (FIG. 33).

4. Confirmation of Immune Enhancement Effect by Combined Treatment of Pol6 (or Poly6) with *Mycobacterium tuberculosis* Chorismate Mutase (TBCM)

(1) Preparation and Confirmation of *Mycobacterium tuberculosis* Chorismate Mutase (TBCM) Protein Expression Vector A polynucleotide sequence encoding a TBCM (Rv1885c) protein of *Mycobacterium tuberculosis* of SEQ ID NO: 4 was amplified by using genomic DNA of *Mycobacterium tuberculosis* as a template. Thereafter, the polynucleotide sequence was cloned into a pET28a expression vector (SEQ ID NO: 5; His tag included), and the protein was expressed and purified in *E. coli* to obtain TBCM proteins of about 25 kD (FIG. 34).

(2) Evaluation of TBCM- and Tuberculosis-Specific Immune Induction Ability when Mice are Immunized with TBCM and Pol6

1) Results of TBCM-Specific Immune Induction Ability by Co-Immunization (SC) of TBCM Proteins and Pol6

After immunizing (subcutaneous injection, SC) mice twice at a 2-week interval by using TBCM and various adjuvant combinations (TBCM alone, TBCM+Alum, TBCM+Pol6, TBCM+Alum+Pol6) according to the schedule shown in FIG. 35, the mice were sacrificed, and TBCM-specific immune responses were observed in splenocytes and serum. Concentrations of the TBCM proteins and adjuvants were as follows.

i) TBCM (10 μg/mouse)
ii) Alum (100 μg/mouse)
iii) Pol6 (5 μg/mouse)

① IFN-γ Enzyme-Linked Immunospot (ELISPOT) Assay

By using splenocytes of mice immunized with each combination of proteins and adjuvants, expression levels of IFN-γ in response to TBCM antigenic stimulation was confirmed by ELISPOT.

As a result, it was confirmed that the TBCM+Pol6 combination increased IFN-γ spots at a statistically significant level compared to TBCM alone and the TBCM+Alum combination. In addition, when immunized with the combination of TBCM+Alum+Pol6, it was confirmed that an expression level of TBCM-specific IFN-γ was the highest (FIG. 36).

② Cytokine Measurement

Splenocytes of mice immunized with each combination of proteins and adjuvants were stimulated with TBCM proteins, and then ELISA was performed for IFN-γ, IL-12, TNF-α, and IL-10 in the cell culture medium.

As a result, it was confirmed that expression of IFN-γ and IL-12, which are cytokines important for protective immunity, in mouse splenocytes immunized with the TBCM+Pol6 combination increased with statistical significance than with TBCM alone and with a TBCM+Alum combination (FIG. 37).

In addition, when immunized with the TBCM+Alum+Pol6 combination, expression of IFN-γ and IL-12 was higher than with other combinations (FIG. 37).

For TNF-α, an inflammatory cytokine, and IL-10, an anti-inflammatory cytokine, the TBCM+Pol6 combination showed similar levels of expression to TBCM alone and the TBCM+Alum combination, and splenocytes immunized with the TBCM+Alum+Pol6 combination, exhibited higher TNF-α and IL-10 expression than splenocytes immunized with other combinations (FIG. 37).

③ Measurement of IgG in Serum

TBCM-specific IgG2, IgG1, and total IgG in serum of mice immunized with each combination of proteins and adjuvants were evaluated by ELISA.

For comparison of IgG2 expression, IgG2 expression increased in a group co-immunized with an adjuvant compared to a group immunized with TBCM alone, and IgG2 expression relatively increased when immunized with a TBCM+Pol6 combination than when immunized with TBCM+Alum, but there was no statistical significance. In addition, the TBCM+Alum+Pol6 combination showed the highest IgG2 expression level with statistical significance compared to all other immunization groups except for the immunization group immunized with a TBCM+Pol6 combination (FIG. 38).

For IgG1, immunization with the TBCM+Pol6 combination showed a level similar to immunization with TBCM alone, and relatively low IgG1 expression compared to immunization with the TBCM+Alum combination. As in the previous comparison of IgG2 expression, when TBCM+Alum+Pol6 were combined, expression of IgG1 tended to increase compared to other immunization groups (FIG. 38).

As IgG2 is known to be associated with the Th1 immune response and IgG1 is associated with the Th2 immune response, increased IgG2 expression and similar or lower IgG1 expression when immunizing with a combination of TBCM+Pol6, compared to when immunizing with TBCM alone and immunizing with TBCM+Alum, means Th1 biased immune responses are increased by the combination of TBCM+Pol6.

2) Results of Measuring TBCM-Specific Immune Induction Ability of Co-Immunization (IN) of TBCM Proteins and Pol6

After immunizing mice twice at a 2-week interval according to the schedule shown in FIG. 39 (intranasal injection, IN), by using a combination of TBCM and Alum or a combination of TBCM, Alum, and additional Pol6, the mice were sacrificed, and TBCM-specific immune responses were observed in splenocytes, pneumocytes, bronchoalveolar lavage (BAL) fluid, and serum. Concentrations of the TBCM proteins and adjuvants were as follows.

i) TBCM (10 μg/mouse)
ii) Alum (100 μg/mouse)
iii) Pol6 (5 μg/mouse)

① IFN-γ Enzyme-Linked Immunospot (ELISPOT) Assay

By using splenocytes and pneumocytes immunized with a combination of TBCM and Alum, or a combination of TBCM, Alum, and additional Pol6, expression levels of IFN-γ in response to TBCM antigenic stimulation was confirmed by using ELISPOT.

As a result, it was confirmed that TBCM-specific IFN-γ was increased in all cells by immunization with TBCM+Alum or TBCM+Alum+Pol6 compared to the PBS group. However, the TBCM+Alum+Pol6 immunization group in splenocytes, and the TBCM+Alum immunization group in pneumocytes showed the highest IFN-γ expression (FIG. 40).

② Cytokine Measurement

Splenocytes and pneumocytes of mice immunized with a combination of TBCM and Alum, or a combination of TBCM, Alum, and additional Pol6 were stimulated with TBCM proteins, and then ELISA was performed for IFN-γ, IL-12, IL-17, and IL-10 in the cell culture medium. In addition, IL-12 ELISA was performed in BAL fluid.

As a result, in splenocytes, similar to the IFN-γ ELISPOT results, it was confirmed that expression levels of IFN-γ, IL-12, and IL-17 were increased by the TBCM+Alum+Pol6 immunization group with statistical significance compared to the TBCM+Alum immunization group (FIG. 41). In pneumocytes, the TBCM+Alum immunization group increased expression of IFN-γ and IL-17 compared to the TBCM+Alum+Pol6 immunization group, but there was no statistical significance (FIG. 42).

For IL-10, an anti-inflammatory cytokine, the highest expression was shown by TBCM+Alum immunization in both splenocytes and pneumocytes (FIGS. 41 and 42).

In addition, only IL-12 expression levels were confirmed in BAL fluid, and the expression was increased at a statistically significant level compared to a PBS group in both TBCM+Alum and TBCM+Alum+Pol6 immunization groups, but there was no difference between the two groups (FIG. 43).

③ Measurement of IgG and IgA Expression in Serum and BAL Fluid

Expression of TBCM-specific IgG2, IgG1, total IgG, and IgA in serum and BAL fluid of mice immunized with a combination of TBCM and Alum, or a combination of TBCM, Alum, and additional Pol6 were evaluated by ELISA.

Expression of IgG2, IgG1, total IgG, and IgA in serum was increased in both groups immunized with TBCM+Alum, and TBCM+Alum+Pol6, but the TBCM+Alum+Pol6 group showed a relatively higher expression pattern (FIG. 44).

In addition, for IgA, which plays an important role in mucosal immunity, IgA expression was increased in both immunization groups in BAL fluid (FIG. 44).

Evaluation of Defense Induction Ability Against Tuberculosis by Co-Immunization of TBCM Proteins and Pol6

After immunizing mice twice at a 2-week interval according to the schedule shown in FIG. 45 (subcutaneous injection, SC) by using combinations of TBCM and various adjuvants (TBCM alone, TBCM+Alum, TBCM+Pol6, TBCM+Alum+Pol6), the mice were infected with a H37Ra strain (intranasal injection, IN). At week 4 after the infection, the mice were sacrificed, and immune responses specific to TBCM and Ag85B, a tuberculosis antigen, were observed in splenocytes and serum, and numbers of H37Ra bacteria (CFU) in organs, and inflammatory responses in lung tissues were confirmed by using hematoxylin and eosin (H&E) staining. A group immunized (SC) with *Bacillus* Calmette-Guerin (BCG) was selected as a comparison group. Concentrations of TBCM proteins and adjuvants and numbers of BCG bacteria, used for the immunization, were as follows.

i) TBCM (10 μg/mouse)
ii) Alum (100 μg/mouse)
iii) Pol6 (5 μg/mouse)
iv) BCG ($1\times10^6$ CFU/mouse)

① Cytokine Measurement

Splenocytes of mice immunized with each combination of proteins and adjuvants and infected with H37Ra were stimulated with TBCM and Ag85B proteins, and then ELISA was performed for IFN-γ, TNF-α, and IL-10 the in cell culture medium.

As a result, when stimulated with TBCM, it was confirmed that expression of IFN-γ was increased with statistical significance by immunization with a combination of TBCM+Pol6, compared to immunization with BCG, TBCM alone, and TBCM+Alum. On the other hand, when stimulating with Ag85B, it was confirmed that immunization with the TBCM+Alum combination increased the expression of IFN-γ compared to immunization with BCG, TBCM alone, and a TBCM+Pol6 combination (FIG. 46A).

For IL-12, when stimulated with TBCM and Ag85B, TBCM+Pol6 and TBCM+Alum groups showed an almost similar increase in IL-12 expression compared to other immunization groups (FIG. 46B).

For TNF-α, similar to the tendency of IL-12, TBCM+Pol6 and TBCM+Alum groups showed an almost similar increase in TNF-α expression compared to other immunization groups (FIG. 47A).

For IL-10, an anti-inflammatory cytokine, maybe because immune responses were observed after infection with *Mycobacterium tuberculosis*, all immunization groups showed similar aspects with no significant difference except for the non-immunized group (FIG. 47B).

② Measurement of IgG in Serum

Expression of IgG2, IgG1 and total IgG specific to TBCM and Ag85B proteins in serum of mice, which are immunized with a combination of TBCM proteins and adjuvants and infected with *Mycobacterium tuberculosis*, was evaluated and confirmed by ELISA.

As a result, when TBCM-specific IgG expression pattern was observed, the IgG2 expression was increased with statistical significance in the group immunized with the TBCM+Pol6 combination, compared to other immunization groups, and for IgG1, similar levels of expression were observed in all immunization groups other than the group immunized with BCG. In general, it was confirmed that an expression level of TBCM-specific IgG was the highest in the group immunized with TBCM+Pol6, by observing an expression level of total IgG, but there was no statistically significant difference with the TBCM+Alum immunization group (FIG. 48).

When expression patterns of IgG specific to a tuberculosis antigen Ag85B was observed, expression of IgG2 and IgG1 was the highest by BCG immunization. It was confirmed that immunization with TBCM+Pol6 also induced high IgG2 expression, next to BCG immunization. In addition, it was confirmed from the total IgG results that the TBCM+Pol6 immunization group induced expression of Ag85B-specific IgG at a level similar to that of the BCG immunization group (FIG. 48).

③ Confirmation of CFU in Organs

After infecting mice immunized with various combinations of TBCM and adjuvants with H37Ra bacteria (FIG. 45), the mice were sacrificed, and the lungs were homogenized and diluted in PBS by an appropriate dilution factor. A portion of each dilution was spread on a 7H10 solid medium (supplemented with OADC), and then cultured for about 4 weeks in a incubator at 37° C., and 5% $CO_2$. Thereafter, numbers of grown colonies were confirmed and colony forming units (CFU) were calculated.

When CFUs were calculated in the lungs, the CFUs of all immunized groups were decreased compared to the non-immunized group, but the CFUs of the groups respectively immunized by BCG, TBCM+Alum and TBCM+Pol6 was the lowest, and no difference among the three groups was seen (FIG. 49). The result of reducing CFUs of infected H37Ra to a level similar to that when immunized with BCG, which is currently used as a tuberculosis vaccine, indicates possibility of developing a tuberculosis vaccine with TBCM proteins.

④ Histopathological Evaluation of Lung Tissue

After infecting mice immunized with various combinations of TBCM and adjuvants with H37Ra bacteria (FIG. 45), the mice were sacrificed and some parts of the lung tissue were fixed in formalin. The fixed samples were embedded in paraffin and subjected to hematoxylin-eosin staining (H&E staining). The stained tissue was observed under a microscope to confirm differences in inflammatory response.

As a result of confirming H&E staining results, inflammation tended to be alleviated in all immunization groups in general compared to the group only H37Ra is infected, (decreased number of cells in tissue and reduction in thickness of alveolar septa), but alleviation of inflammation in the TBCM+Pol6 group tended to be the highest (FIG. 50).

4) Evaluation of Cytotoxic T Lymphocyte Response (CTL)

Mouse splenocytes (effector cells) immunized with combinations of TBCM and various adjuvants and then infected with H37Ra, and P815 cells (H-2d, target cells) stimulated with Ag85B and TBCM proteins were cultured together for 6 hours. Afterwards, cytotoxicity evaluation was conducted by measuring amounts of lactate dehydrogenases (LDH) exposed in the cell culture medium.

As a result, CTL responses to TBCM were increased in TBCM+Alum and TBCM+Pol6 groups, and although a CTL response to Ag85B was the highest in a BCG group, Ag85B-specific cell lysis was higher in the TBCM+Pol6 group than in other immunization groups (FIG. 51).

The invention claimed is:

1. A method of enhancing immunity comprising administering a polypeptide consisting of the amino acid sequence of SEQ ID NO: 2, and DNA or an antigen to a subject in need thereof, wherein the DNA comprises at least one selected from the group consisting of an expression vector encoding a chorismate mutase, an expression vector encoding an Ag85B protein, an expression vector encoding a p24 protein, and an expression vector encoding an HBV S protein, and wherein the antigen comprises at least one selected from the group consisting of a chorismate mutase, an Ag85B protein, a p24 protein, and an HBV S protein.

2. The method of claim 1, further comprising administering an immune adjuvant to the subject.

3. The method of claim 1, wherein the immune adjuvant is at least one selected from the group consisting of aluminum salts (Alum), CpG oligodeoxynucleotides (ODNs), granulocyte-macrophage colony-stimulating factor (GM-CSF), interleukin-12 (IL-12), poly(I:C), monophosphoryl Lipid A (MPA), AS01 (liposome mixed with monophosphoryl lipid A and saponin QS-21), IC31 (oligo nucleotide and cationic peptide), and CFA01 (cationic liposome.

4. The method of claim 1, wherein the DNA or the antigen is derived from at least one selected from the group consisting of human immunodeficiency virus (HIV), hepatitis B virus (HBV), and *Mycobacterium tuberculosis*.

5. The method of claim 1, wherein the method is for reducing a risk of at least one infection caused by a pathogen selected from the group consisting of human immunodeficiency virus (HIV), hepatitis B virus (HBV), and *Mycobacterium tuberculosis*.

6. The method of claim 1, wherein the method is for reducing a risk of at least one disease selected from the group consisting of liver diseases, acquired immune deficiency syndrome (AIDS), and tuberculosis.

7. A method of reducing a risk of at least one disease selected from the group consisting of liver diseases, acquired immune deficiency syndrome (AIDS), and tuberculosis, comprising administering a polypeptide consisting of the amino acid sequence of SEQ ID NO: 2, and DNA or an antigen to a subject in need thereof, wherein the DNA comprises at least one selected from the group consisting of an expression vector encoding a chorismate mutase, an expression vector encoding an Ag85B protein, an expression vector encoding a p24 protein, and an expression vector encoding an HBV S protein, and wherein the antigen comprises at least one selected from the group consisting of a chorismate mutase, an Ag85B protein, a p24 protein, and an HBV S protein.

8. The method of claim 7, further comprising administering an immune adjuvant.

9. The method of claim 8, wherein the immune adjuvant is at least one selected from the group consisting of aluminum salts (Alum), CpG oligodeoxynucleotides (ODNs), granulocyte-macrophage colony-stimulating factor (GM-CSF), interleukin-12 (IL-12), poly(I:C), monophosphoryl Lipid A (MPA), AS01 (liposome mixed with monophosphoryl lipid A and saponin QS-21), IC31 (oligo nucleotide and cationic peptide), and CFA01 (cationic liposome.

10. The method of claim 7, wherein the DNA or the antigen may be derived from at least one selected from the group consisting of human immunodeficiency virus (HIV), hepatitis B virus (HBV), and *Mycobacterium tuberculosis.*

11. The method of claim 7, wherein the method is for reducing a risk of infection caused by a pathogen selected from the group consisting of human immunodeficiency virus (HIV), hepatitis B virus (HBV), and *Mycobacterium tuberculosis.*

* * * * *

SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: poly5 peptide

<400> SEQUENCE: 1

Gly Arg Leu Val Phe
1               5

<210> SEQ ID NO 2
<211> LENGTH: 6
<212> TYPE: PRT
<213> ORGANISM: Artificial Sequence
<220> FEATURE:
<223> OTHER INFORMATION: poly6 peptide

<400> SEQUENCE: 2

Gly Arg Leu Val Phe Gln
1               5

<210> SEQ ID NO 3
<211> LENGTH: 7
<212> TYPE: PRT
<213> ORGANISM: Artificial Sequence
<220> FEATURE:
<223> OTHER INFORMATION: poly7 peptide

<400> SEQUENCE: 3

Gly Arg Leu Val Phe Gln Thr
1               5

<210> SEQ ID NO 4
<211> LENGTH: 199
<212> TYPE: PRT
<213> ORGANISM: Mycobacterium tuberculosis

<400> SEQUENCE: 4

Met Leu Thr Arg Pro Arg Glu Ile Tyr Leu Ala Thr Ala Val Ser Ile
1               5                   10                  15

Gly Ile Leu Leu Ser Leu Ile Ala Pro Leu Gly Pro Pro Leu Ala Arg
            20                  25                  30

Ala Asp Gly Thr Ser Gln Leu Ala Glu Leu Val Asp Ala Ala Ala Glu
        35                  40                  45

Arg Leu Glu Val Ala Asp Pro Val Ala Ala Phe Lys Trp Arg Ala Gln
    50                  55                  60

Leu Pro Ile Glu Asp Ser Gly Arg Val Glu Gln Gln Leu Ala Lys Leu
65                  70                  75                  80

Gly Glu Asp Ala Arg Ser Gln His Ile Asp Pro Asp Tyr Val Thr Arg
                85                  90                  95

Val Phe Asp Asp Gln Ile Arg Ala Thr Glu Ala Ile Glu Tyr Ser Arg
            100                 105                 110

Phe Ser Asp Trp Lys Leu Asn Pro Ala Ser Ala Pro Pro Glu Pro Pro
        115                 120                 125

Asp Leu Ser Ala Ser Arg Ser Ala Ile Asp Ser Leu Asn Asn Arg Met
    130                 135                 140

Leu Ser Gln Ile Trp Ser His Trp Ser Leu Leu Ser Ala Pro Ser Cys
145                 150                 155                 160

```
Ala Ala Gln Leu Asp Arg Ala Lys Arg Asp Ile Val Arg Ser Arg His
                165                 170                 175

Leu Asp Ser Leu Tyr Gln Arg Ala Leu Thr Thr Ala Thr Gln Ser Tyr
            180                 185                 190

Cys Gln Ala Leu Pro Pro Ala
        195


<210> SEQ ID NO 5
<211> LENGTH: 246
<212> TYPE: PRT
<213> ORGANISM: Artificial Sequence
<220> FEATURE:
<223> OTHER INFORMATION: TBCM expression vector(pET28a)

<400> SEQUENCE: 5

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Met Leu Thr Arg Pro Arg Glu Ile Tyr Leu Ala Thr Ala Val
        35                  40                  45

Ser Ile Gly Ile Leu Leu Ser Leu Ile Ala Pro Leu Gly Pro Pro Leu
    50                  55                  60

Ala Arg Ala Asp Gly Thr Ser Gln Leu Ala Glu Leu Val Asp Ala Ala
65                  70                  75                  80

Ala Glu Arg Leu Glu Val Ala Asp Pro Val Ala Ala Phe Lys Trp Arg
                85                  90                  95

Ala Gln Leu Pro Ile Glu Asp Ser Gly Arg Val Glu Gln Gln Leu Ala
            100                 105                 110

Lys Leu Gly Glu Asp Ala Arg Ser Gln His Ile Asp Pro Asp Tyr Val
        115                 120                 125

Thr Arg Val Phe Asp Asp Gln Ile Arg Ala Thr Glu Ala Ile Glu Tyr
    130                 135                 140

Ser Arg Phe Ser Asp Trp Lys Leu Asn Pro Ala Ser Ala Pro Pro Glu
145                 150                 155                 160

Pro Pro Asp Leu Ser Ala Ser Arg Ser Ala Ile Asp Ser Leu Asn Asn
                165                 170                 175

Arg Met Leu Ser Gln Ile Trp Ser His Trp Ser Leu Leu Ser Ala Pro
            180                 185                 190

Ser Cys Ala Ala Gln Leu Asp Arg Ala Lys Arg Asp Ile Val Arg Ser
        195                 200                 205

Arg His Leu Asp Ser Leu Tyr Gln Arg Ala Leu Thr Thr Ala Thr Gln
    210                 215                 220

Ser Tyr Cys Gln Ala Leu Pro Pro Ala Lys Leu Ala Ala Ala Leu Glu
225                 230                 235                 240

His His His His His His
                245


<210> SEQ ID NO 6
<211> LENGTH: 6670
<212> TYPE: DNA
<213> ORGANISM: Artificial Sequence
<220> FEATURE:
<223> OTHER INFORMATION: pcDNA3.3-Ag85B:ESAT6 expression vector

<400> SEQUENCE: 6

gttaggcgtt ttgcgctgct tcgcgatgta cgggccagat atacgcgttg acattgatta     60
```

-continued

```
ttgactagtt attaatagta atcaattacg gggtcattag ttcatagccc atatatggag    120
ttccgcgtta cataacttac ggtaaatggc ccgcctggct gaccgcccaa cgacccccgc    180
ccattgacgt caataatgac gtatgttccc atagtaacgc caatagggac tttccattga    240
cgtcaatggg tggagtattt acggtaaact gcccacttgg cagtacatca agtgtatcat    300
atgccaagta cgccccctat tgacgtcaat gacggtaaat ggcccgcctg gcattatgcc    360
cagtacatga ccttatggga ctttcctact tggcagtaca tctacgtatt agtcatcgct    420
attaccatgg tgatgcggtt ttggcagtac atcaatgggc gtggatagcg gtttgactca    480
cggggatttc caagtctcca ccccattgac gtcaatggga gtttgttttg gcaccaaaat    540
caacgggact ttccaaaatg tcgtaacaac tccgccccat tgacgcaaat gggcggtagg    600
cgtgtacggt gggaggtcta tataagcaga gctcgtttag tgaaccgtca gatcgcctgg    660
agacgccatc cacgctgttt tgacctccat agaagacacc gggaccgatc cagcctccgg    720
actctagagg atcgaaccct tatgacagac gtgagccgaa agattcgagc ttggggacgc    780
cgattgatga tcggcacggc agcggctgta gtccttccgg gcctggtggg gcttgccggc    840
ggagcggcaa ccgcgggcgc gttctcccgg ccggggctgc cggtcgagta cctgcaggtg    900
ccgtcgccgt cgatgggccg cgacatcaag gttcagttcc agagcggtgg gaacaactca    960
cctgcggttt atctgctcga cggcctgcgc gcccaagacg actacaacgg ctgggatatc   1020
aacaccccgg cgttcgagtg gtactaccag tcgggactgt cgatagtcat gccggtcggc   1080
gggcagtcca gcttctacag cgactggtac agcccggcct gcggtaaggc tggctgccag   1140
acttacaagt gggaaacctt cctgaccagc gagctgccgc aatggttgtc cgccaacagg   1200
gccgtgaagc ccaccggcag cgctgcaatc ggcttgtcga tggccggctc gtcggcaatg   1260
atcttggccg cctaccaccc ccagcagttc atctacgccg gctcgctgtc ggccctgctg   1320
gacccctctc aggggatggg gcctagcctg atcggcctcg cgatgggtga cgccggcggt   1380
tacaaggccg cagacatgtg gggtccctcg agtgacccgg catgggagcg caacgaccct   1440
acgcagcaga tccccaagct ggtcgcaaac aacacccggc tatgggttta ttgcgggaac   1500
ggcaccccga acgagttggg cggtgccaac atacccgccg agttcttgga gaacttcgtt   1560
cgtagcagca acctgaagtt ccaggatgcg tacaacgccg cgggcgggca caacgccgtg   1620
ttcaacttcc cgcccaacgg cacgcacagc tgggagtact ggggcgctca gctcaacgcc   1680
atgaagggtg acctgcagag ttcgttaggc gccggcatga cagagcagca gtggaatttc   1740
gcgggtatcg aggccgcggc aagcgcaatc cagggaaatg tcacgtccat tcattccctc   1800
cttgacgagg ggaagcagtc cctgaccaag ctcgcagcgg cctggggcgg tagcggttcg   1860
gaggcgtacc agggtgtcca gcaaaaatgg gacgccacgg ctaccgagct gaacaacgcg   1920
ctgcagaacc tggcgcggac gatcagcgaa gccggtcagg caatggcttc gaccgaaggc   1980
aacgtcactg ggatgttcgc atagaagggt tcgatcccta ccggttagta atgagtttaa   2040
acgggggagg ctaactgaaa cacggaagga gacaataccg gaaggaaccc gcgctatgac   2100
ggcaataaaa agacagaata aaacgcacgg gtgttgggtc gtttgttcat aaacgcgggg   2160
ttcggtccca gggctggcac tctgtcgata ccccaccgag accccattgg ggccaatacg   2220
cccgcgtttc ttccttttcc ccaccccacc ccccaagttc gggtgaaggc ccagggctcg   2280
cagccaacgt cggggcggca ggccctgcca tagcagatct gcgcagctgg ggctctaggg   2340
ggtatcccca cgcgccctgt agcggcgcat taagcgcggc gggtgtggtg gttacgcgca   2400
gcgtgaccgc tacacttgcc agcgccctag cgcccgctcc tttcgctttc ttcccttcct   2460
```

-continued

```
ttctcgccac gttcgccggc tttccccgtc aagctctaaa tcggggcatc cctttagggt   2520
tccgatttag tgctttacgg cacctcgacc ccaaaaaact tgattagggt gatggttcac   2580
gtagtgggcc atcgccctga tagacggttt ttcgcccttt gacgttggag tccacgttct   2640
ttaatagtgg actcttgttc caaactggaa caacactcaa ccctatctcg gtctattctt   2700
ttgatttata agggattttg gggatttcgg cctattggtt aaaaaatgag ctgatttaac   2760
aaaaatttaa cgcgaattaa ttctgtggaa tgtgtgtcag ttagggtgtg gaaagtcccc   2820
aggctcccca gcaggcagaa gtatgcaaag catgcatctc aattagtcag caaccaggtg   2880
tggaaagtcc ccaggctccc cagcaggcag aagtatgcaa agcatgcatc tcaattagtc   2940
agcaaccata gtcccgcccc taactccgcc catcccgccc ctaactccgc ccagttccgc   3000
ccattctccg ccccatggct gactaatttt ttttatttat gcagaggccg aggccgcctc   3060
tgcctctgag ctattccaga agtagtgagg aggctttttt ggaggcctag gcttttgcaa   3120
aaagctcccg ggagcttgta tatccatttt cggatctgat caagagacag gatgaggatc   3180
gtttcgcatg attgaacaag atggattgca cgcaggttct ccggccgctt gggtggagag   3240
gctattcggc tatgactggg cacaacagac aatcggctgc tctgatgccg ccgtgttccg   3300
gctgtcagcg caggggcgcc cggttctttt tgtcaagacc gacctgtccg gtgccctgaa   3360
tgaactgcag gacgaggcag cgcggctatc gtggctggcc acgacgggcg ttccttgcgc   3420
agctgtgctc gacgttgtca ctgaagcggg aagggactgg ctgctattgg gcgaagtgcc   3480
ggggcaggat ctcctgtcat ctcaccttgc tcctgccgag aaagtatcca tcatggctga   3540
tgcaatgcgg cggctgcata cgcttgatcc ggctacctgc ccattcgacc accaagcgaa   3600
acatcgcatc gagcgagcac gtactcggat ggaagccggt cttgtcgatc aggatgatct   3660
ggacgaagag catcaggggc tcgcgccagc cgaactgttc gccaggctca aggcgcgcat   3720
gcccgacggc gaggatctcg tcgtgaccca tggcgatgcc tgcttgccga atatcatggt   3780
ggaaaatggc cgcttttctg gattcatcga ctgtggccgg ctgggtgtgg cggaccgcta   3840
tcaggacata gcgttggcta cccgtgatat tgctgaagag cttggcggcg aatgggctga   3900
ccgcttcctc gtgctttacg gtatcgccgc tcccgattcg cagcgcatcg ccttctatcg   3960
ccttcttgac gagttcttct gagcgggact ctggggttcg cgaaatgacc gaccaagcga   4020
cgcccaacct gccatcacga gatttcgatt ccaccgccgc cttctatgaa aggttgggct   4080
tcggaatcgt tttccgggac gccggctgga tgatcctcca gcgcggggat ctcatgctgg   4140
agttcttcgc ccaccccaac ttgtttattg cagcttataa tggttacaaa taaagcaata   4200
gcatcacaaa tttcacaaat aaagcatttt tttcactgca ttctagttgt ggtttgtcca   4260
aactcatcaa tgtatcttat catgtctgta taccgtcgac ctctagctag agcttggcgt   4320
aatcatggtc atagctgttt cctgtgtgaa attgttatcc gctcacaatt ccacacaaca   4380
tacgagccgg aagcataaag tgtaaagcct ggggtgccta atgagtgagc taactcacat   4440
taattgcgtt gcgctcactg cccgctttcc agtcgggaaa cctgtcgtgc cagctgcatt   4500
aatgaatcgg ccaacgcgcg gggagaggcg gtttgcgtat tgggcgctct tccgcttcct   4560
cgctcactga ctcgctgcgc tcggtcgttc ggctgcggcg agcggtatca gctcactcaa   4620
aggcggtaat acggttatcc acagaatcag gggataacgc aggaaagaac atgtgagcaa   4680
aaggccagca aaaggccagg aaccgtaaaa aggccgcgtt gctggcgttt ttccataggc   4740
tccgcccccc tgacgagcat cacaaaaatc gacgctcaag tcagaggtgg cgaaacccga   4800
```

```
caggactata aagataccag gcgtttcccc ctggaagctc cctcgtgcgc tctcctgttc   4860

cgaccctgcc gcttaccgga tacctgtccg cctttctccc ttcgggaagc gtggcgcttt   4920

ctcaatgctc acgctgtagg tatctcagtt cggtgtaggt cgttcgctcc aagctgggct   4980

gtgtgcacga accccccgtt cagcccgacc gctgcgcctt atccggtaac tatcgtcttg   5040

agtccaaccc ggtaagacac gacttatcgc cactggcagc agccactggt aacaggatta   5100

gcagagcgag gtatgtaggc ggtgctacag agttcttgaa gtggtggcct aactacggct   5160

acactagaag gacagtattt ggtatctgcg ctctgctgaa gccagttacc ttcggaaaaa   5220

gagttggtag ctcttgatcc ggcaaacaaa ccaccgctgg tagcggtggt ttttttgttt   5280

gcaagcagca gattacgcgc agaaaaaaag gatctcaaga agatcctttg atcttttcta   5340

cggggtctga cgctcagtgg aacgaaaact cacgttaagg gattttggtc atgagattat   5400

caaaaaggat cttcacctag atccttttaa attaaaaatg aagttttaaa tcaatctaaa   5460

gtatatatga gtaaacttgg tctgacagtt accaatgctt aatcagtgag gcacctatct   5520

cagcgatctg tctatttcgt tcatccatag ttgcctgact ccccgtcgtg tagataacta   5580

cgatacggga gggcttacca tctggcccca gtgctgcaat gataccgcga gacccacgct   5640

caccggctcc agatttatca gcaataaacc agccagccgg aagggccgag cgcagaagtg   5700

gtcctgcaac tttatccgcc tccatccagt ctattaattg ttgccgggaa gctagagtaa   5760

gtagttcgcc agttaatagt ttgcgcaacg ttgttgccat tgctacaggc atcgtggtgt   5820

cacgctcgtc gtttggtatg gcttcattca gctccggttc ccaacgatca aggcgagtta   5880

catgatcccc catgttgtgc aaaaaagcgg ttagctcctt cggtcctccg atcgttgtca   5940

gaagtaagtt ggccgcagtg ttatcactca tggttatggc agcactgcat aattctctta   6000

ctgtcatgcc atccgtaaga tgcttttctg tgactggtga gtactcaacc aagtcattct   6060

gagaatagtg tatgcggcga ccgagttgct cttgcccggc gtcaatacgg gataataccg   6120

cgccacatag cagaacttta aaagtgctca tcattggaaa acgttcttcg gggcgaaaac   6180

tctcaaggat cttaccgctg ttgagatcca gttcgatgta acccactcgt gcacccaact   6240

gatcttcagc atcttttact ttcaccagcg tttctgggtg agcaaaaaca ggaaggcaaa   6300

atgccgcaaa aaagggaata agggcgacac ggaaatgttg aatactcata ctcttccttt   6360

ttcaatatta ttgaagcatt tatcagggtt attgtctcat gagcggatac atatttgaat   6420

gtatttagaa aaataaacaa ataggggttc cgcgcacatt tccccgaaaa gtgccacctg   6480

acgtcgacgg atcgggagat ctcccgatcc cctatggtcg actctcagta caatctgctc   6540

tgatgccgca tagttaagcc agtatctgct ccctgcttgt gtgttggagg tcgctgagta   6600

gtgcgcgagc aaaatttaag ctacaacaag gcaaggcttg accgacaatt gcatgaagaa   6660

tctgcttagg                                                          6670
```

```
<210> SEQ ID NO 7
<211> LENGTH: 232
<212> TYPE: PRT
<213> ORGANISM: Artificial Sequence
<220> FEATURE:
<223> OTHER INFORMATION: p24 protein

<400> SEQUENCE: 7

Met Pro Ile Val Gln Asn Leu Gln Gly Gln Met Val His Gln Ala Ile
1               5                   10                  15

Ser Pro Arg Thr Leu Asn Ala Trp Val Lys Val Val Glu Glu Lys Ala
            20                  25                  30
```

-continued

```
Phe Ser Pro Glu Val Ile Pro Met Phe Ser Ala Leu Ser Glu Gly Ala
        35                  40                  45

Thr Pro Gln Asp Leu Asn Thr Met Leu Asn Thr Val Gly Gly His Gln
    50                  55                  60

Ala Ala Met Gln Met Leu Lys Glu Thr Ile Asn Glu Glu Ala Ala Glu
65                  70                  75                  80

Trp Asp Arg Leu His Pro Val His Ala Gly Pro Ile Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Gly Trp Met Thr His Asn Pro Pro Ile Pro Val Gly
        115                 120                 125

Glu Ile Tyr Lys Arg Trp Ile Ile Leu Gly Leu Asn Lys Ile Val Arg
    130                 135                 140

Met Tyr Ser Pro Thr Ser Ile Leu Asp Ile Arg Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ser Gln Glu Val Lys Asn Trp Met Thr Glu Thr Leu Leu Val
            180                 185                 190

Gln Asn Ala Asn Pro Asp Cys Lys Thr Ile Leu Lys Ala Leu Gly Pro
        195                 200                 205

Gly Ala Thr Leu Glu Glu Met Met Thr Ala Cys Gln Gly Val Gly Gly
    210                 215                 220

Pro Gly His Lys Ala Arg Val Leu
225                 230
```